US012060410B2

(12) United States Patent
Davidson

(10) Patent No.: US 12,060,410 B2
(45) Date of Patent: Aug. 13, 2024

(54) ANTIVIRUS PROTEINS HAVING A KRINGLE 5 SUBUNIT

(71) Applicant: CREATIVE BIOTHERAPEUTICS, LLC, Gurnee, IL (US)

(72) Inventor: Donald J. Davidson, Gurnee, IL (US)

(73) Assignee: Creative Bio Therapeutics LLC, Gurnee, IL (US)

( * ) Notice: Subject to any disclaimer, the term of this patent is extended or adjusted under 35 U.S.C. 154(b) by 0 days.

(21) Appl. No.: 17/235,652

(22) Filed: Apr. 20, 2021

(65) Prior Publication Data

US 2021/0324047 A1    Oct. 21, 2021

Related U.S. Application Data

(60) Provisional application No. 63/012,900, filed on Apr. 20, 2020.

(51) Int. Cl.
| | |
|---|---|
| C07K 14/47 | (2006.01) |
| A61K 38/00 | (2006.01) |
| C07K 14/705 | (2006.01) |
| C07K 14/81 | (2006.01) |

(52) U.S. Cl.
CPC ........ C07K 14/8132 (2013.01); C07K 14/705 (2013.01); *A61K 38/00* (2013.01)

(58) Field of Classification Search
CPC .. C07K 14/47; C07K 14/8132; C07K 14/705; A61K 38/00
See application file for complete search history.

(56) References Cited

U.S. PATENT DOCUMENTS

| | | |
|---|---|---|
| 2019/0076431 A1 | 3/2019 | Lee et al. |
| 2019/0142913 A1 | 5/2019 | Davidson |

FOREIGN PATENT DOCUMENTS

| | | |
|---|---|---|
| WO | 2010/054328 A2 | 5/2010 |

OTHER PUBLICATIONS

RCSB PDB-1TPK from https://www.rcsb.org/structure/1tpk, 1992, pp. 1-4. (Year: 1992).*
Sheahan et al, "Broad-spectrum antiviral GS-5734 inhibits both epidemic and zoontic coronaviruses," Science Translational Medicine, Jun. 28, 2017, 9: 1-10. (Year: 2017).*
De Wispelaere et al., "The small molecules AZD0530 and Dasatinib Inhibit Dengue Virus RNA Replication via Fyn Kinase," Journal of Virology, Jul. 2013, 87(13): 7367-7381. (Year: 2013).*
Wang et al., "Hydroxychloroquine-Inhibited Dengue Virus is Associated with Host Defense Machinery," Journal of Interferon & Cytokine Research, 2015, 35(3): 143-156. (Year: 2015).*
Wati et al., "Dengue Virus Infection Induces Upregulation of GRP78, Which Acts to Chaperone Viral Antigen Production," Journal of Virology, Dec. 2009, 83(24): 12871-12880. (Year: 2009).*
Ibrahim M. Ibrahim, et al; "COVID-19 spike-host cell receptor GRP78 binding site prediction", Journal of Infection, 80; Available online Mar. 10, 2020; pp. 554-562.
Amy S. Lee et al; "The COOH-Terminal Proline-Rich Region of GRP78 is a Key Regulator of Its Cell Surface Expression and Viability of Tamoxifen-Resistant Breast Cancer Cells", Neoplasia; vol. 21, No. 8; Aug. 2018; pp. 837-848.
Laszlo Patthy; "Miguel Llinas and the Structure of the Kringle Fold", The Protein Journal; Published online Mar. 31, 2021; 40; pp. 450-453.
Mario Gonzalez-Gronow; et al; "GRP78: A Multifunctional Receptor on the Cell Surface", Antioxidants & Redox Signalling; vol. 11, No. 9, 2009; 8 pages.
Jihoon Shin, et al; "Possible Involvement of Adipose Tissue in Patients With Older Age, Obesity, and Diabetes With SARS-CoV-2 Infection (COVID-19) via GRP778 (BIP/HSPA5): Significance of Hyperinsulinemia Management in COVID-19", Diabetes, vol. 70, Dec. 2021; 11 pages.
Abdo A Elfiky, et al; "Zika virus envelope-heat shock protein A5 (GRP78) binding site prediction", Journal of Biomolecular Structure and Dynamics, 39:14; 14 pages; Published online Jun. 24, 2020.
Jonathan O. Rayner; et al; "AR12 (OSU-03012) suppresses GRP78 expression and inhibits SARS-CoV-2 replication", Biochemical Pharmacology; 182; Available online Sep. 20, 2020; 11 pages.
The International Search Report mailed Jun. 14, 2022; PCT/US21/55329.
Ranu Baral, et al; "Association Between Renin-Angiotensin-Aldosterone System Inhibitors and Clinical Outcomes in Patients With COVID-19 A Systematic Review and Meta-analysis", JAMA Network Open, Mar. 31, 2021; pp. 1-18.
Laurence Booth, et al; "AR-12 Inhibits Multiple Chaperones Concomitant With Stimulating Autophaosome Formation Collectively Preventing Virus Replication", J. Cell Physiol. Oct. 2016; 231(10); pp. 2286-2302.
Hsin-Hsin Chen, et al; "AR-12 suppresses dengue virus replication by down-regulation of PI3K/AKT and GRP78", Antiviral Research, Feb. 2017; 27 pages.

(Continued)

*Primary Examiner* — Julie Ha
(74) *Attorney, Agent, or Firm* — Brown Rudnick LLP

(57) ABSTRACT

COVID-19 results from the infection of the SARS-CoV-2 virus and has spread quickly to literally infected the world. Although coronavirus spike proteins can recognize a broad range of host cell-surface proteins, inhibiting spike protein binding to a survival factor called GRP78 results in a significant reduction in SARS-CoV-2 attachment, entry and replication in lung and kidney cells. This inhibition is accomplished with a novel type of inhibitor that potently blocks the binding of SARS-CoV-2 spike protein and whole virus to surface-bound GRP78. These novel GRP78 inhibitors also down regulate cytokines (IL10, IL6), immune co-inhibitory checkpoint proteins (PD-L1, B7H3, B7H4), and up regulate immune co-stimulatory proteins (MHC-II, CD-86) resulting in the reduction of the immune suppressive nature of infected lung alveolar epithelial cells in vitro and in vivo. Finally, these novel GRP78 inhibitors inhibit the hyperfibrinolysis of infected lung cells by reducing the activation of plasmin on cell surfaces.

9 Claims, 17 Drawing Sheets

Specification includes a Sequence Listing.

(56) References Cited

OTHER PUBLICATIONS

Hin Chu, et al; "Middle East respiratory syndrome coronavirus and bat coronavirus HKU9 both can utilize GRP78 for attachment onto host cells", J. Biol. Chem. (2018); 293(30); pp. 11709-11726; Epub Jun. 10, 2018.

Marie Cohen, et al; "Role of Prostate Apoptosis Response 4 in Translocation of GRP78 from the Endoplasmic Reticulum to the Cell Surface of Trophoblastic Cells", PLOS One www.plosone.org, Nov. 2013; vol. 8, Issue 11, 8 pages.

Adelina Comas-Herrera, et al; "Mortality associated with COVID-19 in care homes: international evidence", ITCCOVID; https://ltccovid.org/2020/04/12/mortality-associated-with-covid-19-outbreaks-in-care-homes-early-international-evidence/(2020); 29 pages.

Elizabeth D. Crane, et al; "Anti-GRP78 autoantibodies induce endothelial cell activation and accelerate the development of atherosclerotic lesions", JCI Insight; Published Dec. 20, 2018; 16 pages.

Don J. Davidson, et al; "Kringle 5 of Human Plasminogen Induces Apoptosis of Endothelial and Tumor Cells through Surface-Expressed Glucose-Regulated Protein 78", Cancer Res., 65:(11) Jun. 1, 2005; 11 pages.

Abdo A. Elfiky; "Ebola virus glycoprotein GP1-host cell-surface HSPA5 binding site prediction", Cell Stress and Chaperones; Published online Apr. 14, 2020; 25: 541-548.

Abdo A. Elfiky; "SARS-CoV-2 Spike-Heat Shock Protein A5 (GRP78) Recognition may be Related to the Immersed Human Coronaviruses", Frontiers in Pharmacology; Published Dec. 11, 2020; vol. 11; Article 577467; 4 pages.

Laura Kate Gadanec, et al; "Can SARS-CoV-2 Virus Use Multiple Receptors to Enter Host Cells?", International Journal of Molecular Sciences; Published Jan. 20, 2021; 22, 992; 36 pages.

Mario Gonzalez-Gronow, et al; "GRP78: A Multifunctional Receptor on the Cell Surface", Antioxidants & Redox Signaling; vol. 11, No. 9; Apr. 2009; 9 pages.

P. Grivas, et al; "Association of clinical factors and recent anticancer therapy with COVID-19 severity among patients with cancer: a report from the COVID-19 and Cancer Consortium", Ann. Oncol; vol. 32, Issue 6; Available online Mar. 19, 2021; 14 pages.

W. Guan, et al; Clinical Characteristics of Coronavirus Disease 2019 in China, The New England Journal of Medicine, 382; pp. 1708-1720; Published on Feb. 28, 2020.

Ahmed O. Kaseb, et al; "The Impact of Angiotensin-Converting Enzyme 2 (ACE2) Expression on the Incidence and Severity of COVID-19 Infection", Pathogens Published Mar. 22, 2021, 10, 379; 12 pages.

Abdelkrim Khadir, et al; "Soluble Epoxide Hydrolase 2 Expression is Elevated in Obese Humans and Decreased by Physical Activity", International Journal of Molecular Sciences 21,2056, Published Mar. 17, 2020; 16 pages.

Sarawut Khongwichit, et al; "A functional interaction between GRP78 and Zika virus E protein", Nature Scientific Reports 11; Published Jan. 11, 2021; 19 pages.

Masayuki Koyama, et al; "Reduction of endoplasmic reticulum stress by 4-phenylbutyric acid prevents the development of hypoxia-induced pulmonary arterial hypertension", Am. J. Physiol Heart Circ Physiol 306; First published Mar. 7, 2014; 10 pages.

Uma Kant Misra, et al; "The Role of MTJ-1 in Cell Surface Translocation of GRP78, a Receptor for $\alpha_2$-Macroglobulin-Dependent Signaling[1]", The Journal of Immunology 174; 2005; pp. 2092-2097.

Minu Nain et al; "GRP78 Is an Important Host Factor for Japanese Encephalitis Virus Entry and Replication in Mammalian Cells", Journal of Virology; posted online Jan. 4, 2017; vol. 91 Issue 6; 21 pages.

Atsuko Nakatsuka, et al; "Vaspin is an Adipokine Ameliorating ER Stress in Obesity as a Ligand for Cell-Surface GRP78/MTJ-1 Complex", Diabetes, vol. 61, Nov. 2012; 10 pages.

Min Ni, et al; "Beyond the endoplasmic reticulum: atypical GRP78 in cell viability, signaling and therapeutic targeting", Published in Biochem J. Mar. 1, 2011; 434(2): 181-188.

Kyle T. Pfaffenbach, et al; "The critical role of GRP78 in physiologic and pathologic stress", Published in Curr Opin Cell Biol. Apr. 2011; 23(2): 150-156.

Fumitaka Shimizu, et al; "Glucose-regulated protein 78 autoantibody associates with blood-brain barrier disruption in neuromyelitis optica", Sciene Translational Medicine; 9, Jul. 5, 2017; 13 pages.

Asfia Soomro, et al; "Activin A and Cell-Surface GRP78 are Novel Targetable RhoA Activators for Diabetic Kidney Disease", International Journal of Molecular Sciences; 22; Published Mar. 11, 2021; 12 pages.

Yuan-Li Tsai, et al; "Characterization and Mechanism of Stress-induced Translocation of 78-Kilodalton Glucose-regulated Protein (GRP78) to the Cell Surface", The Journal of Biological Chemistry, vol. 290, No. 13, pp. 8049-8064, Mar. 27, 2015.

Robert Vertity, et al; "Estimates of the severity of coronavirus disease 2019: a model-based analysis", Lancet Infect Dis 2020; Published Online Mar. 30, 2020; 9 pages.

Yixin Xie, et al; "Revealing the Mechanism of SARS-CoV-2 Spike Protein Binding With ACE2", Published by the IEEE Computer Society, Nov./Dec. 2020; 9 pages; epub Aug. 11, 2020.

Guangyu Zhang, et al; "Unfolded Protein Response as a Therapeutic Target in Cardiovascular Disease", Published in Curr Top Med Chem. 2019: 19(21); 1902-1917.

Marcos D. Battistel, et al; "Solution Structure and Functional Characterization of Human Plasminogen Kringle 5", Biochemistry 2009, 48, 10208-10219.

Shabir A. Madhi, et al; Safety and effacy of the ChAdOx1 nCoV-19 (AZD1222) Covid-19 vaccine against the B.1.351 variant in South Africa, N. England J. Med. Mar. 16, 2021; 26 pages.

Yuan Chang, et al; "Structure and Ligand Binding Determinants of the Recombinant Kringle 5 Domain of Human Plasminogen", Biochemistry 1998, vol. 37, pp. 3258-3271.

Guanghui Liu, et al; "Apoptosis induced by endoplasmic reticulum stress involved in diabetic kidney disease", Biochemical and Biophysical Research Communications, vol. 370, pp. 651-656; Available online Apr. 15, 2008.

Lichao Zhang, et al; "GRP78 plays an integral role in tumor cell inflammation-related migration induced by M2 macrophages", Cellular Signalling vol. 37, pp. 136-148; Sep. 2017.

Abdo A. Elfiky, et al; "Zika virus envelope—heat shock protein A5 (GRP78) binding site prediction", Journal of Biomolecular Structure and Dynamics, 39:14, pp. 5248-5260; Published online Jun. 24, 2020.

\* cited by examiner

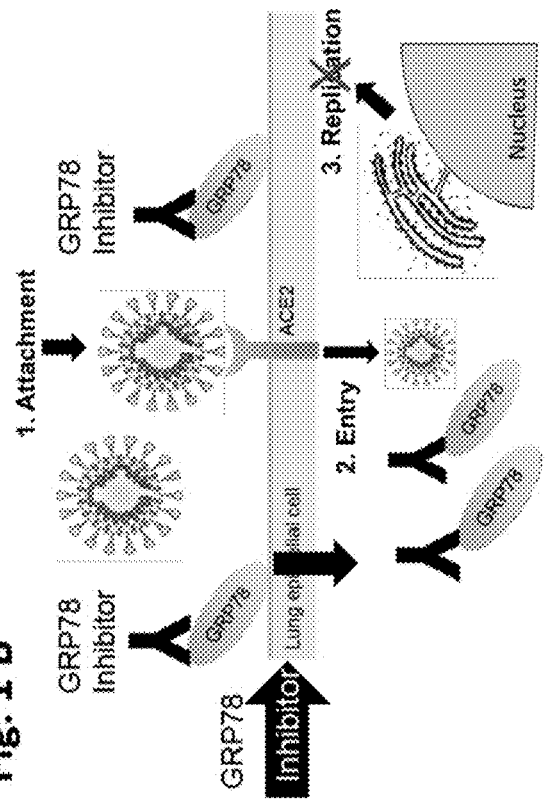
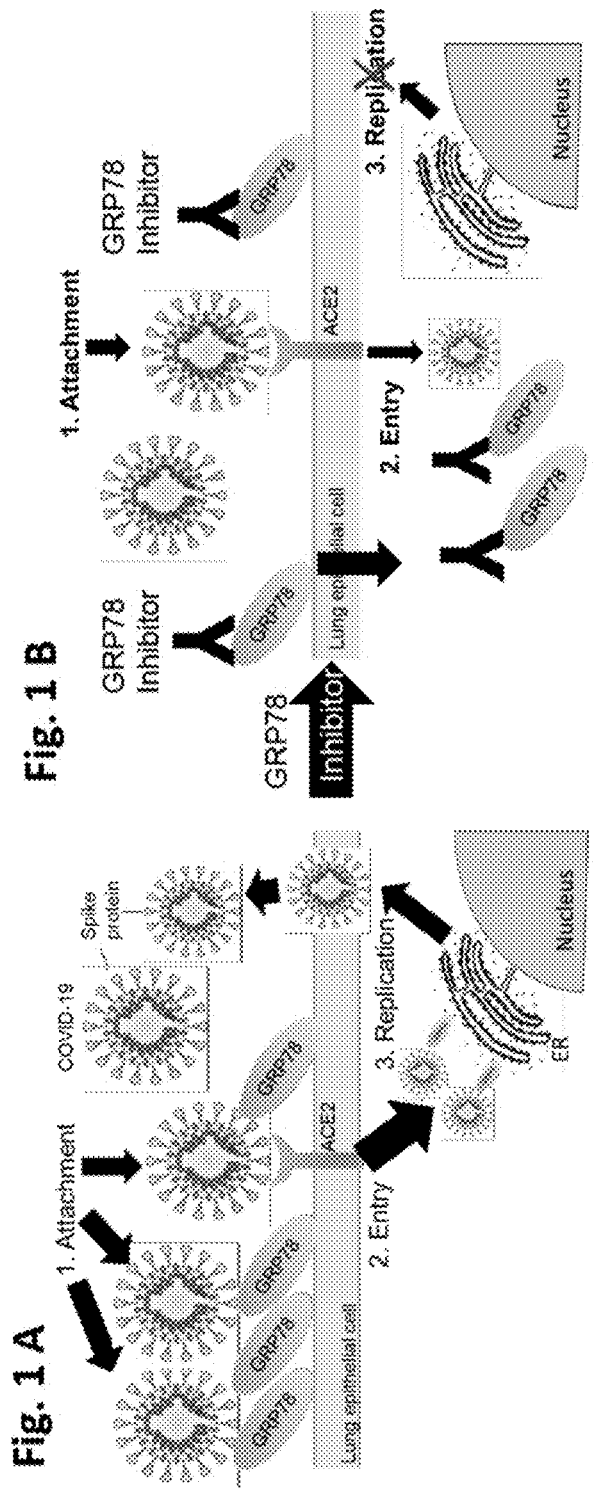
Fig. 1A
Fig. 1B

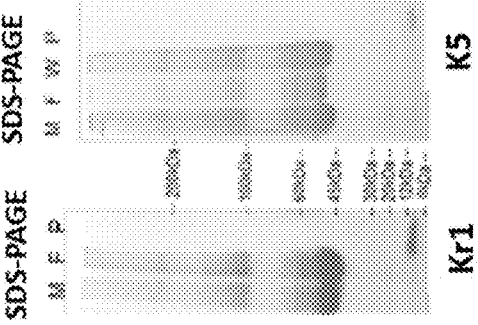
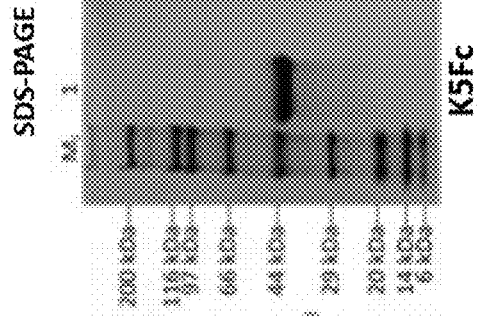
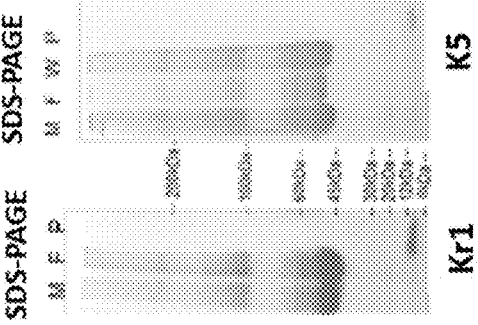
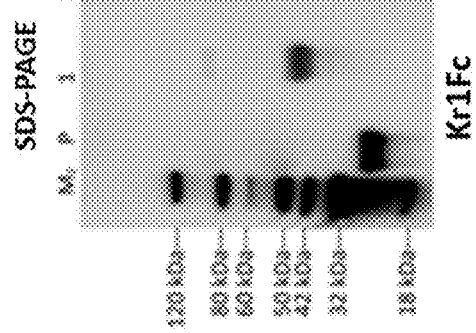
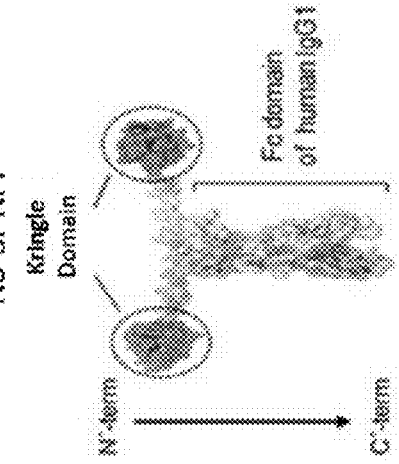
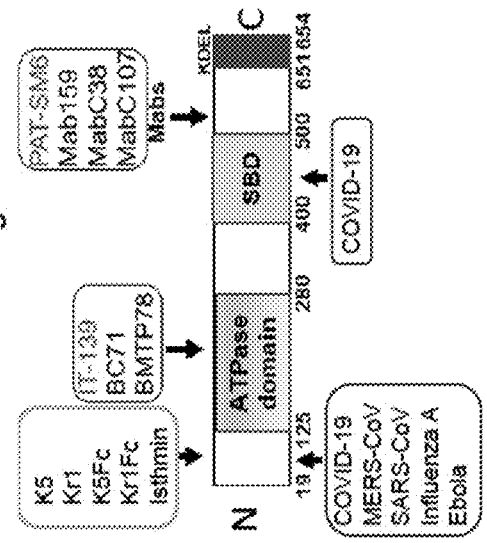

Inhibition of GRP78 Binding to Spike Protein

Binding Inhibition of GRP78 to SARS-CoV-2 Spike Protein by Kr1Fc, K5Fc, K5 or Dead Kr1Fc

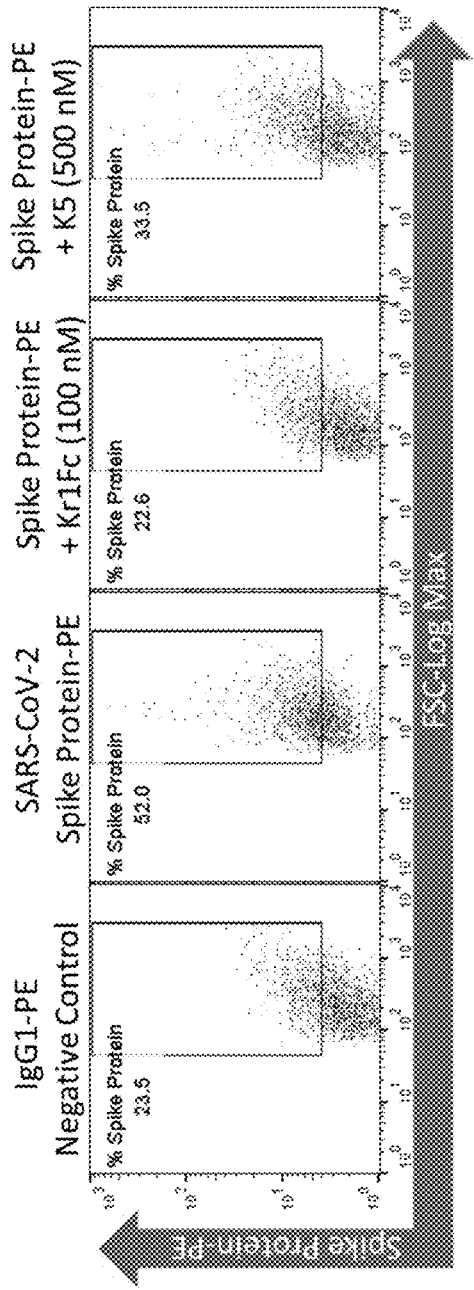
Fig. 5 A A549 Lung Cells Flow Cytometry Analysis of SARS-CoV-2 Spike Protein Binding Inhibition at 4C
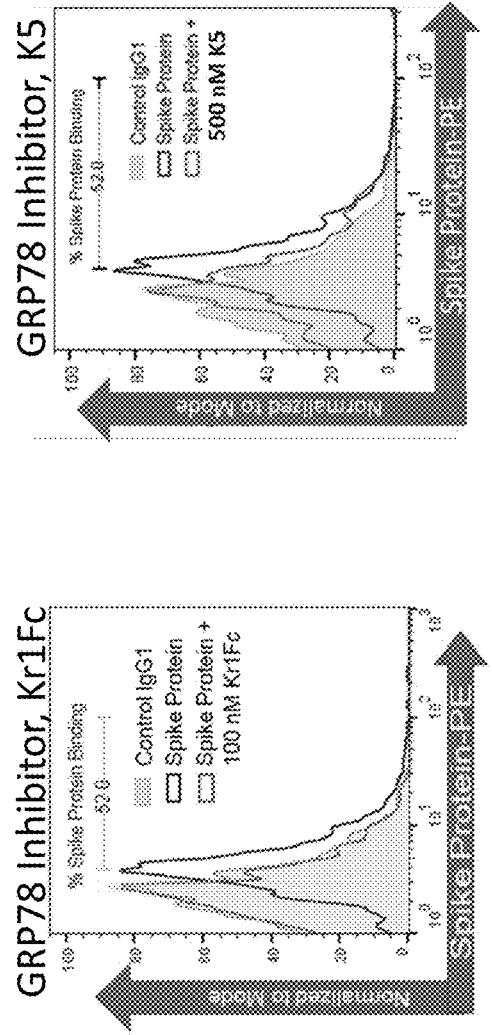
Fig. 5 B Histogram of SARS-CoV-2 Spike Protein Binding Inhibition by GRP78 Inhibitors

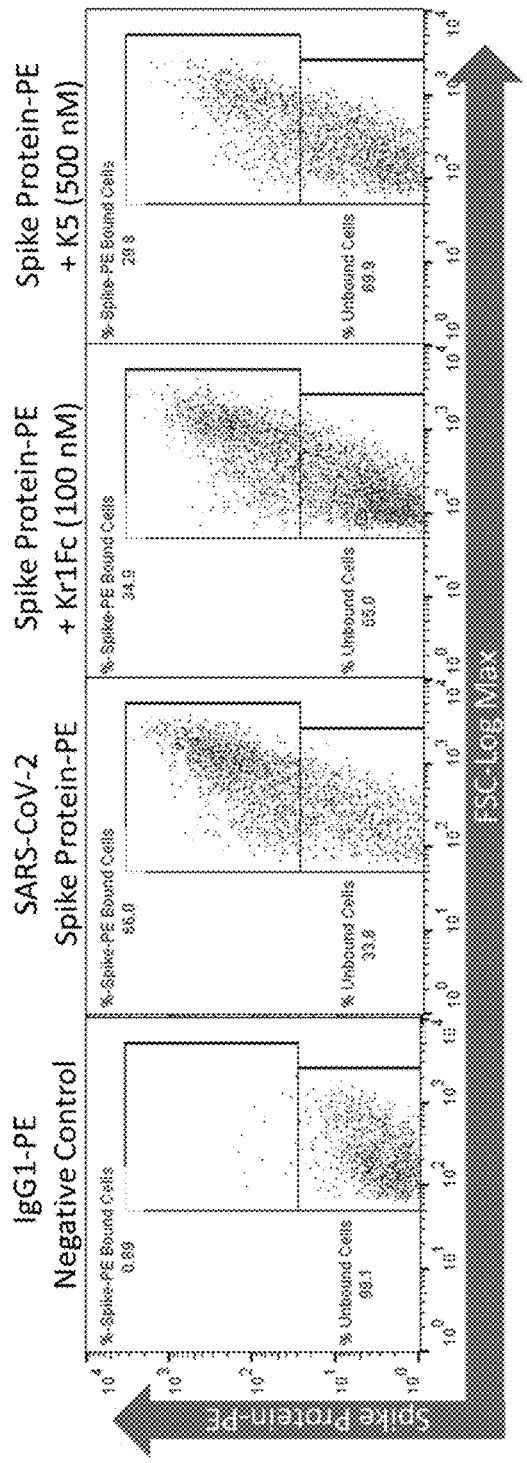
Fig. 6 A Flow Cytometry Analysis of SARS-CoV-2 Spike Protein Binding to VERO Kidney Cells added simultaneously with GRP78 Inhibitors at 37C
Fig. 6 B Histogram Overlays of SARS-CoV-2 Spike Protein Binding and GRP78 Inhibitors

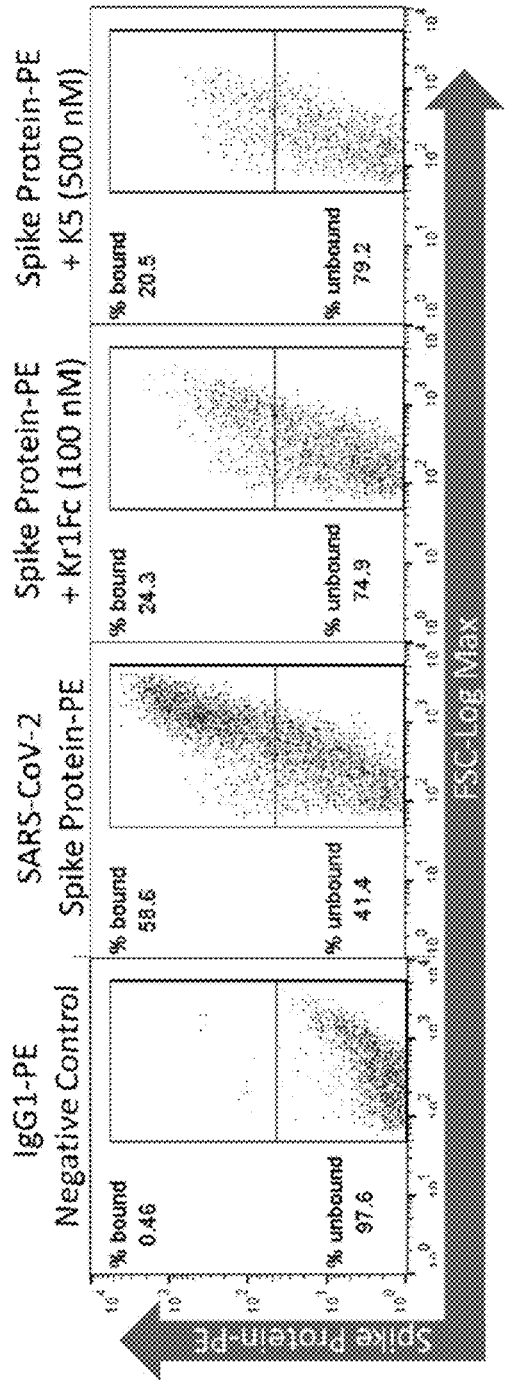
Fig. 7 A Flow Cytometry Analysis of SARS-CoV-2 Spike Protein Binding to VERO Kidney Cells Pre-incubated for 6 hours with GRP78 Inhibitors at 37C
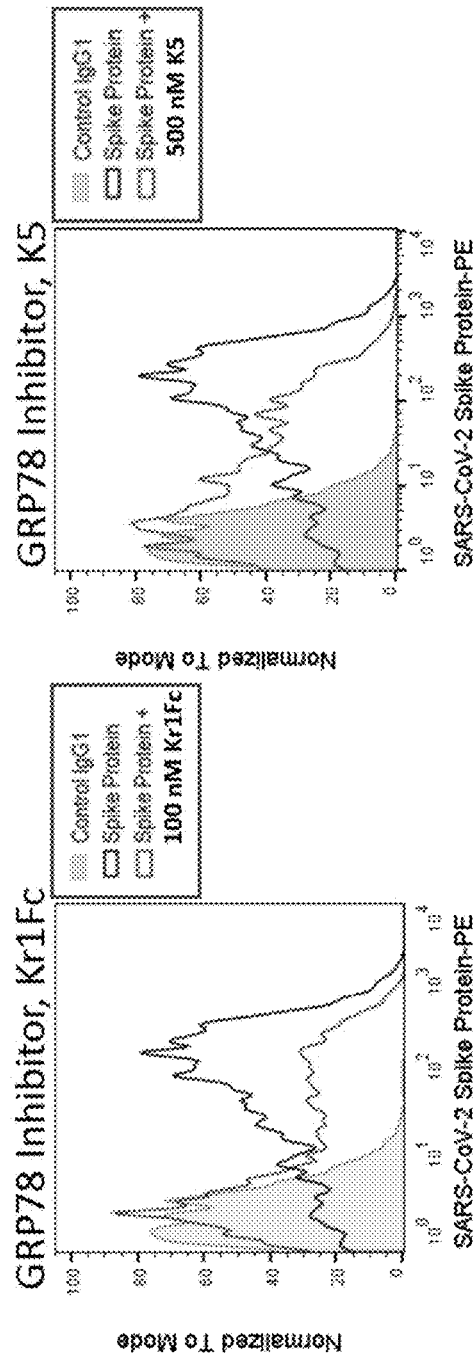
Fig. 7 B Histogram Overlays of SARS-CoV-2 Spike Protein Binding and GRP78 Inhibitors

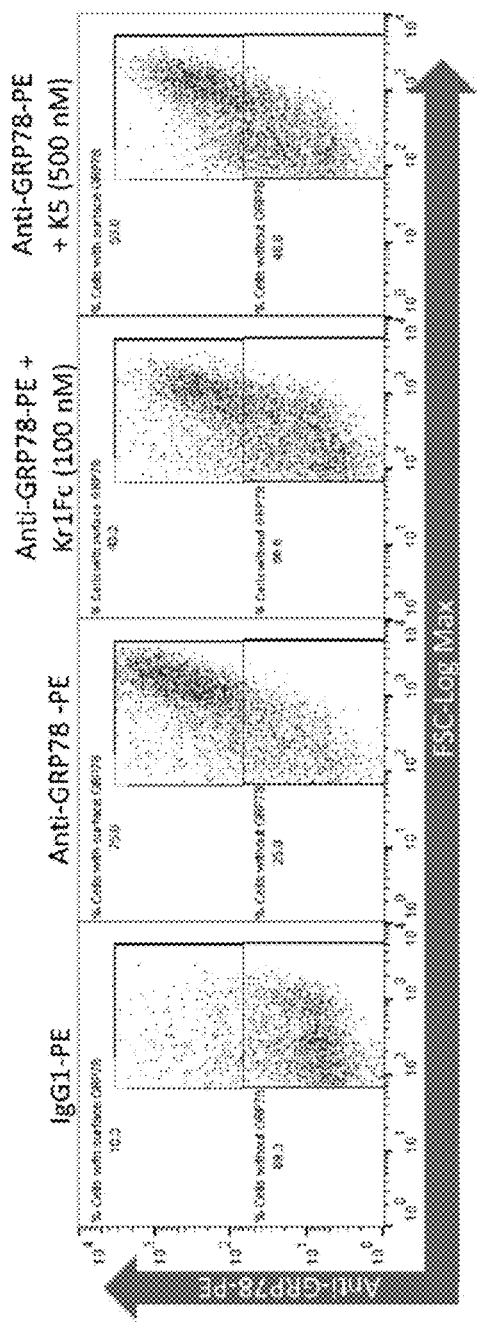
Fig. 8 A  Flow Cytometry Analysis of Surface GRP78 Expressed on VERO Cells with GRP78 Inhibitors at 37C for 48 hours
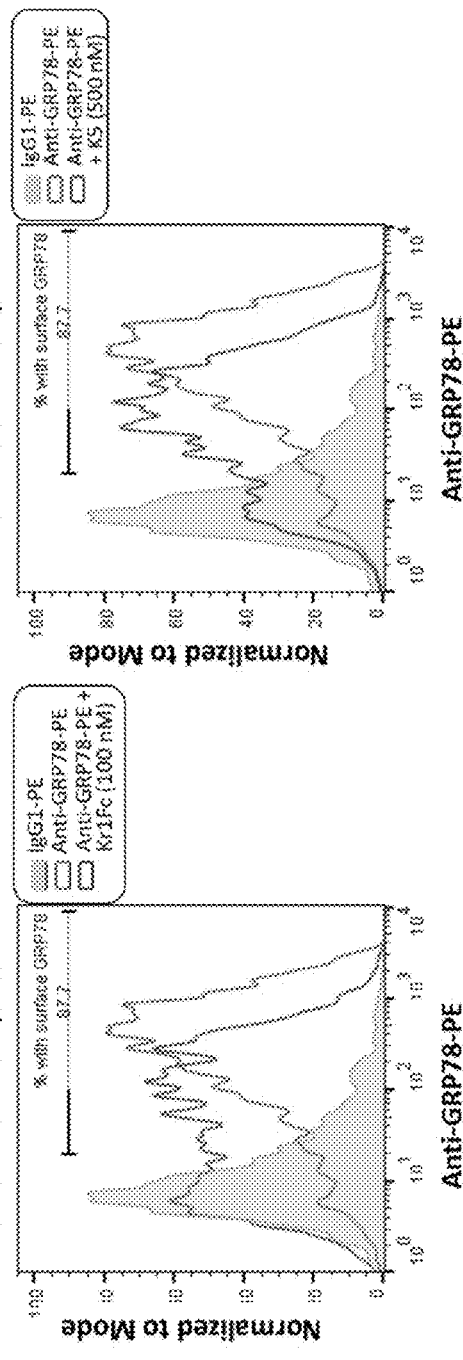
Fig. 8 B  Histogram Overlays of Surface GRP78 on VERO cells with GRP78 Inhibitors

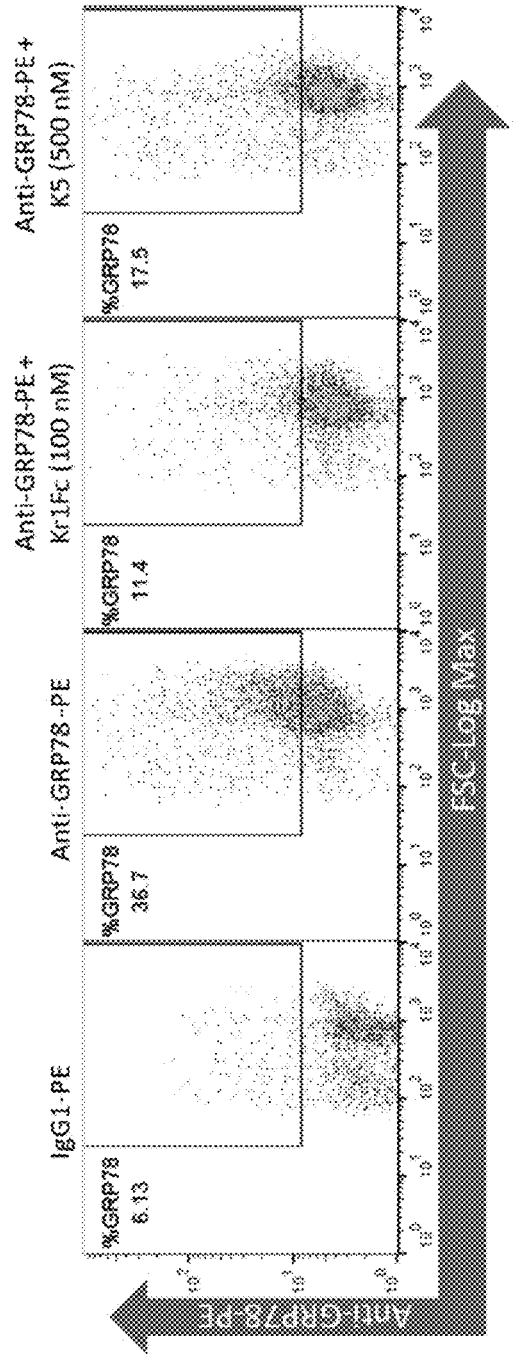
Fig. 9 A Flow Cytometry Analysis of Surface GRP78 Expressed on A549 Cells with GRP78 Inhibitors at 37C for 48 hours
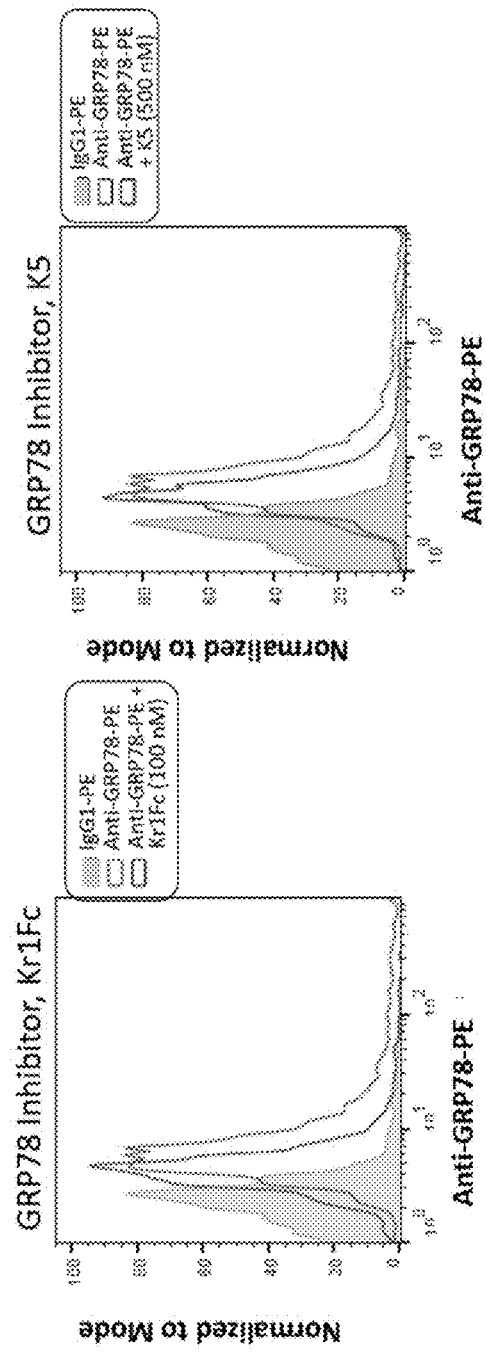
Fig. 9 B Histogram Overlays of Surface GRP78 on A549 cells with GRP78 Inhibitors

Fig. 10 A
Tracking the internalization of biomolecules using pHrodo Green and pHrodo Red dye
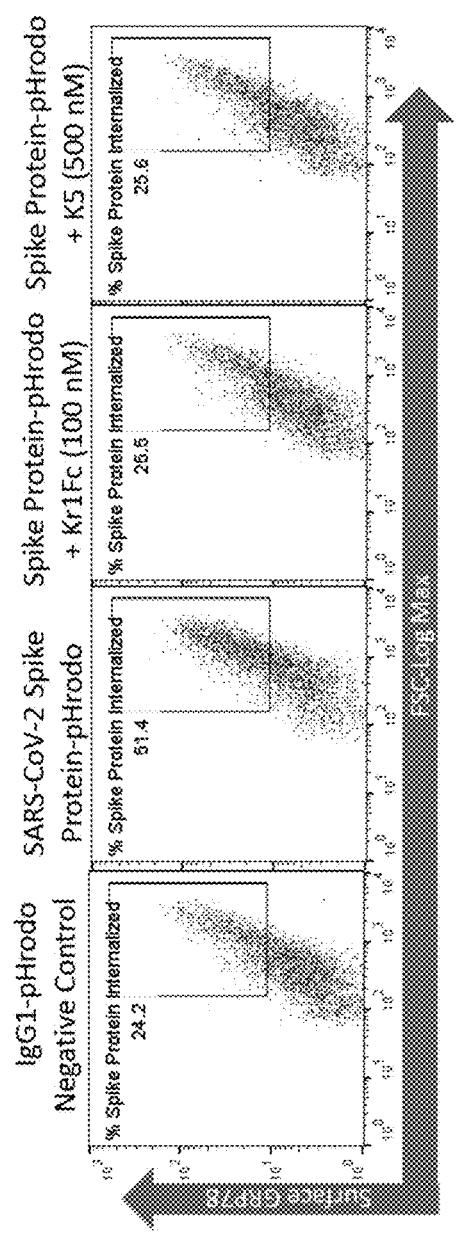
Fig. 10 B
Flow Cytometry Analysis of VERO cells treated with GRP78 inhibition and pHrodo red labeled-SARS-CoV-2 Spike protein for 48 hours
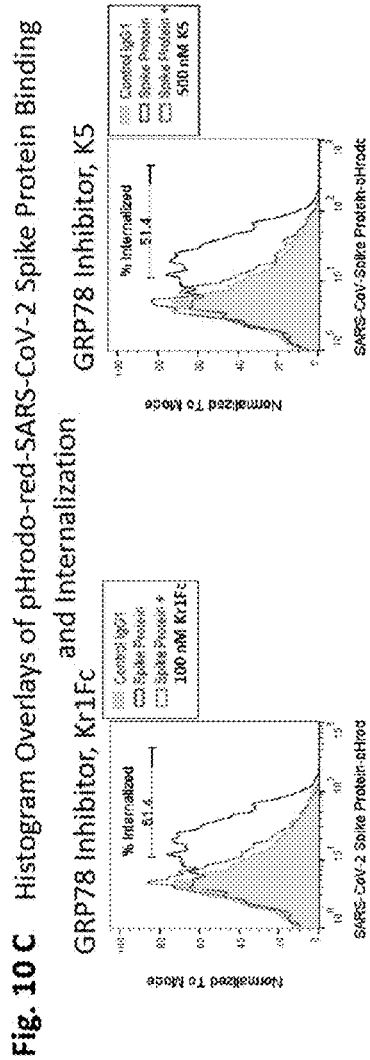
Fig. 10 C Histogram Overlays of pHrodo-red-SARS-CoV-2 Spike Protein Binding and Internalization
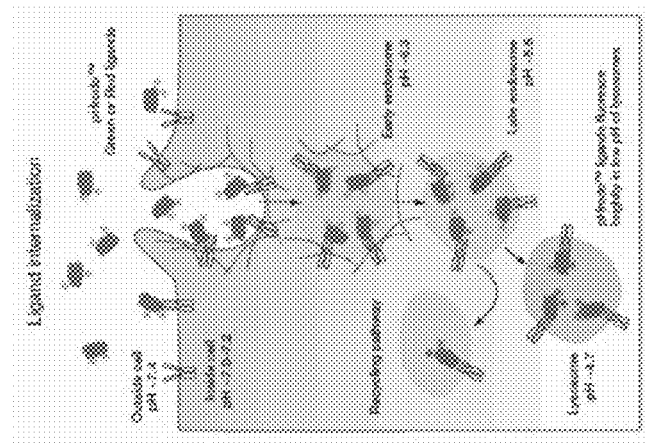
**Fig. 10 A Vero Cells 5 Day Proliferation Assay with GRP78 Inhibitors (Kr1Fc, K5)

SARS-CoV-2-Pseudotype Virus Inhibition Activity in Vero Cells with GRP78 Inhibitors Flow Cytometry Analysis of Checkpoint Proteins on A549 Cells with and without K5

K5 Prevents Checkpoint Expression on A549 cells as Determined by FACs

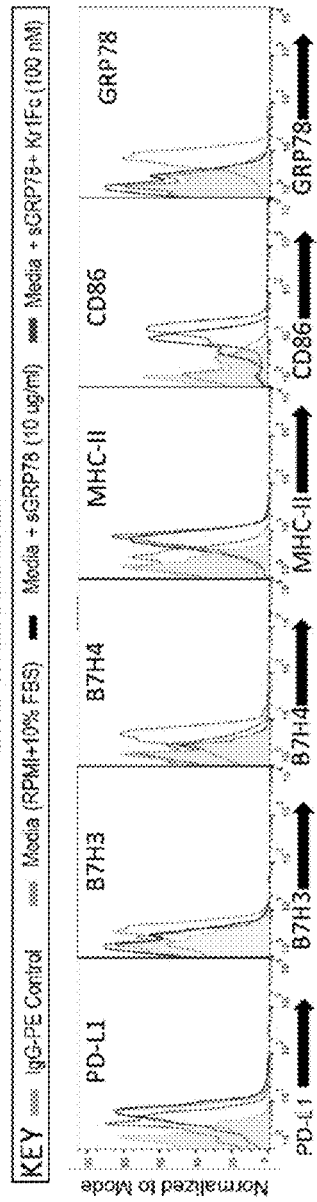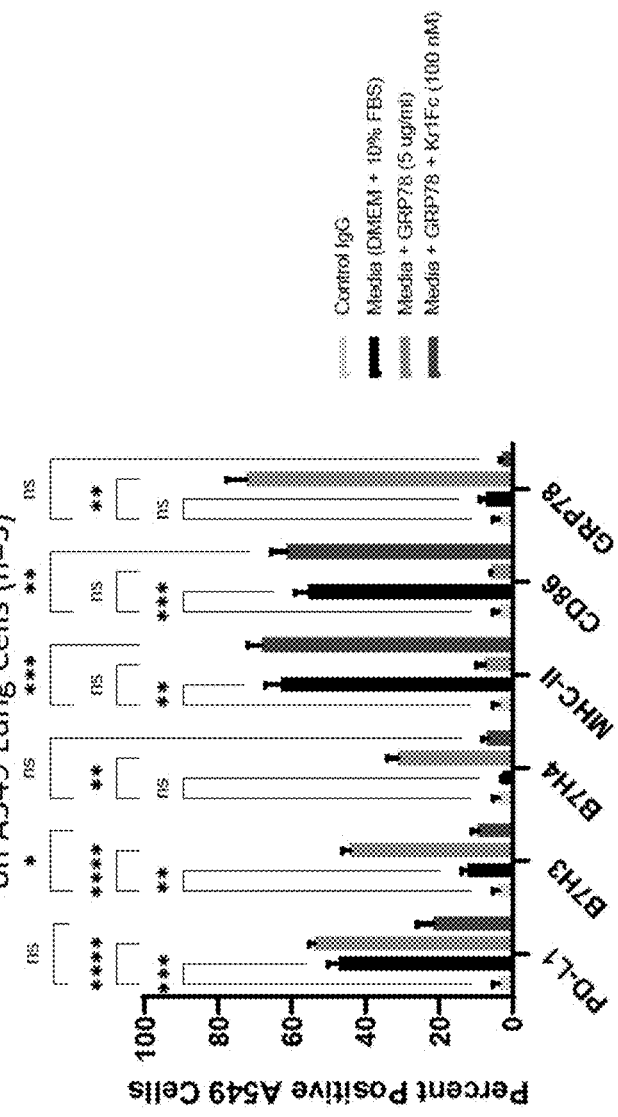
Fig. 13 A
Flow Cytometry Analysis of Checkpoint Proteins on A549 Cells with and without Kr1Fc
Fig 13 B
Kr1Fc Prevents Checkpoint Protein Expression on A549 Lung Cells (n=3)

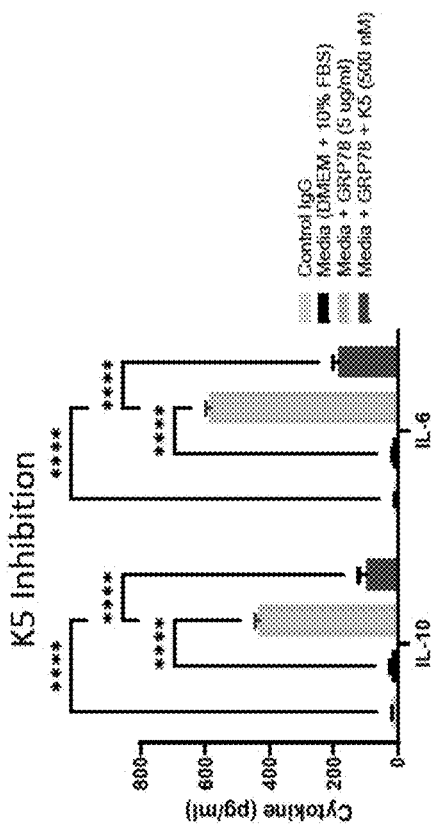
Fig. 14 A Cytokine Expression Induced by GRP78 on A549 Cells Inhibited by GRP78 Inhibitors
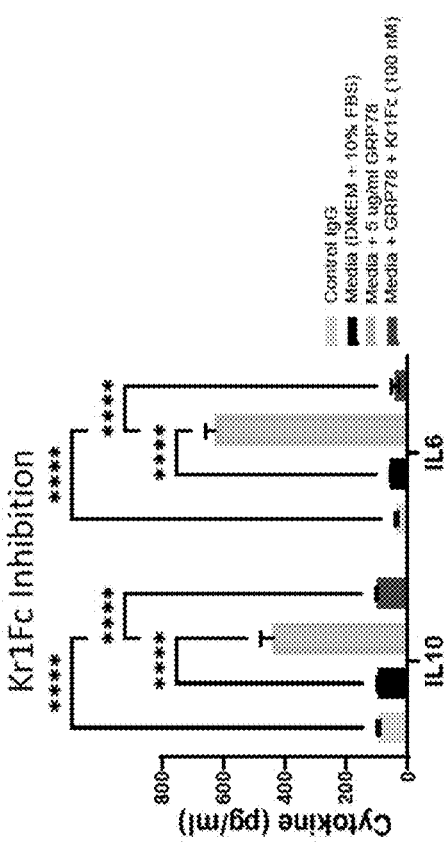
Fig. 14 B Cytokine Expression Induced by GRP78 on A549 Cells Inhibited by GRP78 Inhibitors

|  |  |  | GRP78 Recognition Site |  |  |  |
|---|---|---|---|---|---|---|
| Sequence Name | Sequence ID Number | Single Letter Amino Acid Sequence Number from Protein | * | * | * | * |
| Kringle 5 (HPg) | 190 | C524 - C536 | C Y I I N P R K . L Y D Y . . C |
| KRINGLE 1 (ROR1) | 191 | C379 - C391 | C F I . . L D E N F . K S D L C |
| SARS-CoV-2 | 192 | C480 - C488 | C . . . N G V E . G F N . . . C |
| SARS-CoV | 193 | E453 - V468 | E N G V R T L S T Y D F N P N V |
| MERS | 194 | C526 - Y540 | C V S I V P S T . V W E D G D Y |
| EBOLA | 195 | C121 - C135 | C L P A A P D G . I R G F P R C |
| ZIKA | 196 | C1074 - C1085 | C . . . P G T K . V H V E E T C |
| INFLUENZA A | 197 | C558 - C565 | C . . S N G . S . L Q . . . . C |
| DENGUE | 198 | C1091 - C1104 | C T L P P L R Y R G E D G . . C |
| JAPENESE ENCEPH | 199 | C398 - C409 | C G L F . G . K . G S I D T . C |
| WEST NILE VIRUS | 200 | C395 - C406 | C G L F . G . K . G S I D T . C |
| PEP42 | 201 | C1-C13 | C I V A L P G . . G Y V R V . C |
| HCoV-NL63 | 202 | C566 - C576 | C F S I V A V P . G S . . . . C |
| HCoV-229E | 203 | C385 - C395 | C F S L K Y I P . G G . . . . C |
| HCoV-OC43 | 204 | C508 - C522 | C V G S G P G K N N G I G I . C |
| HCoV-HKU1 | 205 | C484 - C494 | C V K S K P . . . L S A I . . C |

\* Homologous or identical GRP78 binding sites
Double Underline = identical amino acids to Kringle 5
Single Underline = homologous amino acids to Kringle 5

FIG. 17

ANTIVIRUS PROTEINS HAVING A KRINGLE 5 SUBUNIT

CLAIM OF PRIORITY AND INCORPORATION BY REFERENCE

This application claims priority from 63/012,900 filed Apr. 20, 2020. To the maximum extent permitted, as stated in application Ser. No. 63/012,900, priority is claimed based on the family of patent applications, U.S. provisional patent application No. 62/584,564 filed Nov. 10, 2017, and U.S. patent application Ser. No. 16/184,247 filed Nov. 8, 2018, published as US 2019-0142913 A1 May 16, 2019. The aforesaid publication and U.S. patent Ser. No. 10/905,750 are incorporated by reference as if fully set forth herein.

SEQUENCE LISTING

The application contains a sequence listing which has been submitted in ASCII format via EFS-Web and is hereby incorporated by reference in its entirety. The ASCII-formatted sequence listing, created Jan. 23, 2024, is named "CREAT-002-01US-ST25" and is 164,195 bytes in size.

DESCRIPTION OF RELATED ART

COVID-19 is an abbreviation from "coronavirus disease 2019" that is a result of an infection from a coronavirus called SARS-CoV-2. This viral infection has been declared a pandemic by the WHO and is considered by the CDC as a serious public health problem. Cases of COVID-19 are exploding worldwide and as of yet there is no approved cure. COVID-19 can result in severe respiratory illness in patients with pre-existing conditions and in older adults leading to permanent lung damage and death.

Currently, the use of two anti-malaria drugs, chloroquine and hydroxychloroquine, have both shown promise in preventing SARS-CoV-2 virus from infecting cells in the laboratory. Recently, in a small number of preliminary clinical trials against COVID-19 using hydroxychloroquine and an antibiotic showed that in the blood of treated patients the amount of virus was reduced much faster than in nontreated patients. These results are encouraging and even though the side-effects of heart and nerve damage as well as suicidal thoughts are manageable, they are still disturbing. These studies have also not yet shown that the patients lived longer or were more likely to recover with hydroxychloroquine. Finally, in a very recent report another treatment, Leronlimab, which is an antibody against CCR5 has shown positive results in 8 patients. CCR5 inhibitors have been shown to reduce the COVID-19 stimulated inflammatory cytokine storm in the lungs allowing for more time for recovery. Leronlimab is not a cure or a vaccine. Again, there is an urgent and unmet need for safe, effective new drugs to treat COVID-19.

The off-label therapies described above are being used in the clinic for COVID-19 patients but were not designed for specific inhibition of SARS-CoV-2 virus attachment, entry and replication. Despite this, these off label therapies have shown some desirable responses. Although some results look promising, many patients do not respond to these therapies and many deaths worldwide are still happening. New drugs that specifically target the SARS-CoV-2 virus infection are badly needed. Our work to create novel GRP78 inhibitors for anti-cancer and anti-immune suppression, could be one of the new targets and therapies for COVID-19 that is badly needed.

Understanding the mechanism of how viruses and host cell-surface proteins interact could help define their tropism, pathogenicity and lead to potential new targets for inhibition. For example, recent publications have described a role for surface-bound GRP78 during virus entry and replication. GRP78 was identified as a co-receptor for Coxsackievirus A9 and Dengue virus for attachment and entry. In addition, for the Japanese encephalitis virus (JEV), cell surface GRP78 is important for viral entry and critical for virus replication. Surface-bound GRP78 is also known to serve as an attachment factor for four betacoronaviruses, MERS-CoV, bCoV-HKU9, SARS-CoV, and SARS-CoV-2. FIG. 1 illustrates how coronaviruses use GRP78 as a co-receptor for attachment, internalization and replication. Virus infection of lung airway cells also results in the up regulation of GRP78 surface expression, which leads to further attachment and enhanced viral entry of infected cells.

Although coronavirus spike proteins can recognize a broad range of host cell-surface proteins, inhibiting GRP78, by either knockdown with siRNA, or cleavage with subtoxin A, or with an antibody, results in significant reduction in virus attachment, entry and replication. High expression of GRP78 was shown to be on the surface of stressed epithelial and endothelial cells along the human airways. Recently, it has been shown that cigarette smoke increased surface expression of GRP78 on stressed bronchial epithelial cells. Since COVID-19 has been shown to be worse in people that smoke, vape, have respiratory disease or are older, we suspect the expression of surface GRP78 on lung epithelial cells is significantly higher in this population. Even though expression of GRP78 alone was not enough to render nonpermissive cells susceptible to MERS-CoV infection, it has been shown that GRP78 is critical for viral entry and replication.

BRIEF SUMMARY OF THE INVENTION

I have discovered that surface-bound GRP78 on A549 adenocarcinoma human alveolar basal epithelial cells and VERO epithelial cells up regulates immune co-inhibitory checkpoint proteins, PD-L1, B7H3, B7H4 and down regulates immune co-stimulatory proteins, MHC-II and CD86. I have also discovered that surface-bound GRP78 up regulates cytokines IL-10, IL6, on A549 adenocarcinoma human alveolar epithelial cells which results in the blunting of the immune response. I have created a class of novel and potent inhibitors that specifically bind to the N-terminal domain of GRP78 that block the binding of SARS-CoV-2 virus to GRP78 and completely reverses cytokine expression and the immune suppressive phenotype on lung epithelial A549 cells and VERO epithelial cells (FIG. 1B). Stressed epithelial cells up regulate surface bound GRP78 that not only acts as a co-receptor for SARS-COV-2 virus to assist in attachment, entry and replication, but also blunts the immune response against SARS-COV-2 virus and infected cells. The GRP78 inhibitor of the invention can significantly reduce the attachment, entry and replication of SARS-COV-2 virus as well as reduce the immune suppressive nature of infected lung alveolar epithelial cells in vitro and in vivo.

DESCRIPTION

Dr. Dvorak published that a tumor is like a wound that won't heal. A very general analogy is that the same kind of mechanism exists for SARS-CoV-2 infection where the infection in the lungs is like a wound that won't heal. Viral infection induces enormous stress upon the infected cells and increases expression of GRP78 as happens in the tumor microenvironment (TME). The TME induces a pro-inflammatory, immune suppressive tumor cells similar to what is observed with viral infections on their target cells. In the co-pending GRP78 Antagonist application GRP78 inhibitors, Kr1Fc, K5Fc and K5 can block GRP78's interaction with cell surface receptors and decrease the immune suppressive, inflammatory nature of tumor cells. We now show for the first time that our GRP78 inhibitors, Kr1Fc, K5Fc and K5 can block the binding of SARS-CoV-2 spike protein to GRP78 with nM potency. Furthermore, our GRP78 inhibitors, Kr1FC and K5, potently block whole live virus, pseudotyped SARS-CoV-2, attachment and entry into VERO kidney epithelial cells. Specifically, the co-pending GRP78 Antagonist application teaches:

A surface-bound GRP78 inhibitor blocks SARS-COV-2 spike protein attachment and entry. The co-pending GRP78 Antagonist application teaches inhibitors to GRP78 on endothelial and cancer cells. These inhibitors have now been tested against SARS-COV-2 virus binding to GRP78 and to human lung cells. A lead inhibitor, containing the kringle domain of ROR1 fused to a human IgG1 Fc domain (Kr1Fc), binds with high affinity to the N-terminal domain of GRP78. The invention teaches that Kr1Fc, K5Fc and K5 potently block the binding of SARS-COV-2 spike protein to GRP78. The disclosed GRP78 inhibitors are effective at blocking the attachment, entry and replication of SARS-COV-2 pseudotyped virus.

A new mechanism that promotes immune tolerance that is readily targetable. Over expression of GRP78 in stressed cells leads to a large increase in surface-bound GRP78. The invention teaches that surface-bound GRP78 on human A549 adenocarcinoma alveolar basal epithelial cells induces the expression of A) cytokines IL-10, and IL-6, B) immune co-inhibitory checkpoint proteins, PD-L1, B7H3, B7H4, and C) suppresses the expression of immune co-stimulatory proteins, MHC-II, and CD86. By blocking GRP78 binding to surface proteins with Kr1Fc, the immune-suppressive phenotype of A549 cells can be reversed. In the invention, inhibition of GRP78 binding to SARS-COV-2 SPIKE PROTEIN will lead to a decrease in viral load, cytokine storm and immune suppression associated with SARS-COV-2 infection.

Novel GRP78 inhibitors that bind to the N-terminal domain of GRP78 reduce surface GRP78 expression which is only expressed on stressed cells and not normal cells, leads to a safer therapy than other currently approved anti-viral therapies. The invention teaches potent inhibitors that bind tightly to the N-terminal domain of GRP78 resulting in the inhibition of SARS-CoV-2 virus binding. In the invention the inhibitors to surface-bound GRP78 are safe in CEREP receptor binding and in normal fibroblast proliferation assays. Previously practiced therapies being used against COVID-19 like hydroxychloroquine, bind weakly to SARS-CoV-2's receptor ACE2 on lung epithelial cells. The fact that ACE2 is expressed on several other normal cells and that hydroxychloroquine has such a weak binding affinity, supports the off-target side-effects of this drug seen in clinical trials. Another drug approved for treatment of SARS-CoV-2 virus is Remdesivir. Remdesivir is an adenosine analogue that blocks mitochondrial RNA polymerase essential for virus replication. However, there are several off-target toxicities in the gut and lungs with Remdesivir and it too must be used cautiously. This invention teaches GRP78, which is not expressed on the surface of normal cells is a safer and more effective target for therapies against COVID-19.

The invention also teaches that N-terminal GRP78 inhibitors block SARS-CoV-2 virus induced hyperfibrinolysis and coagulopat+hy ("clot storm") through inhibition of plasmin generation (FIG. 2). Patients with severe COVID-19 have comorbidities like hypertension, heart disease, diabetes, and cancer that are known to have serious coagulopathies. Hyperfibrinolysis, reflected by elevated serum D-dimer levels, was present in 97% of the severe COVID-19 patients before death. Plasmin, a key player in hyperfibrinolysis and as such D-dimer levels, also enhances the virulence and pathogenicity of the SARS-CoV-2 virus by clipping a furin site on its envelope protein. Kr1Fc, K5Fc, and K5 can also block the activation of plasmin on lung epithelial and endothelial cell surfaces leading to reduced fibrinolysis, D-dimer formation and furin site cleavage. Not only will our GRP78 inhibitors significantly block SARS-CoV-2 virus attachment, entry and replication but they also reduce the cytokine storm, inhibit hyperfibrinolysis and increase the immune surveillance against SARS-CoV-2 virus (FIG. 2). The invention teaches N-terminal binding GRP78 inhibitors either alone or in combination with other therapies will significantly reduce the pathogenicity of COVID-19.

BRIEF DESCRIPTION OF THE DRAWINGS

FIG. 1a is a schematic of SARS-CoV-2 virus attachment, entry and replication with and without GRP78 inhibitors.

FIG. 1b is a schematic of SARS-Cov-2 virus attachment, entry and replication with GRP78 inhibitors.

FIG. 3A is an analysis of Kr1Fc (SEQ ID NO: 20) proteins purity, structure and binding to GRP78.

FIG. 3B is an analysis of K5Fc (SEQ ID NO: 2) proteins purity, structure and binding to GRP78.

FIG. 3C is an analysis of Kr1 (SEQ ID NO: 19) proteins purity, structure and binding to GRP78.

FIG. 3D is an analysis of K5 (SEQ ID NO: 1) proteins purity, structure and binding to GRP78.

FIG. 3E is an analysis of K5 (SEQ ID NO: 1) or KR1 (SEQ ID NO: 19) proteins purity, structure and binding to GRP78.

FIG. 3F is an analysis of proteins inhibitor binding on Human GRP78.

FIG. 5 A is a series of graphs that show that GRP78 inhibitors block binding of PE-labeled SARS-CoV-2 spike protein to A549 lung cells.

FIG. 5 B is two histograms that show that GRP78 inhibitors block binding of PE-labeled SARS-CoV-2 spike protein to A549 lung cells.

FIG. 6 A is a series of graphs that show that GRP78 inhibitors prevent SARS-CoV-2 spike protein-PE binding to VERO cells.

FIG. 6 B is two histograms that show that GRP78 inhibitors prevent SARS-CoV-2 spike protein-PE binding to VERO cells.

FIG. 7 A is a series of graphs that show that Kr1Fc (SEQ ID NO: 20) and K5 (SEQ ID NO: 1) prevent binding of SARS-CoV-2 spike protein either with preincubation with VERO cells or added at the same time as the spike protein.

FIG. 7 B is two histograms that show that Kr1Fc (SEQ ID NO: 20) and K5 (SEQ ID NO: 1) prevent binding of SARS-CoV-2 spike protein either with preincubation with VERO cells or added at the same time as the spike protein.

FIG. 8 A is a series of graphs that demonstrate that N-terminal GRP78 inhibitors reduce the expression of surface-bound GRP78 on VERO cells.

FIG. 8 B is two histograms of graphs that demonstrate that N-terminal GRP78 inhibitors reduce the expression of surface-bound GRP78 on VERO cells.

FIG. 9 A is a series of graphs that demonstrate that N-terminal GRP78 inhibitors reduce the expression of surface-bound GRP78 on A549 lung cells.

FIG. 9 B is two histograms of graphs that demonstrate that N-terminal GRP78 inhibitors reduce the expression of surface-bound GRP78 on A549 lung cells.

FIG. 10 A is a schematic that shows that surface-bound GRP78 expression on VERO cells, which is significantly reduced by Kr1Fc (SEQ ID NO: 20) and K5 (SEQ ID NO: 1), is essential for SARS-CoV-2 spike protein internalization.

FIG. 10 B is a series of graphs that show that surface-bound GRP78 expression on VERO cells, which is significantly reduced by Kr1Fc (SEQ ID NO: 20) and K5 (SEQ ID NO: 1), is essential for SARS-CoV-2 spike protein internalization.

FIG. 10 C is histograms that show that surface-bound GRP78 expression on VERO cells, which is significantly reduced by Kr1Fc (SEQ ID NO: 20) and K5 (SEQ ID NO: 1), is essential for SARS-CoV-2 spike protein internalization.

FIG. 11 B is a graph that demonstrates that GRP78 inhibition with N-terminal GRP78 binding proteins, Kr1Fc (SEQ ID NO: 20) and K5 (SEQ ID NO: 1), potently and significantly inhibit whole SARS-CoV-2 pseudotyped virus attachment and internalization on VERO cells.

FIG. 12 B is a histogram which illustrates that K5 significantly augments co-inhibitory (PD-L1, B7H4) checkpoint protein and co-stimulatory (CD86, MHC-II) protein expressions induced by soluble GRP78 on A549 lung cells.

FIG. 13 A is a series of graphs that show that Kr1Fc (SEQ ID NO: 20) significantly augments expression of co-inhibitory (PD-L1, B7H4) checkpoint protein and co-stimulatory (CD86, MHC-II) protein expressions induced by soluble GRP78 on A549 lung cells.

FIG. 13 B is a histogram that shows that Kr1Fc (SEQ ID NO: 20) significantly augments expression of co-inhibitory (PD-L1, B7H4) checkpoint protein and co-stimulatory (CD86, MHC-II) protein expressions induced by soluble GRP78 on A549 lung cells.

FIGS. 14 A and B are histograms that demonstrate that Kr1Fc (SEQ ID NO: 20) and K5 (SEQ ID NO: 1) inhibit soluble GRP78 induced cytokine expression of IL10 and IL6 from A549 lung cells.

FIG. 15 B is a histogram that shows that Kr1Fc (SEQ ID NO: 20) inhibit the activation of human plasminogen on VERO cell surfaces.

FIG. 17 is a table showing GRP78 recognition binding sequences from several viruses compared to known GRP78 binding sequences from K5 (SEQ ID NO: 190) and Kr1 (SEQ ID NO: 191).

DETAILED DESCRIPTION

My previous publications, incorporated by reference, teach that the 5th kringle domain of human plasminogen (K5) (SEQ ID NO: 1) bound to surface GRP78 to induce inhibition of tumor angiogenesis and tumor growth. However, K5 (SEQ ID NO: 1) was not considered to be a good drug candidate due to its unknown mechanism of action and poor half-life in mice and monkeys (<20 min). By determining how soluble GRP78 binds to tumor cell surfaces, a novel GRP78 binding protein was identified and is called receptor tyrosine kinase-like receptor-1 (ROR1). Predictably, ROR1 has a kringle domain that is very similar (>70%) to K5. The ROR1 kringle domain, Kr1 (SEQ ID NO: 19), binds to GRP78 100×s tighter (Kd=0.005 nM) than K5 (Kd=0.6 nM). The invention also shows that the ROR2 has a >70% homology to K5 and will have similar activity as ROR1 kringle domain. As shown in FIG. 3, the invention discloses novel kringle fusion protein that contains the ROR1 kringle domain, Kr1 (SEQ ID NO: 19), and a human IgG1 Fc domain. The addition of an IgG Fc domain to peptides has been shown to increase plasma half-life. We have now expressed the fusion proteins, Kr1Fc (SEQ ID NO: 20) and K5Fc (SEQ ID NO: 2) in Expi293F HEK cells and ExpiCHO cells and purified them over a Protein A column. The binding of the recombinant Kr1Fc (SEQ ID NO: 20), Kr1 (SEQ ID NO: 19), K5 (SEQ ID NO: 1), and K5Fc (SEQ ID NO: 2) proteins to benzamidine-agarose as a second purification column suggests that the kringle domains are folded properly. At the time of this writing, I have expressed and purified about 600 mgs of Kr1Fc (SEQ ID NO: 20), 2 mgs of K5Fc (SEQ ID NO: 2), 10 mgs of Kr1 (SEQ ID NO: 19), and 600 mgs of K5 (SEQ ID NO: 1). The references incorporated by reference discloses soluble GRP78 inhibitors Kr1Fc (SEQ ID NO: 20), K5Fc (SEQ ID NO: 2), Kr2Fc (SEQ ID NO: 34), and Kr1 (SEQ ID NO: 19) for use as anticancer agents.

Binding Inhibition Example #1

GRP78 Inhibitors Kr1Fc, K5Fc and K5 Inhibit SARS-CoV-2 Spike Protein Binding to GRP78.

Figure 4A:
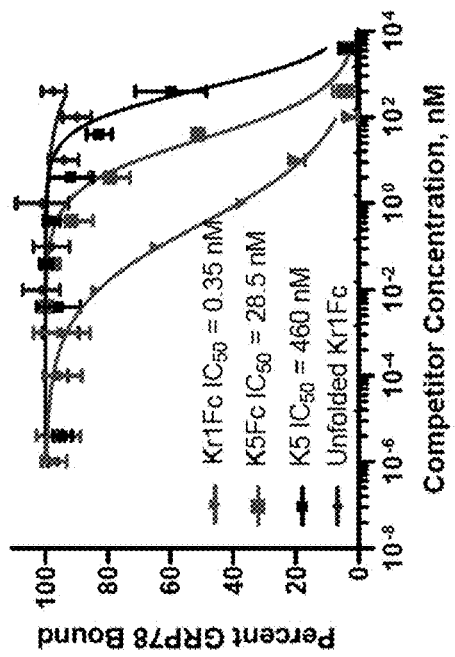
FIG. 4A is a schematic that shows that N-terminal GRP78 inhibitors block binding of GRP78 to SARS-CoV-2 spike protein.
Figure 4B:
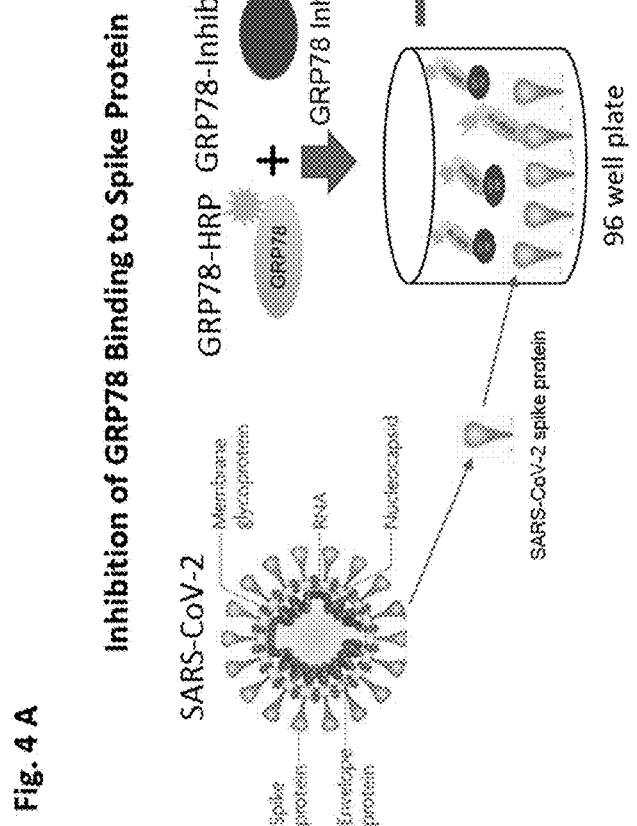
FIG. 4 B is a graph that show that N-terminal GRP78 inhibitors block binding of GRP78 to SARS-CoV-2 spike protein.

The prior art describes that GRP78 binds to the spike protein of SARS-CoV-2 virus. The prior art does not disclose what the affinity of binding was for SARS-CoV-2 spike protein with GRP78. Using an ELISA assay, this invention examines that GRP78-HRP binds to plate bound SARS-CoV-2 spike protein with a Kd of 293+35 nM. To determine if Kr1Fc, K5Fc and K5 can block this binding, this invention teaches to coat a 96 well plate with SARS-CoV-2 spike protein (100 nM) overnight at 4 C. The plate was then blocked with skimmed milk at room temperature for 30 min. HRP-labeled GRP78 (200 nM) is then added to the plates with various concentrations of Kr1Fc, K5Fc, K5 and a negative control, unfolded Kr1Fc. The plates were then incubated at room temperature for 2 hours. Finally, the wells were washed with PBS and then 1-step ultra TMB-ELISA reagent was added to each well and incubated at room temperature for 60 minutes and then read at 450 nM on a spectrophotometer. FIG. 4, shows that Kr1Fc, K5Fc and K5 inhibit GRP78 binding to the SARS-CoV-2 spike protein with IC50 values of 0.35 nM, 28.5 nM and 460 nM respectively. The unfolded Kr1Fc negative control showed no inhibition of SARS-CoV-2 spike protein binding to GRP78. This invention indicates that the invention GRP78 N-terminal binding inhibitors potently block GRP78 and SARS-CoV-2 spike protein binding.

Binding Inhibition Example #2

GRP78 Inhibitors Kr1Fc and K5 Inhibit SARS-CoV-2 Spike Protein Binding to A549 Alveolar Epithelial Adenocarcinoma Cells at 4 C.

In FIG. 5, this invention examines if Kr1Fc and K5 could block binding of PE-labeled SARS-CoV-2 spike protein to A549 lung cells. A549 cells (50,000 cells/100 uL) were added to Eppendorf tubes in PBS. GRP78 inhibitors, at various concentrations, and 50 nM PE-labeled SARS-CoV-2 spike protein were added to the cells and incubated overnight at 4 C to block internalization of the receptors. Cells were washed 2-times with PBS and run on a Guava PCA flow cytometer. The negative control used was a human IgG1-PE antibody. Flow cytometry analysis shows that SARS-CoV-2-PE spike protein bound to 52% of the A549 cells compared to control IgG1-PE antibody at 23% of cells. Kr1Fc at 100 nM significantly blocked the SARS-CoV-2-PE spike protein binding to A549 lung epithelial cells by greater than 99%, whereas K5 at 500 nM blocked the SARS-CoV-2-PE spike protein binding to A549 lung epithelial cells around 70%. These results indicate that GRP78 is important for SARS-CoV-2 virus binding to A549 lung epithelial cells.

Binding Inhibition Examples #3

GRP78 Inhibitors Kr1Fc and K5 Inhibit SARS-CoV-2 Spike Protein Binding to VERO Cells at 37 C.

This invention examines if N-terminal GRP78 inhibitors could block the binding of SARS-CoV-2 spike protein on VERO monkey epithelial kidney cells. VERO cells are known to have high expression of the SARS-CoV-2 receptor, ACE2, and as such are very susceptible to SARS-CoV-2 virus infection. This invention teaches that both pre-incubation of VERO cells with GRP78 inhibitors and also by adding GRP78 inhibitors at the same time as the SARS-CoV-2 spike protein results in significant and potent inhibition of spike protein binding. VERO cells (50,000/100 uL) in PBS were added to Eppendorf tubes. Either Kr1Fc at 100 nM or K5 at 500 nM were added to half of the tubes of VERO cells for a pre-incubation time of 6 hrs. before 50 nM PE-labeled SARS-CoV-2 spike protein was added. In the other half of the tubes with cells, the PE-labeled SARS-CoV-2 spike protein was added at the same time as the GRP78 inhibitors listed above. The tubes of cells were incubated at 37 C with mild shaking. After 24 hours, the cells were spun and washed twice with PBS. Fresh PBS was added to the cells and flow cytometry analysis of PE-labeled SARS-CoV-2 spike protein bound to VERO cells was detected on a Guava PCA flow cytometer. In this invention GRP78 inhibitors Kr1Fc and K5, displayed inhibition of SARS-CoV-2 spike protein binding with both a 6-hour pre-incubation or no pre-incubation with GRP78 inhibitors (FIGS. 6 & 7). Kr1Fc at 100 nM displayed greater than 90% inhibition of SARS-CoV-2 spike protein binding to VERO cells. K5 at 500 nM displayed an >80% inhibition of SARS-CoV-2 spike protein binding to VERO cells. The pre-incubation of GRP78 inhibitors on VERO cells leads to increased inhibition of SARS-CoV-2 binding.

Internalization of Surface-Bound GRP78 Example #4

Surface-Bound GRP78 is Significantly Decreased after Kr1Fc and K5 Treatment.

In this invention, Kr1FC (100 nM), and K5 (500 nM) were added separately to Eppendorf tubes containing either 50,000 A549 cells or 50,000 VERO cells in triplicate. The cells and GRP78 inhibitors were incubated at 37 C for 24 hours. The cells were pelleted by centrifugation and washed twice with PBS. Anti-GRP78 monoclonal antibody labeled with PE (1 mg/ml) was then added at 1 ul per tube. A negative control of a human IgG1-PE antibody was also added to a tube of untreated cells. After 1 hour incubation of the anti-GRP78-PE antibody at room temperature, cells were washed twice with PBS and analyzed for surface-bound GRP78 by a Guava flow cytometer. FIG. 8 demonstrates that the treatment of VERO cells with GRP78 inhibitors, Kr1Fc and K5, significantly reduced the expression of GRP78 on the surface of the cells. FIG. 9 shows that treatment of A549 lung cells with GRP78 inhibitors, Kr1Fc and K5 significantly reduced the concentration of surface-bound GRP78 by greater than 80%. Comparing the expression of surface-bound GRP78 on A549 and VERO cells, it is clear the VERO cells have a much higher level of surface-bound GRP78. Since these cells are more receptive for viral infection, this invention and data show that it is not only the levels of surface ACE2 but also GRP78 that is important for infectivity. Because these GRP78 inhibitors reduce the surface-bound GRP78 levels, does this result in the reduction of virus binding only or is GRP78 also responsible for internalization of SARS-CoV-2 spike virus.

Internalization Inhibition Example #5

Kr1Fc and K5 Inhibit pHrodo-Red Labeled SARS-CoV-2 Spike Protein Internalization in VERO Cells.

This invention examines if surface-bound GRP78 inhibition can inhibit binding of SARS-CoV-2 spike protein and block its internalization. As shown in FIG. 10A, SARS-CoV-2 spike protein was labeled with pHrodo-red dye, which has a weak fluorescence at pH 7 (cell surface), but has a strong fluorescence at pH 4 (inside cell) allowing for the detection of spike protein internalization. VERO cells were pre-incubated with GRP78 inhibitor, Kr1Fc and K5 for 6 hrs. After 6 hrs., Rodo-red labeled SARS-CoV-2 spike protein was added to the VERO cells and incubated at 37 C with mild shaking for 24 hrs. Cells were then pelleted, washed twice and flow cytometry analysis was performed on a Guava PCA flow cytometer to detect inhibition of internalized spike protein. In FIG. 10B, this invention shows that Rodo-red labeled SARS-CoV-2 spike protein is internalized in about 52% of VERO cells in 48 hrs. at 37 C. When VERO cells are pre-incubated with the GRP78 inhibitor, Kr1Fc, or K5 the internalization of Rodo-red labeled SARS-CoV-2 spike protein is significantly inhibited by 90-95% similar to the Rodo-red labeled IgG1 antibody negative control. In both examples, A549 and VERO cells GRP78 inhibitors prevent SARS-CoV-2 spike protein internalization.

Whole SARS-CoV-2 Virus Neutralization Example #6

GRP78 Inhibitors, Kr1Fc and K5, Neutralize SARS-CoV-2 Pseudotyped Virus Infection of VERO Cells.

In this invention, modified SARS-CoV-2 virus assay was performed by IBT Bioservices (Rockville, MD). In this assay, a SARS-CoV-2 pseudotyped virus was generated by replacing the replication RNA piece from the SARS-CoV-2 virus with RNA encoding the Luciferase enzyme protein for detection. The remaining structural proteins (spike protein, envelope protein, and matrix protein and nucleocapsid protein) were left intact. This allows for SARS-CoV-2 (rVSV-SARS-CoV-2 (D614G)) pseudotyped virus to attach and internalize but not replicate. The invention teaches that Kr1Fc and K5 can prevent the full SARS-CoV-2 pseudotyped virus from attaching and entry into VERO cells. In FIG. 11A, two compounds demonstrate potent activity with IC50 values of 3.5 uM for Kr1Fc, and 47.4 uM for K5. The assay was performed by using eight dilutions from 0.5 nM to 500 uM for K5 and 0.01 nM to 62 uM for Kr1Fc. These dilutions were added to triplicate wells in a 96 well plate with VERO cells ($1 \times 10^5$ cells per well). Wells in accordance with the invention are infected with SARS-CoV-2 pseudotyped virus at 25,000-35,000 Relative Light Units in each well. Plates were incubated for 24 hours, and attached cells were washed and then each well was read for Luciferase activity using Bright-Glo Assay System Kit (Promega). The toxicity of the test compounds was also determined in parallel against VERO cells without virus (FIG. 10B). The 50% and 90% effective neutralization concentration (IC50, IC90) and 50% cell death concentration (cytotoxic, CC50) values are calculated by regression analysis to demonstrate efficacy. The selectivity index (SI90) (CC90 divided by IC90), which is indicative of the safety window between cytotoxicity and antiviral activity for 1 log inhibition was calculated and presented in FIG. 17. The higher the SI90 value, the more effective and safer the inhibitor.

Immune Suppression Inhibition Example #7

Figure 12:
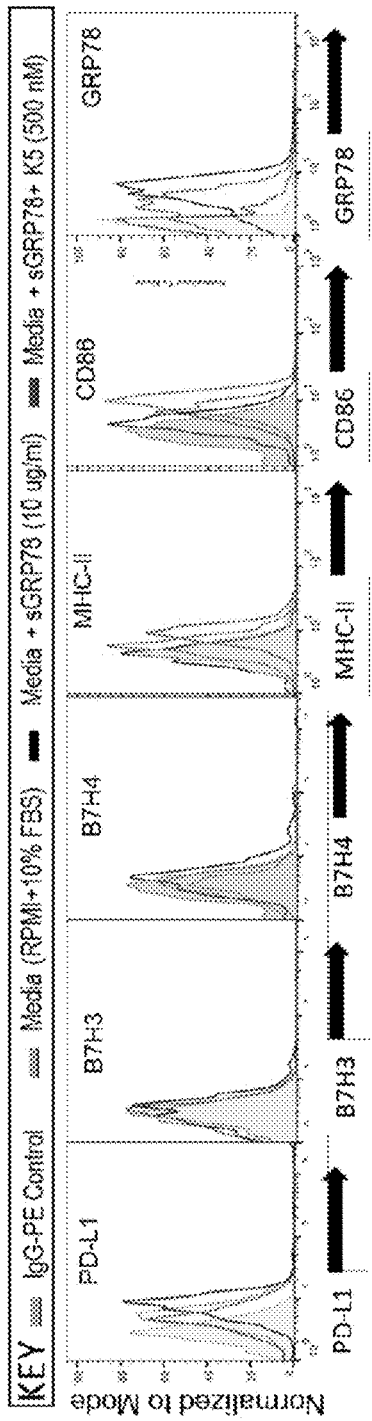
FIG. 12 A is a series of graphs which illustrate that K5 significantly augments co-inhibitory (PD-L1, B7H4) checkpoint protein and co-stimulatory (CD86, MHC-II) protein expressions induced by soluble GRP78 on A549 lung cells.
Figure 12:
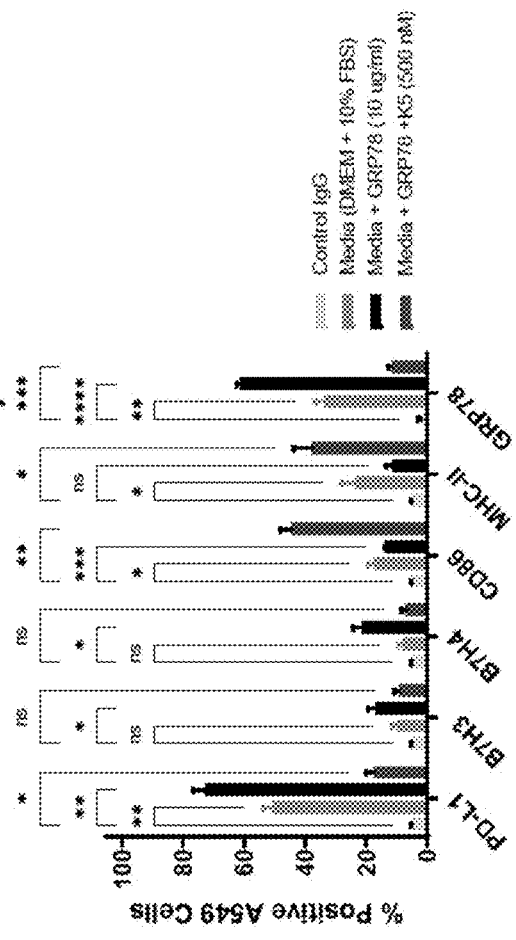

Kr1Fc, K5Fc and K5 reverses immune suppressive phenotype on adenocarcinoma alveolar lung epithelial cells (A549) induced by sGRP78 binding. This invention addresses whether soluble and surface bound GRP78, which has been shown to be stimulated during viral infections would augment checkpoint protein expression on lung cells similar to what has been reported with dendritic cells. To determine this, sGRP78 (5 ug/ml) was added to A549 cells and grown for 3 days±Kr1Fc at 37 C/5% C02. After 3 days, cells were fixed (not permeabilized), stained with fluorescently labeled antibodies and flow cytometry analysis was performed on co-inhibitor checkpoint proteins, PD-L1, B7H3, B7H4 and co-stimulatory proteins MHC-II, CD86. The present invention examines the expression of surface GRP78 with and without Kr1Fc, K5Fc and K5 inhibitors. We chose a concentration of 5 ug/ml sGRP78 because it has been shown that sGRP78 circulates in cancer and Rheumatoid Arthritis patients around this concentration. FIGS. 12 and 13 show that sGRP78 induced a significant increase in expression of immune inhibitory checkpoint proteins PD-L1, B7H3, B7H4 and decreased expression of immune stimulatory proteins MHC-II and CD86 on A549 cells. Kr1Fc and K5 completely reversed this immune-suppressive phenotype.

Cytokine Expression Inhibition Example #8

Previously, we have shown that soluble GRP78 induces cytokine expression on tumor cells. In many ways, viral infection mimics the tumor microenvironment, as such we determined that soluble GRP78 could up regulate expression of IL10 and IL6 on A549 lung cells. In FIG. 14, we now show that Kr1Fc and K5 inhibit soluble GRP78 induced cytokine expression of IL10 and IL6 from A549 lung cells. A549 cells (50,000) were added to Eppendorf tubes in full DMEM media. In half the tubes, soluble GRP78 (5 ug/ml) was added along with either K5 (500 nM) or Kr1Fc (100 nM). An IgG human antibody was used as a negative control. After incubation for 3 days at 37 C with mild shaking, the cells were spun down and the supernatant was tested using either an IL10 or IL6 ELISA assay kits (R&D Systems). The protocol for each kit was followed per manufacturer instructions and pg/ml of each cytokine at each condition on A549 cells with and with GRP78 inhibitors was calculated from standard curves. A significant and dose dependent inhibition of cytokines expression from A549 cells was observed with Kr1FC and K5 GRP78 inhibitors.

Plasminogen Activation Inhibition Example #9

Kr1Fc and K5 Block the Hyperfibrinolysis Induced by Plasmin Formation.

Figure 15:
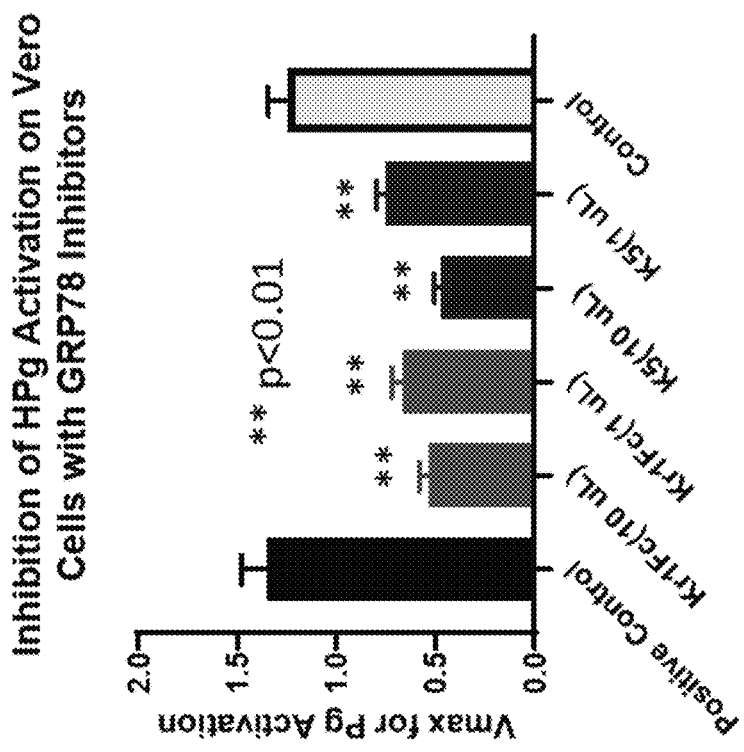
FIG. 15 A is a schematic that shows that Kr1Fc (SEQ ID NO: 20) and K5 (SEQ ID NO: 1) inhibit the activation of human plasminogen on VERO cell surfaces.
Figure 15:
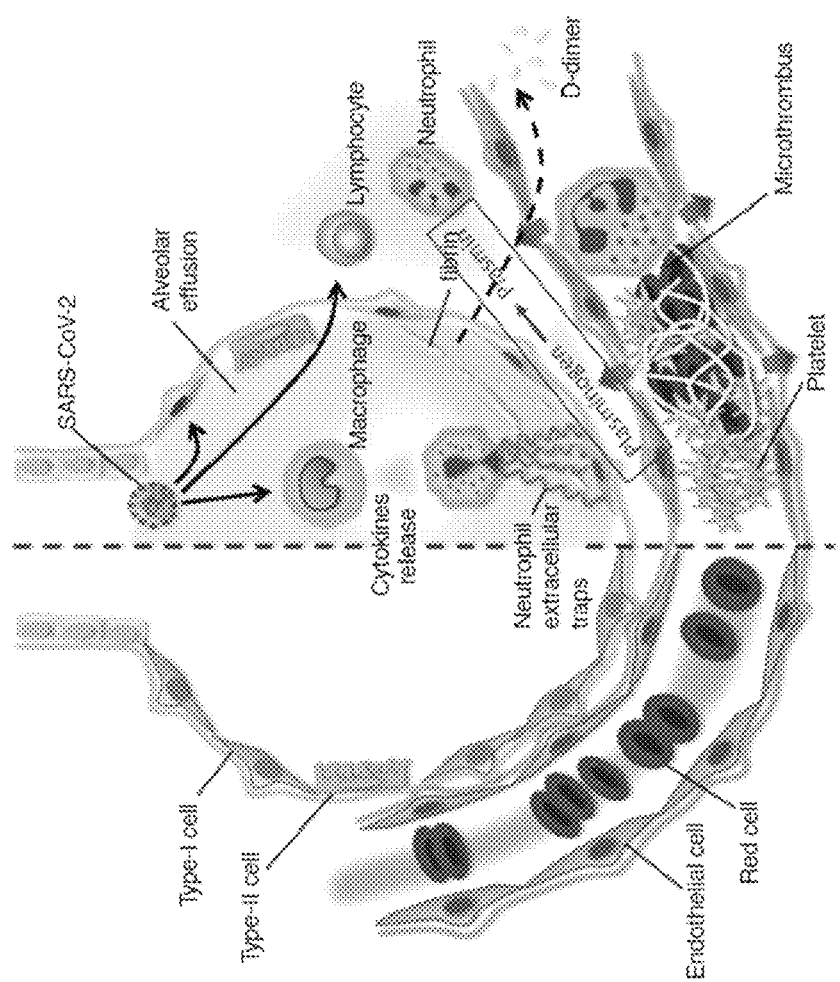

People with diabetes, hypertension, lung cancer and heart disease have a higher risk of being infected by SARS-CoV-2 virus and a greater chance of dying. The leading causes of death from COVID-19 is hemorrhage or bleeding disorders and that one of the characteristics of the disease is overactivity of the system responsible for removing blood clots (hyperfibrinolysis). This aberrant coagulopathy is caused by elevated levels of plasminogen leading to plasmin. Recent publications show that in all of the comorbidities that cause worse outcomes for people with COVID-19, elevated levels of plasmin have been found to be a common factor. Plasminogen normally circulates in blood as an inactive protein. Once an injury or a lesion occurs (FIG. 2, FIG. 15A (red)), plasminogen is activated to its active form called plasmin. Plasmin then dissolves blood clots at the lesions by clipping fibrinogen resulting in fibrinogen fragments called D-dimers. More than 97% of people hospitalized with severe COVID-19 have increased levels of D-dimer. D-dimer levels are associated with the amount of virus detected in the body and continue to rise as the severity of COVID-19 increases. In COVID-19 survivors, D-dimer levels decreased to control levels. Higher-than-normal levels of plasmin and D-dimers can lead to severe bleeding. Several publications have shown that plasminogen binds to surface-bound GRP78 through one of its kringle domains, kringle 5 (K5). In fact, GRP78 binding to plasminogen increases its rate of activation to plasmin significantly. Since our GRP78 inhibitors, Kr1Fc, K5Fc and K5, consists of the plasminogen K5 kringle domain or a similar kringle domain (Kr1), we can show that these inhibitors significantly decrease the activation of plasminogen to plasmin on lung cells by over 70% (FIG. 15). This decrease in plasmin formation should result in reduced hyperfibrinolysis and D-dimer formation reducing the bleeding disorders observed in severe COVID-19 patients.

Safety Profile Example #9

Kr1Fc, and K5 Show No Adverse Binding to Receptors and Ion Channel Proteins or Toxicity on Primary Human Cells.

To identify possible toxicities, a receptor binding profile assay with 75 receptor and ion channels, and a cytotoxicity assay with 5 human primary cell lines (validated from single donor sources) with Kr1 Fc (10 uM) or K5 (100 uM) were determined by CEREP/Eurofins. No specific binding or toxicity was observed, indicating that Kr1Fc exhibits a safe, selective biochemical profile and is unlikely to have adverse effects in vivo.

Safety Profile Example #10

No Weight Loses or Overt Toxicity was Observed in Mice Treated GRP78 Inhibitors Kr1Fc and K5 at 60 mg/kg and 90 mg/kg Respectively.

This invention examines the toxicity of GRP78 inhibitors Kr1Fc and K5 in BALB/c mice 8 weeks old. Three groups of mice were dosed intraperitoneal (i.p.) in a volume of 10 mL/kg scaled to the body weight of each individual animal. Treatment groups were as follows:
  Group 1 received vehicle (PBS pH 7.2).
  Group 2 received Kr1Fc at 60 mg/kg, i.p., every other day (qod) until day 26.
  Group 3 received K5 at 90 mg/kg every other day (qod) until day 26.

Animals were weighed daily on Days 1-5, and then twice weekly until day 26. The mice were observed frequently for overt signs of any adverse, treatment-related (TR) side effects, and clinical signs were recorded when observed. Individual body weight was monitored as per protocol, and any animal with weight loss exceeding 30% for one measurement or exceeding 25% for three consecutive measurements was euthanized as a TR death. Group mean body weight loss was also monitored according to Charles River Discovery Services protocol. Acceptable toxicity was defined as a group mean body weight (BW) loss of less than 20% during the study and no more than 10% TR deaths. Deaths were classified as TR if it was attributable to treatment side effects as evidenced by clinical signs and/or necropsy.

Figure 16:
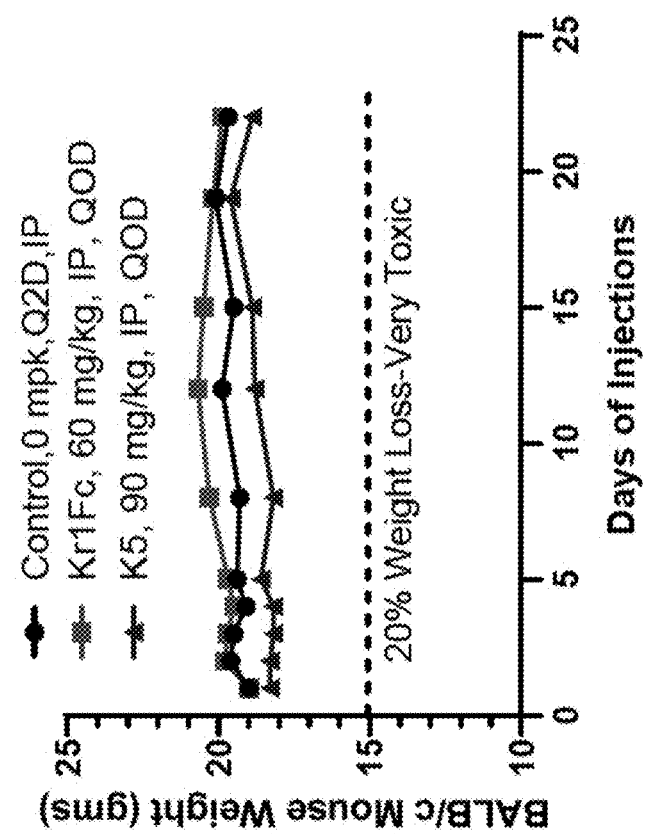
FIG. 16 is a graph that shows the mice treated with Kr1Fc (SEQ ID NO: 20) (60 mg/kg) or K5 (SEQ ID NO: 1) (90 mg/kg) every other day, intraperitoneally displayed no weight loses or overt toxicity.

FIG. 16 shows that Kr1Fc and K5 showed no overt toxicity or weight loss in mice dosed as listed above. These results support the CEREP/Eurofins in vitro toxicity testing from above and suggest that the invention listed types of GRP78 inhibitors will be safe, with low toxicity in clinical studies.

Chemistry, Manufacturing, and Controls (CMC) Aspects for the Development of K5Fc, K5 and Kr1Fc.

According to the invention the practitioner will express and purify Kr1Fc, K5Fc, K5 and perform CMC assays to validate the purity, potency, and efficacy of Kr1Fc, K5Fc and K5 lots for in vitro and in vivo SARS-CoV-2 virus inhibition studies. Currently, Kr1Fc, K5Fc and K5 are transiently expressed in Expi293 and ExpiCHO cells. Mammalian cell expression is necessary due to the need for a correctly folded kringle domains and glycosylation of the Fc domain. In accordance with the invention stable CHO clones expressing Kr1Fc, K5Fc and K5 will be created and banked, for regulatory filing. In accordance with the invention a practitioner will validate assays for purity, potency and identity of lots of Kr1Fc, K5Fc and K5. To validate Kr1Fc's, K5Fc's and K5's lot-to-lot quality, a negative control of denatured Kr1Fc and a positive standard lot of Kr1Fc are banked and used in each assay for comparisons.

Statistical Analysis:

In accordance with the invention assays in Chemistry, Manufacturing, and Controls (CMC) aspects are run in triplicate on two separate occasions by two different investigators. The average mean value for absorbance, density and EC50 values plus the standard deviation are calculated for all assays. Any compound lot that is significantly ($p<0.05$, by student's two-tailed t-test assuming normal distribution and equal variance) different than our control standard lot will not be used for further testing.

Lot to Lot Purity, Potency and Variability:

According to the invention the purity for Kr1Fc, K5Fc and K5 lots are determined by practicing 280 nm OD measurements for drug concentration, densitometry analysis (GelQuant) of Coomassie-stained SDSPAGE gels for drug purity and mass spectrometry analysis (fee for service) for drug quality. These assays are used to ensure the desired quality of Kr1Fc is maintained. For all in vitro studies, negative controls are Kr1Fc mixed with denatured, dead Kr1Fc at various ratios (10% to 90%) to define the limits of each assay and for a positive control, a master lot of Kr1Fc is set aside for comparison in all assays between different lots.

According to the invention the potency of Kr1Fc, K5Fc and K5 lots are determined using a direct binding ELISA assay between Kr1Fc, or K5Fc, or K5 and GRP78. Full-length his-tagged GRP78 (StressMart) at 100 nM in PBS is attached to nickel-coated 96 well plates (Pierce). Various concentrations of inhibitors between 0.5 to 50 nM are bound at 4 C. Plates are blocked with 10% BSA and washed with PBS containing 0.05% Tween®-20 detergent per manufacturer's instructions (Pierce). Finally, a mouse anti-human Fc HRP-labeled antibody is added, and detection of bound Kr1Fc, K5Fc or K5 is assessed with the TMB ELISA (Sigma) reagent. A secondary binding assay for Kr1Fc, K5Fc, and K5 lots are performed measuring Kr1Fc competition binding between SARS-COV-2 spike proteins and GRP78, as was described in our results (FIG. 4).

According to the invention functional efficacy of Kr1Fc lots is determined by examining immune co-inhibitory checkpoint (PD-L1, B7H3, B7H4) and immune co-stimulatory (CD86, MHC-II) protein expression. As described in FIG. 5, sGRP78 (5 ug/ml) are added to lung epithelial adenocarcinoma A549 cells and grown for 3 days+Kr1Fc at 37 C/5% C02. After 3 days, cells are removed by Versene, fixed, and then stained with fluorescently labeled antibodies and flow cytometry analysis are performed.

Assays that have a signal-to-noise ratio greater than two-fold and are able to detect >10% impurities, and assays with <200 nM EC(50) values for potency and functional assays are considered valid.

With respect to drug purity and identity, mass spectrometry can detect impurities below 5% reliably. The two-fold signal-to-noise requirement has been met for all assays except the functional checkpoint protein expression assays. An alternate approach is to test for protein phosphorylation in signaling pathways with A549 cells using Kr1Fc. Protein phosphorylation assays with signaling pathways through PI3K, SMAD2/3, STAT3 are known in the prior art. These signaling pathway assays lead to a rapid and accurate method to test for activity and functionality in lots of Kr1Fc.

According to the invention efficacy of GRP78 inhibitors, Kr1Fc, K5Fc, and K5, for blocking SARS-CoV-2 spike protein binding and internalization effects on lung epithelial A549 and VERO cells has been determined and validated.

The disclosed Kr1Fc, K5Fc and K5 inhibitors potently block binding of the SARS-CoV-2 spike protein to GPR78 (FIG. 4A). Much like tumors, viral infections create an inflammatory, immune evasive microenvironment. The references incorporated by reference shows that stressed cells relocate GRP78 to cell surfaces. Surface-bound GRP78 induces immune suppression by up regulating expression of co-inhibitory checkpoint proteins and down regulating expression of co-stimulatory proteins. GRP78 also increases the expression of inflammatory cytokines like IL-10, and IL-6. By blocking GRP78's activity and binding on lung, kidney epithelial and endothelial cell surfaces with our GRP78 inhibitors, one practicing the invention can completely reverse the immune suppressive, inflammatory nature of human alveolar lung epithelial adenocarcinoma A549 cells, VERO epithelial and endothelial cells. In addition, studies show that the blocking of the N-terminal domain of GRP78 reduces the attachment, entry and replication of several types of viruses including betacoronaviruses. As such, we show in these studies that our GRP78 inhibitors, which bind to the N-terminal domain of GRP78, will produce similar effects as siRNA or an N-terminal GRP78 antibody against the SARS-CoV-2 virus.

According to the invention neutralization activity against full pseudotyped SARS-CoV-2 virus (rVSV-SARS-CoV-2 (D614G)) of Kr1Fc and K5 are able to prevent the virus from attaching and entry into VERO cells grown in culture. Two compounds demonstrate potent activity with IC(50) values of 3.448 uM for Kr1Fc, and 47.35 for K5. Eight dilutions from 0.5 nM to 500 uM for K5 and 0.01 nM to 62 uM for Kr1Fc were added to triplicate wells with cells. Wells in accordance with the invention are infected with SARS-CoV2 pseudotyped virus at 25,000-35,000 Relative Light Units to each well. Plates were incubated for 24 hours, attached cells were washed and then each well was read for Luciferase activity using Bright-Glo Assay System Kit (Promega). The toxicity of the test compound was also determined in parallel against VERO cells without virus. The 50% and 90% effective neutralization concentration (IC50, IC90) and 50% cell death concentration (cytotoxic, CC50) values are calculated by regression analysis to demonstrate efficacy. The selectivity index (SI50) (CC50 divided by IC50), which is indicative of the safety window between cytotoxicity and antiviral activity was calculated and presented in Table 1. The higher the SI50 value, the more effective and safer the inhibitor.

In accordance with the invention potent inhibition of virus attachment is demonstrable. GRP78 is surface-bound in stressed and tumor cells, in accordance with the invention the practitioner may add GRP78 to the media of A549 and VERO cells to produce a cell line for virus attachment and internalization. In accordance with the invention K5, K5Fc and Kr1Fc will reduce surface-bound GRP78 by >90%. In accordance with the invention, the reversal of immune suppression, observed with A549 cells treated Kr1Fc, demonstrates a response which could reduce viral pathology in vivo.

In accordance with the invention Kr1Fc will inhibit an adapted SARS coronavirus in an acute respiratory distress syndrome lethal mouse model (BALB/c mice). SARS-COV-2 virus creates a severe acute respiratory syndrome disease that is highly lethal. To date there have been no drugs directly approved for curing betacoronavirus infections. Part of the reason for this is due to the lack of appropriate animal models for drug testing. Researchers are testing multiple animal models in macaques, marmosets, hamsters, cats, and ferrets with SARS viruses but few mimics the SARS-CoV-2 virus pathogenicity. Recently, Day et al. have adapted and characterized a new strain of SARS-CoV (v2163) that targets lungs and is highly lethal in BALB/c mice. This model largely mimics the human COVID-19 disease. Because of the low expense, ease of handling and minimal amount of drug required, this model when practiced in accordance with the invention demonstrates GRP78 inhibitor with a human SARS-CoV virus. Since mouse and human GRP78 are 98% identical, studies of this nature demonstrate Kr1Fc drug will block GRP78's activity in mice as well as humans resulting in a greatly reduced infection of lung cells.

Experiment

In accordance with the invention the anti-viral activity of Kr1Fc and K5 is demonstrated using a mouse adapted strain of the Urbani SARS-CoV called V2163. Half male and half female BALB/c mice are inoculated with 50 uL containing $10^4$ CCID50 (Cell culture infectious dose 50% endpoint) of SARS-CoV-V2163 virus by intranasal (i.n.) delivery. Four groups of mice (10 mice per group) are given 100 mg/kg/day K5, 50 mg/kg/day Kr1Fc, and PBS, pH 7.4 negative control, and a positive control for this model used meeting the standards of the Institution for Antiviral Research. All Kr1Fc and K5 samples are dosed i.p., QD between shoulder blades 16 hours prior to i.n. infection for the next 7 days. Mice are observed daily, and group weights are taken throughout the study. Mice are observed for death up to day 21 post virus exposure. Animals that lose greater than 30% of their initial body weight are humanely euthanized and the day of euthanasia designated as the day of death. Lungs from sacrificed mice are observed for gross pathology and discoloration and assigned a score ranging from 0 (normal appearing lung) to 4 (maximal plum coloration in 100% of lung). Mouse lung samples from each test group are pooled and homogenized in MEM solution and assayed for A) infectious virus using the virus yield assay, B) cytokine analysis (IL-6, IL-1 and IL-10) and immune cell infiltrates (NK, Macrophage, T-cell and DCs). Virus titer, cytokine concentration and immune cell numbers are compared to controls by analysis of variance on log transformed values assuming equal variance and normal distribution. A significant ($p<0.05$) improvement in survival with Kr1Fc or K5 treatment compared to PBS negative control and a significant decrease in viral-induced CPE in the lungs of provides a foundation for further studies.

As described in the references incorporated by reference K5 has a half-life around 20 min and an MTD greater than 660 mg/kg in mice and monkeys. The more potent GRP78 inhibitors, Kr1Fc, and K5Fc in accordance with the invention and publication of proteins with an added Fc domain have improved half-lives and may be advantageous over the individual kringle domains. In addition, combination therapy with an ACE2 inhibitor and our GRP78 inhibitor could demonstrate synergistic effects.

In accordance with the invention, the conclusions described are demonstrated by statistical analysis. More specifically, graph generation and statistical analysis are done on GraphPad Prism 7.0 software. Statistical comparisons are performed two-way ANOVA with Bonferroni posttest by Student's two tailed t-test, assuming normal distribution and equal variance, where differences are considered significant at $p<0.05$. Power analysis with a Wilcoxon-Mann-Whitney test for a two-sided unpaired sample power analysis using the G*Power 3.1.9.4 program is used to determine the number of mice needed. The group size (n=10) is powered to detect decreases of at least 30% in the number of metastases between control and 10 mg/kg Kr1Fc treated-groups, assuming a coefficient of variation equal to 1.5 (as suggested by projected/anticipated data), and using a two-sample t-test for log normal data with 80% power and a significance level of 0.05. Maximum day of death (MDD), cytokine values, and gross lung scores are analyzed by Mann-Whitney pairwise comparisons or the Kruskal-Wallis test followed by Dunn's multiple comparison test as applicable. Raw survival numbers are compared by the Fisher exact test. Survivor curve analysis are done using the Kaplan-Meier method and a log rank test. When that analysis revealed significant differences among the treatment groups, pairwise comparisons of survivor curves are analyzed by the Gehan-Breslow-Wilcoxon test, and the relative significance adjusted to a Bonferroni-corrected significance threshold for the number of treatment comparisons made. Differences in percent weight loss are tested by one-way ANOVA with Newman-Keuls multiple comparison test, assuming equal variance and normal distribution. For lung titer data, we will perform a K5 test for normality, then use non-parametric Kruskal-Wallis test with Dunn's multiple comparison test for groups that are not normally distributed, and a one-way ANOVA with Newman-Keuls multiple comparison test for groups that are normally distributed.

DETAILED DESCRIPTION OF THE FIGURES

Figure 2:
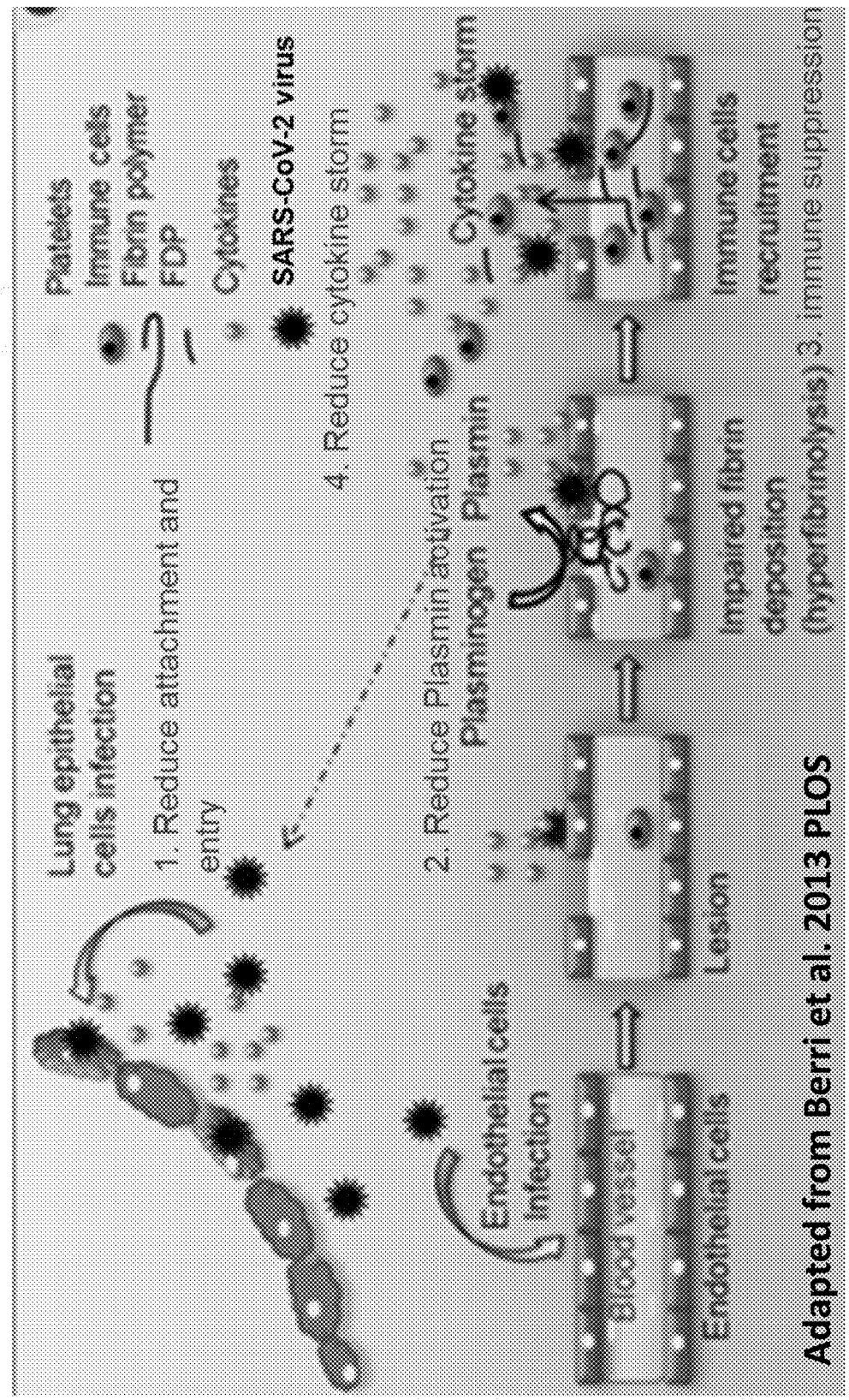
FIG. 2 is a schematic of SARS-CoV-2 virus inhibition by our novel class of GRP78 inhibitors.

FIG. 1 are schematics of SARS-CoV-2 virus attachment, entry and replication with and without GRP78 inhibitors. FIG. 1A shows stress induces GRP78 to translocate to the cell surface. 1) SARS-CoV-2 virus attaches to GRP78 and ACE2. 2) GRP78 enhances SARS-CoV-2 virus entry into the lung epithelial cells. 3) GRP78 increases replication and secretion of SARS-CoV-2. FIG. 1 B shows GRP78 inhibitors blocks a significant amount of SARS-CoV-2 virus binding and reduces surface-expression of GRP78, which then leads to a reduced amount of SARS-CoV-2 virus entry into the cells. Finally, the lack of GRP78 on cell surfaces inhibits SARS-CoV-2 virus attachment, internalization and replication. The X indicates that blocking GRP78 binding on the cell surface blocks viral replication FIG. 2 is a schematic of SARS-CoV-2 virus inhibition by our class of GRP78 inhibitors. This invention shows that N-terminal GRP78 inhibitors block 1) SARS-CoV-2 virus attachment and entry, 2) reduces hyperfibrinolysis by blocking the conversion of plasminogen to plasmin on lung cell surfaces, 3) reverses immune suppression by reducing checkpoint protein expression on lung and endothelial cells and 4) reduces the virus induced cytokine storm by reducing IL10 and IL6 cytokine expression.

FIG. 3 is an analysis of Kr1Fc, K5Fc, Kr1 and K5 Proteins Purity, Structure and Binding. FIG. 3 A-D are image of SDS-PAGE analysis showing A) Kr1Fc, B) K5Fc, C) Cr1 and D) K5 proteins expressed in 293F HEK cells. Kringle proteins were purified by either protein A-agarose or benzamidine-agarose. Lane markers are Mw: Protein marker, Lane 1: Reducing conditions, Lane 2: Nonreducing conditions, M: expression media, F: flow through, W: wash, P: purified protein. A FIG. 3 E is a graphic depiction of Kr1-Fc and K5Fc fusion proteins with 2 kringle domains fused to a human IgG1 Fc domain. A FIG. 3 F is a schematic illustration of human GRP78 regions where published GRP78 protein inhibitors and the invention proteins interact. Known and predicted binding sites of viruses to GRP78 protein are shown underneath the GRP78 schematic. (ATPase domain SBD: substrate binding domain, KDEL; 4 residue C-terminal peptide).

FIG. 4 shows that N-terminal GRP78 inhibitors block binding of GRP78 to SARS-CoV-2 spike protein. FIG. 4 A is a Schematic of a binding assay with full-length SARS-CoV-2 spike protein, HRP-labeled GRP78 and GRP78 inhibitors in a 96 well plate. FIG. 4 B is a graph showing data that N-terminal GRP78 inhibitors, Kr1Fc, K5Fc, and K5 can potently block GRP78 binding to SARS-CoV-2 spike protein. Full length SARS-CoV-2 spike protein was bound to a 96 well plate overnight at 4 C. After blocking and washing, HPR-labeled GRP78 and various concentrations of Kr1Fc, K5Fc, K5 and a negative control, unfolded Kr1Fc were added to plates and incubated for 2 hrs. Wells were washed and TMB reagent was added and absorbance measured by manufactures protocol. Each point is an average of triplicate wells.

FIG. 5 shows that GRP78 inhibitors block binding of PE-labeled SARS-CoV-2 spike protein to A549 lung cells. SARS-CoV-2 spike protein-PE (50 nM) was added to 50,000 A549 lung cells with and without Kr1Fc (100 nM) or K5 (500 nM). Cells were incubated overnight at 4 C to block internalization of the SARS-CoV-2 spike protein-PE. Cells were washed 2× with PBS and run on a Guava PCA flow cytometer. Control was a human IgG1-PE Ab. FIG. 5 A shows Raw flow cytometry plots and FIG. 5 B is a histogram overlay analysis of A549 cells with bound SARS-CoV-2 spike protein-PE competed with GRP78 inhibitors demonstrate that Kr1Fc and K5 block SARS-CoV-2 spike protein-PE binding to A549 lung cells by over 99% and 65% respectively.

FIG. 6 shows that GRP78 inhibitors prevent SARS-CoV-2 spike protein-PE binding to VERO cells. VERO cells were used due to their high expression of ACE2 and their ability to be very susceptible to SARS-CoV-2 virus infectivity. SARS-CoV-2 spike protein-PE (50 nM) was added to 50,000 VERO kidney cells with and without Kr1Fc (100 nM) or K5 (500 nM). Cells were incubated overnight at 37 C. Cells were then washed 2× with PBS and run on a Guava PCA flow cytometer. Control was a human IgG1-PE Ab. FIG. 6 A is dot blot flow cytometry analysis and FIG. 6B is a histogram overlay of VERO cells that bound SARS-CoV-2 spike protein-PE with and without Kr1Fc and K5. From the data it is clear that Kr1Fc (100 nM) and K5 (500 nM) significantly reduced the binding of SARS-CoV-2 spike protein-PE to the surface of VERO cells by about 50%.

FIG. 7 shows that Kr1Fc and K5 prevent binding of SARS-CoV-2 spike protein either with preincubation with VERO cells or added at the same time as the spike protein (FIG. 6). FIG. 7A shows dot blot flow cytometry analysis and histogram overlay analysis of SARS-CoV-2 spike protein-PE (50 nM) binding to VERO cells preincubated with or without Kr1Fc (100 nM) or K5 (500 nM) for 6 hours. The inhibition of SARS-CoV-2 spike protein-PE binding was greater than 60% with Kr1 or K5 preincubation. These data suggest that preincubation of cells with GRP78 inhibitors may reduce spike protein binding slightly better.

FIG. 8 demonstrates that N-terminal GRP78 inhibitors reduce the expression of surface-bound GRP78 on VERO cells. To help define if our GRP78 inhibitors simply block the binding to SARS-CoV-2 spike protein to GRP78 or actually remove GRP78 from the cell surface, resulting in less surface-bound GRP78 for spike protein binding and internalization, we measured the amount of surface-bound GRP78 on VERO cells after Kr1Fc (100 nM) and K5 (500 nM) treatment. FIG. 8 A shows Flow cytometry analysis of VERO cells surface-bound GRP78 using a C-terminal GRP78 antibody-PE. This antibody has not been shown to inhibit SARS-CoV-2 spike protein binding. FIG. 8B shows the flow cytometry dot blot and histogram overlay analyses Kr1Fc and K5 produce a greater than 50% decrease in surface-bound GRP78. This suggests that these N-terminal GRP78 inhibitors may internalize/remove GRP78 from VERO cell surfaces resulting in less binding sites for SARS-CoV-2 spike protein binding.

FIG. 9 demonstrates that N-terminal GRP78 inhibitors reduce the expression of surface-bound GRP78 on A549 lung cells. To help define if our GRP78 inhibitors can internalize/remove GRP78 from A549 lung cell surfaces like VERO cells, we measured the amount of surface-bound GRP78 on A549 cells after Kr1Fc (100 nM) and K5 (500 nM) treatment. FIG. 9 A shows flow cytometry analysis of A549 cells surface-bound GRP78 shows a much lower expression of surface-bound GRP78 than VERO cells. Again, suggesting why VERO cells may be much more susceptible to infection than A549 cells. FIG. 9 B shows the flow cytometry dot blot and histogram overlay analyses, Kr1Fc and K5 produce a decrease in surface-bound GRP78 from 84% to 60% respectfully. This suggests that these N-terminal GRP78 inhibitors may internalize/remove GRP78 from A540 and VERO cell surfaces resulting in less binding sites for SARS-CoV-2 spike protein binding.

FIG. 10 shows that surface-bound GRP78 expression on VERO cells, which is significantly reduced by Kr1Fc and K5, is essential for SARS-CoV-2 spike protein internalization. In FIG. 10 A, an assay, a pHrodo red dye was used to label SARS-CoV-2 spike protein to measure internalization. pHrodo dyes have a weak fluorescence at pH 7 (outside or bound to cells) but have a strong fluorescence inside the cell at a pH around 5.5 to 4.5. This allows for the measurement of internalization of the pHrodo red-labeled SARS-CoV-2 spike protein on VERO cells. FIG. 10 B shows flow cytometry analysis of SARS-CoV-2 spike protein-pHrodo internalization on VERO cells with and without Kr1Fc and K5. From the dot blot analysis and the FIG. 10 C histogram overlay plots, Kr1Fc (100 nM) and K5 (500 nM) significantly reduce the internalization of SARS-CoV-2 spike protein-pHrodo by over 95% in VERO cells.

Figure 11:
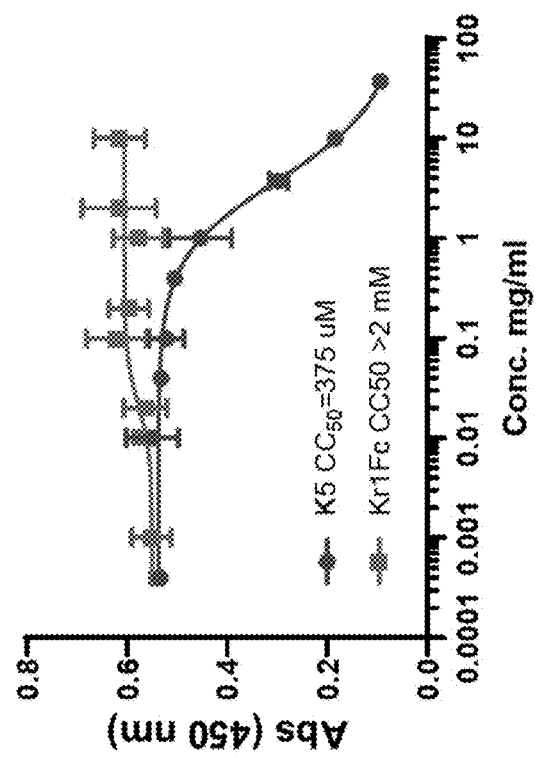
FIG. 11 A is a graph that demonstrates that GRP78 inhibition with N-terminal GRP78 binding proteins, Kr1Fc (SEQ ID NO: 20) and K5 (SEQ ID NO: 1), potently and significantly inhibit whole SARS-CoV-2 pseudotyped virus attachment and internalization on VERO cells.
Figure 11:
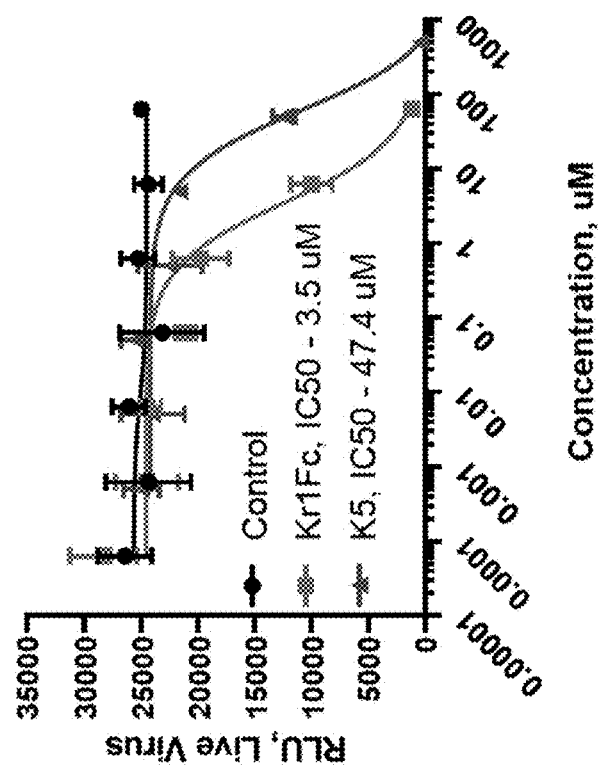

FIG. 11 demonstrates that GRP78 inhibition with N-terminal GRP78 binding proteins, Kr1Fc and K5, potently and significantly inhibit whole SARS-CoV-2 pseudotyped virus attachment and internalization on VERO cells. In this invention, modified SARS-CoV-2 virus assay was performed by IBT Bioservices (Rockville, MD). In this assay, a SARS-CoV-2 pseudotyped virus was generated by replacing the replication RNA piece from the SARS-CoV-2 virus with RNA encoding the Luciferase enzyme protein for detection. The remaining structural proteins (spike protein, envelope protein, and matrix protein and nucleocapsid protein) were left intact. This allows for SARS-CoV-2 (rVSV-SARS-CoV-2 (D614G)) pseudotyped virus to attach and internalize but not replicate. The invention teaches that Kr1Fc and K5 can inhibit the full SARS-CoV-2 pseudotyped virus from attaching and entry into VERO cells. FIG. 11 A shows potent, dose dependent and complete neutralization (99.9%) of SARS-CoV-2 pseudotyped virus infectivity with $IC_{50}$ values of 3.5 uM for Kr1 Fc, and 47.4 uM for K5 was observed. The assay was performed by using eight dilutions from 0.5 nM to 500 uM for K5 and 0.01 nM to 62 uM for Kr1Fc. These dilutions were added to triplicate wells in a 96 well plate with VERO cells ($1\times10^5$ cells per well). Wells in accordance with the invention are infected with SARS-CoV-2 pseudotyped virus at 25,000-35,000 Relative Light Units in each well. Plates were incubated for 24 hours, and attached cells were washed and then each well was read for Luciferase activity using Bright-Glo Assay System Kit (Promega). As shown in FIG. 11 B the toxicity of the test compounds was also determined in parallel against VERO cells without virus. Kr1Fc displayed no cellular toxicity up to 2 mM and K5 inhibited VERO cells growth at a cytotoxic cell concentration at 50% ($CC_{50}$) of 375 uM. These toxicity numbers are at least 10-fold higher than the virus inhibition concentrations indicating toxicity is not the mechanism of action for virus attachment and entry inhibition.

FIGS. 12 A and B illustrate K5 significantly augments co-inhibitory (PD-L1, B7H4) checkpoint protein and co-stimulatory (CD86, MHC-II) protein expressions induced by soluble GRP78 on A549 lung cells. Flow cytometry histogram plots of checkpoint protein expression+/−sGRP78 (5 ug/m) and K5 (500 nM). A549 cells were incubated for 3 days+/−sGRP78 (5 ug/ml) and K5 (500 nM). The cells were then fixed and stained with fluorescently labeled antibodies as indicated and FACs analysis was performed on a Guava PCA. All antibodies were mouse anti-human and PE labeled. A mouse IgG-PE antibody (grey) was used as a negative control. Average of 3 independent analyses with different A549 cell split numbers between 5-10 were used. ns: not significant, *$p<0.05$, $p<0.01$, *$p<0.005$, ****$p<0.001$. Unless otherwise explained in context, asterisks "*" correspond to those in the figures.

FIGS. 13 A and B show that Kr1Fc significantly augments expression of co-inhibitory (PD-L1, B7H4) checkpoint protein and co-stimulatory (CD86, MHC-II) protein expressions induced by soluble GRP78 on A549 lung cells. Flow cytometry histogram plots of checkpoint protein expression+/−sGRP78 (5 ug/m) and Kr1Fc (100 nM). A549 cells were incubated for 3 days+/−sGRP78 (5 ug/ml) and Kr1Fc (100 nM). The cells were then fixed and stained with fluorescently labeled antibodies as indicated and FACs analysis was performed on a Guava PCA. All antibodies were mouse anti-human and PE labeled. A mouse IgG-PE antibody (grey) was used as a negative control. Average of 3 independent analyses with different A549 cell split numbers between 5-10 were used. ns: not significant, *$p<0.05$, $p<0.01$, *$p<0.005$, **$p<0.001$ FIGS. 14 A and B demonstrate that Kr1Fc and K5 inhibit soluble GRP78 induced cytokine expression of IL10 and IL6 from A549 lung cells. A549 cells (50,000) were added to Eppendorf tubes in full DMEM media. In half the tubes, soluble GRP78 (5 ug/ml) was added along with either K5 (500 nM) or Kr1Fc (100 nM). An IgG human antibody was used as a negative control. After incubation for 3 days at 37 C with mild shaking, the cells were spun down and the supernatant was tested using either an IL10 or IL6 ELISA assay kits (R&D Systems). The protocol for each kit was followed and pg/ml of each cytokine for each condition for A549 cells with and with GRP78 inhibitors was calculated from standard curves. Each line is an average of 3 wells. **$p<0.001$ FIG. 15 shows that Kr1Fc and K5 inhibit the activation of human plasminogen on VERO cell surfaces. In FIG. 15 A the schematic of undamaged lung on left side with effective and smooth blood flow. On right side is the damaged lung from SARS-CoV-2 virus infection. The infection causes intense inflammation, and hyperfibrinolysis inducing microthrombi and high levels of D-dimer. The red Plasminogen to plasmin reaction is where the GRP78 inhibitors block the formation of microthrombi and D-dimer by inhibiting cell surface plasmin activation. FIG. 15 B shows significant inhibition of plasmin activation by Kr1 and K5 on VERO cells. In a 96 well plate, VERO cells were added (50,000 per well) and incubated overnight at 37 C, 5% C02. The next day the media was removed and PBS was added to each well. GRP78 inhibitors, Kr1Fc at (100 nM, 10 nM) and K5 at (500 nM, 50 nM) plus human plasminogen (100 ng) was then added to each well. Finally, plasmin substrate VAL-Leu-Lys-pNA (S2251) was added to each well per manufactures instructions and the plate was read at 405 nm to measure pNA formation which is proportional to the enzymatic activity of plasmin. As shown in the chart, Kr1Fc and K5 significantly inhibited the Vmax for plasminogen activation on VERO cells.

FIG. 16 shows the mice treated with Kr1Fc (60 mg/kg) or K5 (90 mg/kg) every other day, intraperitoneally displayed no weight loses or overt toxicity. Kr1Fc and K5 were dosed in BALB/c mice 8 weeks old. Three groups of mice were dosed intraperitoneal (i.p.) in a volume of 10 mL/kg scaled to the body weight of each individual animal. Treatment groups were; 1 group treated PBS, i.p. every other day until day 22; 1 group treated with Kr1Fc at 60 mg/kg, i.p., every other day (qod) until day 22; and 1 group received K5 at 90 mg/kg every other day (qod) until day 22. Animals were weighed daily on Days 1-5, and then twice weekly until day 22. The mice were observed frequently for overt signs of any adverse, treatment-related (TR) side effects, and clinical signs were recorded when observed. Individual body weight was monitored as per protocol, and any animal with weight loss exceeding 30% for one measurement or exceeding 25% for three consecutive measurements was euthanized as a TR death. Group mean body weight loss was also monitored according to Charles River Discovery Services protocol. Acceptable toxicity was defined as a group mean body weight (BW) loss of less than 20% during the study and no more than 10% TR deaths. Deaths were classified as TR if it was attributable to treatment side effects as evidenced by clinical signs and/or necropsy. From FIG. 16, it is clear that Kr1Fc and K5 showed no overt toxicity or weight loss in mice dosed as listed above.

FIG. 17 is a table showing GRP78 binding sequences from various viruses' protein domains compared to known GRP78 binding sequences from K5 (binding sequence reflected as SEO ID NO: 190). This comparison of binding sequences identifies viruses that may be inhibited by our method of treatment which occurs through blocking the N-terminal domain of GRP78.

Treatment Parameters when Using the Therapeutic Invention

Severe viral illnesses are a result of exposure, cellular infection and replication of the virus to viral levels that overpower the host's immune system leading to signs and symptoms of disease. Viruses can't make new viruses on their own and require host cells to produce new viruses. With low levels of viral exposure, this typically results in the body's immune system to activate and attack the virus directly prior to symptom development. This results in the virus being eliminated from the host. In people with limited immune response and/or high levels of viral exposure, the host immune system will most likely become overpowered by the viral load and the patient will become ill. Viral infection propagates as the virus attaches to the cell surface at which time it is brought into the cell. Viruses bring in their own DNA or RNA instructions into the cell for replication and their eventual release only to repeat the process in greater numbers again and again increasing the infection rate, which increases the viral load and eventually leading to severe illness.

Viruses are known to have several cellular binding proteins called "spike proteins" on the surface which seek out and attach to the cell surface. For the SARS-CoV and SARS-CoV-2 viruses, this attachment can be to the ACE2 receptor and other accessory receptors like GRP78, which are found on the cell surface of respiratory lung and endothelial cells. These receptors then transport the viral material into the cells where it is replicated and expelled from the infected cells to repeat the process.

Method to Select and Inhibit Viruses with a GRP78 Recognition Site.

Surface bound GRP78 has been reported to be important for attachment and entry into host cells for several different types of viruses. In Elfiky's publication, they predict that coronaviruses SARS-CoV-2, NL63, 229E, OC43, and HKU1 have a similar GRP78 recognition/binding site. Other publications have shown that surface bound GRP78 is important for attachment and entry of Zika virus, Ebola virus, MERS-CoV, Coxsackievirus A9, Dengue virus, Japanese encephalitis virus (JEV) and Influenza viruses but have not examined if they have the same GRP78 binding sequences. From our previous publications, we demonstrated that the sequence from kringle 5 of human plasminogen, CYTTNPRKLYDYC binds tightly to surface bound GRP78.

Although, Elfiky's prediction uses a weaker GRP78 binding sequence, PEP42 (CTVALPGGYVRVC), than the K5 sequence, it still retains some of the important amino acids that we had shown previously for GRP78 binding in the kringle 5 structural fold region. In FIG. 17, we show sequence alignment of viruses compared to our known GRP78 binding kringle sequences to identify possible GRP78 binding sites. Using this alignment, we can predict which viruses will be responsive to our method of treatment for viral inhibition through blocking the N-terminal domain of GRP78. From this alignment, we can now predict that SARS-CoV-2, NL63, 229E, OC43, HKU1, MERS-CoV, EBOLA, Zika, Yellow Fever, West Nile, and Influenza A, B viruses will be inhibited by our therapies due to their GRP78 binding. However, SARS-CoV does not contain the proposed GRP78 binding sequence so we predict that our GRP78 inhibitors would not be effective against this virus. As proof this prediction is accurate, in Example 6, we can show that our N-terminal binding GRP78 inhibitor, Kr1Fc, potently blocks attachment and entry of SARS-CoV-2 pseudoviruses, but we have recently discovered that our GRP78 inhibitor, Kr1Fc, did not block viral induced death or weight loss in mice infected with a lethal variant of SARS-CoV.

Method for Selecting Our Target Population for Prophylactic or Therapeutic Treatment with GRP78 Inhibitors Against SARS-CoV-2 and Other Viruses Infection People under the age of 65 with comorbidities like cancer, obesity, cardiac disease, lung disease, and hypertension, have a higher risk of being infected with SARS-CoV-2 virus than those without a comorbidity. This same group of people also has a much higher rate of mortality from COVID19. For people over 65 with or without a comorbidity their chances of dying from COVID19 are also much higher than those under the age of 65. Due to stress applied to endothelial, lung, respiratory and immune cells by these comorbidities and in general the aging process, the presence of surface bound GRP78 has recently been recognized as an important player in aging and disease progression.

With aging and with comorbidities, cells become more stressed leading to consistent and higher expression of cell surface bound GRP78. This higher expression of the GRP78 allows for more viral binding and entry into cells (FIG. 1). Viral replication and release of the viral particles can then occur at a much higher rate. This process of increased binding, entry and replication of viruses due to increased GRP78 receptor can then overpower the immune system leading to increased morbidity and mortality.

Treating Patients with Autoimmune Diseases

Patients with autoimmune diseases do not have a fully functioning immune system and have been reported to present with higher expression of surface bound GRP78. Current treatments and vaccines that are designed to stimulate the immune system against viruses like SARS-CoV-2 are much less effective in these patients that are prone to unwanted increased viral progression. Providing prophylactic and/or therapeutic support with our GRP78 inhibitors to these patients may provide a level of protection against infection and if infected will block new viral attachment, entry, replication and release of new viral particles into the patient.

Treating Patients with Cancer

Patients with cancer, especially lung and blood borne cancers, have been shown to have a higher expression of surface bound GRP78 on their lower and higher respiratory tract cells as well as their endothelial cells. These patients, because of their chemotherapy treatments, usually have a reduced immune response to vaccines and pathogens. By treating these patients, either prophylactically or after infection SARS-CoV-2 virus, with our GRP78 inhibitions may allow for a decreased chance for infection and a decreased rate of viral infectivity by blocking virus access to the surface bound GRP78 receptor.

Treating Patients with Obesity.

Patients with obesity have several comorbidities like hypertension, diabetes, and poor circulation which can cause stressed lung and endothelial cells resulting in increased surface expressed GRP78. This increase in surface expressed GRP78 makes this group of people at high risk for SARS-CoV-2 infection and death. Using our GRP78 inhibitors to block the amount of viral infectivity through surface bound GRP78, we may greatly reduce symptoms and the severity of the viral infection.

Treating Patients with Diabetes

Patients with diabetic type 1 or type 2 disease have been shown to have higher expression of surface bound GRP78 on kidney and endothelial cells. With the use of our GRP78 inhibitors in these patients, the viral load and chance of SARS-CoV-2 infection should be greatly reduced allowing for normal immune attack and elimination of viral particles.

Treating Patients with Cardiovascular Disease

A hallmark for patients with cardiovascular disease is increased endoplasmic stress in heart tissues leading to higher expression of ACE2 and surface bound GRP78 on their vasculature cells. Although, increased ACE2 expression allows for increased SARS-CoV-2 attachment, this invention teaches that SARS-CoV-2 requires surface bound GRP78 for viral entry and as such, by reducing the surface expression of GRP78 with our GRP78 inhibitors, this should lead to reduced viral infection and mortality.

Treating Patients with Hypertension

Studies show that patients with hypertension have increased endoplasmic reticulum expressed GRP78 in their arterial cells. This increase in GRP78 expression leads to an increase in surface bound GRP78. As listed above, surface expression of GRP78 allows for higher SARS-CoV-2 viral attachment, entry and replication in cells. By reducing the expression of surface bound GRP78 with our inhibitors, not only will they reduce the risk for viral infection but also reduce chronic hypertension effects.

Treating Patients Over 65 Years of Age

With aging, inflammation is more prevalent, which leads to muscle and arterial cells being more stressed resulting in consistent expression of surface bound GRP78. It is clear that SARS-CoV-2 infection severity increases substantially with age. This higher level of GRP78 receptor allows for availability of more attachment and entry of SARS-CoV-2 virus into the cells. The treatment of patients over the age of 65 with GRP78 inhibitors will lead to reduced surface bound GRP78 on stressed unhealthy cells. With less receptors for SARS-CoV-2 virus attachment, the less severe the SARS-CoV-2 infection will be.

It is rare that young (<60), heathy people show severe symptoms from SARS-CoV-2 infection. We believe this is due to the fact that surface bound GRP78 on young, heathy people's cells is very low, which decreases the risk of viral attachment. This limits the severity of infection and greatly decreases the mortality rate of children and younger people. As such, there is no need to treat this population with our GRP78 inhibitors.

However, there are exceptions to this theory. For example, Influenza viruses infect the young and the old even though the viruses contain a GRP78 binding site and there is no surface bound GRP78 on their cells. Recent publications show that infected cells induce surface GRP78 expression, which leads to more infection. In these cases, treatment with GRP78 inhibitors will reduce surface bound GRP78, resulting in decreased viral load and a reduced time of infectivity.

Types of Treatment

For our GRP78 inhibitors, this invention shows two type of treatment options. The first is to give our GRP78 inhibitors as a treatment for patients listed above after SARS-CoV-2 infection. Infected patients with comorbidities will benefit from decreased surface bound GRP78 resulting in decreased virus attachment and entry.

The second method to use for our GRP78 inhibitors is to give them prophylactically. For the patients listed above with comorbidities and for those above 65 years of age whose lung, respiratory and arterial cells have increased surface bound GRP78 expression, treatment with our GRP78 inhibitors prophylactically will reduce the risk of SARS-CoV-2 viral infection and disease progression. Our GRP78 inhibitors given prophylactically will may also be effective at protecting health care workers, first responders, people who travel to high infection areas and teachers from SARS-CoV-2 infection.

Co-Treatment Options

This invention shows that our GRP78 inhibitors may be given in combination with other types of therapies to help reduce viral infection and the resulting symptoms. For example:

- anti-inflammatory agents like Dexamethasone have been shown to reduce the symptoms like cytokine inflammation leading to increased survival,
- anti-viral agents like Remdesivir which has been shown to block replication of viruses leading to reduced viral disease.
- immune suppressive agents like Baricitinib (JAK inhibitor), and Tocilzumab (IL6 inhibitor) which have not been shown to be effective in late-stage disease but show promise in early to mid-stage disease.
- anti-coagulant agents like heparin which significantly reduced the symptoms of clot storms as a result of SARS-CoV-2 infection.
- vaccines like those against SARS-CoV-2, or influenza may be effective against the main strain but not against evolving variants. By using both vaccines and GRP78 inhibitors, they may be more effective for cures.

Problems with Current Therapies and Vaccines Against SARS-CoV-2 Virus:

Vaccines against the SARS-CoV-2 virus are designed to force the immune system to attack the virus through either the spike protein on the virus surface or other envelope proteins. This then allows the body to make antibodies against the SARS-CoV-2 virus spike protein, which block SARS-CoV-2 virus attaching and internalizing into the host cell. Currently, there are three approved vaccines against the spike protein of SARS-CoV-2 virus. For people with a weaken immune system due to comorbidities or other drug treatments, these vaccines may not as effective. Also SARS-CoV-2 variant (B.1.351) infections have been shown to be resistant to the AstraZeneca Covid-19 vaccine for mild-to-moderate infections. This is the underlying issue with anti-viral vaccines in that there is a need for yearly updated versions of the vaccine to combat evolving variants.

Monoclonal antibodies against SARS-CoV-2 spike protein have been approved for emergency use by the FDA. These antibodies have been shown to be effective against patients with early SARS-CoV-2 infections. Patients that were hospitalized did not show any improvement. Finally, like vaccines these therapies are very targeted against the viral spike protein and variants may not be inhibited.

Remdesivir is a protease inhibitor that has been approved for use by the FDA. It also failed against hospitalized patients and did not prevent death. If give early in the SARS-CoV-2 viral infection, it was shown to decrease hospitalization time and duration of the infection.

Listed above are the only FDA approved therapies for COVID19 disease as of the writing of this invention. However, several others are progressing through clinical studies that show some promise. Baricitinib is a Janus Kinase inhibitor that is an immunosuppressant. This therapy has shown to be effective against SARS-CoV-2 virus infected patients on oxygen but not on ventilation. Again, late-stage COVID19 disease is not addressed. Tocilizumab is a monoclonal antibody against IL-6. Inhibiting IL-6 treats SARS-CoV-2 infection symptoms by tamping down inflammation allowing the immune system to function better. The outcomes from late-stage patients receiving Tocilzumab were reduced time to discharge for both people on ventilation and oxygen.

This invention teaches a method for treating patients with SARS-CoV-2 infection that uses N-terminal GRP78 inhibitors. Unlike the vaccines or current viral treatments, our therapy addresses the potential viral infection at the cell surface, not at the virus surface. By inhibiting the host cells receptors and not the virus, mutant variants will not be resistant to GRP78 inhibitor therapy. Also, since GRP78 inhibitors do not rely on the immune system for viral clearance or inhibition, immune suppressed patients can still be treated. As such, late stage COVID19 diseased patients, patients with suppressed immune systems or patients with comorbidities will still be sensitive to our GRP78 inhibitors, which will reduce infection time leading to less hospital stay and viral load.

FIG. 17 is a table showing protein sequence comparisons for GRP78 binding sites of K5 (SEQ ID NO: 190) and selected peptide sequences from various viruses. Amino acids underlined twice in FIG. 17 are identical to K5 (SEQ ID NO: 190) GRP78 binding site amino acids, and amino acids that are similar in type to those of K5 (SEQ ID NO: 190) are underlined only once. Where there is no underline under the amino acid, it is concluded there is no similarity. An asterisk (*) in FIG. 17 marks the amino acids important for GRP78 binding. The Cysteine amino acid at the beginning of the GRP78 binding sites is found in almost all sequences.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of such claims as shall be appended.

In accordance with my invention, I claim:

1. A method for treating or inhibiting a viral infection of severe acute respiratory syndrome coronavirus 2 (SARS-CoV-2) virus, the method comprising: administering to a subject in need thereof an effective dose of an antiviral agent that binds to the N-terminal domain of cell surface bound glucose-regulated protein 78 (GRP78), wherein the antiviral agent comprises a GRP78 antagonist selected from the group consisting of SEQ ID NO: 19 and SEQ ID NO: 20, and a pharmaceutically acceptable salt thereof.

2. A method of inhibiting an infection, proliferation, and migration of viral infection for viruses that use surface-bound GRP78 for attachment, entry and replication, the method comprising: administering to a subject in need thereof a pharmaceutically effective amount of an antiviral agent that binds to the N-terminal domain of cell surface bound glucose-regulated protein 78 (GRP78), wherein the antiviral agent comprises a GRP78 antagonist selected from the group consisting of SEQ ID NO: 19 and SEQ ID NO: 20, and a pharmaceutically acceptable salt thereof.

3. A method for treating or inhibiting severe acute respiratory syndrome coronavirus (SARS-CoV) virus, middle east respiratory coronavirus (MER-CoV) virus, Japanese Encephalitis virus, Coxsackievirus, Dengue virus and Influenza A & B viruses, the method comprising: administering to a subject in need thereof an effective dose of an antiviral agent that binds to the N-terminal domain of cell surface bound glucose-regulated protein 78 (GRP78), wherein the antiviral agent comprises a GRP78 antagonist selected from the group consisting of SEQ ID NO: 19 and SEQ ID NO: 20, and a pharmaceutically acceptable salt thereof.

4. The method of claim 1, wherein the GRP78 antagonist is SEQ ID NO: 19 or a pharmaceutically acceptable salt thereof.

5. The method of claim 1, wherein the GRP78 antagonist is SEQ ID NO: 20 or a pharmaceutically acceptable salt thereof.

6. The method of claim 2, wherein the GRP78 antagonist is SEQ ID NO: 19 or a pharmaceutically acceptable salt thereof.

7. The method of claim 2, wherein the GRP78 antagonist is SEQ ID NO: 20 or a pharmaceutically acceptable salt thereof.

8. The method of claim 3, wherein the GRP78 antagonist is SEQ ID NO: 19 or a pharmaceutically acceptable salt thereof.

9. The method of claim 3, wherein the GRP78 antagonist is SEQ ID NO: 20 or a pharmaceutically acceptable salt thereof.

* * * * *

SEQUENCE LISTING

```
<160> NUMBER OF SEQ ID NOS: 205

<210> SEQ ID NO 1
<211> LENGTH: 89
<212> TYPE: PRT
<213> ORGANISM: Artificial Sequence
<220> FEATURE:
<223> OTHER INFORMATION: Synthetic Peptide K5(3-89 Active Zone)

<400> SEQUENCE: 1

Ser Glu Glu Asp Cys Met Phe Gly Asn Gly Lys Gly Tyr Arg Gly Lys
1               5                   10                  15

Arg Ala Thr Thr Val Thr Gly Thr Pro Cys Gln Asp Trp Ala Ala Gln
            20                  25                  30

Glu Pro His Arg His Ser Ile Phe Thr Pro Glu Thr Asn Pro Arg Ala
        35                  40                  45

Gly Leu Glu Lys Asn Tyr Cys Arg Asn Pro Asp Gly Asp Val Gly Gly
    50                  55                  60

Pro Trp Cys Tyr Thr Thr Asn Pro Arg Lys Leu Tyr Asp Tyr Cys Asp
65                  70                  75                  80

Val Pro Gln Cys Ala Ala Pro Lys Ser
                85

<210> SEQ ID NO 2
<211> LENGTH: 317
```

```
<212> TYPE: PRT
<213> ORGANISM: Artificial Sequence
<220> FEATURE:
<223> OTHER INFORMATION: Synthetic Peptide K5(3-89 Active Zone)frag-Fc

<400> SEQUENCE: 2

Ser Glu Glu Asp Cys Met Phe Gly Asn Gly Lys Gly Tyr Arg Gly Lys
1               5                   10                  15

Arg Ala Thr Thr Val Thr Gly Thr Pro Cys Gln Asp Trp Ala Ala Gln
                20                  25                  30

Glu Pro His Arg His Ser Ile Phe Thr Pro Glu Thr Asn Pro Arg Ala
            35                  40                  45

Gly Leu Glu Lys Asn Tyr Cys Arg Asn Pro Asp Gly Asp Val Gly Gly
        50                  55                  60

Pro Trp Cys Tyr Thr Thr Asn Pro Arg Lys Leu Tyr Asp Tyr Cys Asp
65                  70                  75                  80

Val Pro Gln Cys Ala Ala Pro Lys Ser Cys Asp Lys Thr His Thr Cys
                85                  90                  95

Pro Pro Cys Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
        115                 120                 125

Val Thr Cys Val Val Val Asp Val Ser His Glu Asp Pro Glu Val Lys
130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
        195                 200                 205

Ala Lys Gly Gln Pro Arg Glu Pro Gln Val Tyr Thr Leu Pro Pro Ser
210                 215                 220

Arg Asp Glu Leu Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Tyr Ser Lys Leu Thr Val Asp Lys Ser Arg Trp Gln
        275                 280                 285

Gln Gly Asn Val Phe Ser Cys Ser Val Met His Glu Ala Leu His Asn
        290                 295                 300

His Tyr Thr Gln Lys Ser Leu Ser Leu Ser Pro Gly Lys
305                 310                 315

<210> SEQ ID NO 3
<211> LENGTH: 254
<212> TYPE: PRT
<213> ORGANISM: Artificial Sequence
<220> FEATURE:
<223> OTHER INFORMATION: Synthetic Peptide K5(57-81 Active Zone)frag -Fc

<400> SEQUENCE: 3

Arg Asn Pro Asp Gly Asp Val Gly Gly Pro Trp Cys Tyr Thr Thr Asn
1               5                   10                  15
```

```
Pro Arg Lys Leu Tyr Asp Tyr Cys Lys Ser Cys Asp Lys Thr His Thr
            20                  25                  30

Cys Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
 50                  55                  60

Glu Val Thr Cys Val Val Val Asp Val Ser His Glu Asp Pro Glu Val
 65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
            115                 120                 125

Lys Val Ser Asn Lys Ala Leu Pro Ala Pro Ile Glu Lys Thr Ile Ser
130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 4
<211> LENGTH: 254
<212> TYPE: PRT
<213> ORGANISM: Artificial Sequence
<220> FEATURE:
<223> OTHER INFORMATION: Synthetic Peptide K5(57-81 Active Zone w Ala
      sub Cys)frag -Fc

<400> SEQUENCE: 4

Arg Asn Pro Asp Gly Asp Val Gly Gly Pro Trp Ala Tyr Thr Thr Asn
 1               5                  10                  15

Pro Arg Lys Leu Tyr Asp Tyr Ala Lys Ser Cys Asp Lys Thr His Thr
            20                  25                  30

Cys Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
 50                  55                  60

Glu Val Thr Cys Val Val Val Asp Val Ser His Glu Asp Pro Glu Val
 65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
```

```
            115                 120                 125
Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 5
<211> LENGTH: 254
<212> TYPE: PRT
<213> ORGANISM: Artificial Sequence
<220> FEATURE:
<223> OTHER INFORMATION: Synthetic Peptide K5(57-81 Active Zone w Val
      sub Cys)frag-Fc

<400> SEQUENCE: 5

Arg Asn Pro Asp Gly Asp Val Gly Gly Pro Trp Val Tyr Thr Thr Asn
1               5                   10                  15

Pro Arg Lys Leu Tyr Asp Tyr Val Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220
```

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 6
<211> LENGTH: 254
<212> TYPE: PRT
<213> ORGANISM: Artificial Sequence
<220> FEATURE:
<223> OTHER INFORMATION: Synthetic Peptide K5(57-81 Active Zone w Ile
      sub Cys)frag-Fc

<400> SEQUENCE: 6

Arg Asn Pro Asp Gly Asp Val Gly Gly Pro Trp Ile Tyr Thr Thr Asn
1               5                   10                  15

Pro Arg Lys Leu Tyr Asp Tyr Ile Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 7
<211> LENGTH: 254
<212> TYPE: PRT
<213> ORGANISM: Artificial Sequence
<220> FEATURE:
<223> OTHER INFORMATION: Synthetic Peptide K5(57-81 Active Zone w Leu
      sub Cys)frag-Fc

<400> SEQUENCE: 7

Arg Asn Pro Asp Gly Asp Val Gly Gly Pro Trp Leu Tyr Thr Thr Asn
1               5                   10                  15

-continued

```
Pro Arg Lys Leu Tyr Asp Tyr Leu Lys Ser Cys Asp Lys Thr His Thr
            20                  25                  30

Cys Pro Pro Cys Pro Ala Pro Glu Leu Leu Gly Gly Pro Ser Val Phe
        35                  40                  45

Leu Phe Pro Pro Lys Pro Lys Asp Thr Leu Met Ile Ser Arg Thr Pro
 50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Pro Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Asp Glu Leu Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250
```

<210> SEQ ID NO 8
<211> LENGTH: 250
<212> TYPE: PRT
<213> ORGANISM: Artificial Sequence
<220> FEATURE:
<223> OTHER INFORMATION: Synthetic Peptide K5(70-89 Active Zone)frag-Fc

<400> SEQUENCE: 8

```
Tyr Thr Thr Asn Pro Arg Lys Leu Tyr Asp Tyr Cys Asp Val Pro Gln
1               5                   10                  15

Cys Ala Ala Pro Lys Ser Cys Asp Lys Thr His Thr Cys Pro Pro Cys
            20                  25                  30

Pro Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125
```

Lys Ala Leu Pro Ala Pro Ile Glu Lys Thr Ile Ser Lys Ala Lys Gly
            130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 9
<211> LENGTH: 250
<212> TYPE: PRT
<213> ORGANISM: Artificial Sequence
<220> FEATURE:
<223> OTHER INFORMATION: Synthetic Peptide K5(70-89 Active Zone with Ala
      sub Cys)frag-Fc

<400> SEQUENCE: 9

Tyr Thr Thr Asn Pro Arg Lys Leu Tyr Asp Tyr Ala Asp Val Pro Gln
1               5                   10                  15

Ala Ala Ala Pro Lys Ser Cys Asp Lys Thr His Thr Cys Pro Pro Cys
                20                  25                  30

Pro Ala Pro Glu Leu Leu Gly Gly Pro Ser Val Phe Leu Phe Pro Pro
            35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
            130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 10
<211> LENGTH: 250
<212> TYPE: PRT
<213> ORGANISM: Artificial Sequence
<220> FEATURE:
<223> OTHER INFORMATION: Synthetic Peptide K5(70-89 Active Zone with Val
      sub Cys)frag-Fc

<400> SEQUENCE: 10

Tyr Thr Thr Asn Pro Arg Lys Leu Tyr Asp Tyr Val Asp Val Pro Gln
1               5                   10                  15

Val Ala Ala Pro Lys Ser Cys Asp Lys Thr His Thr Cys Pro Pro Cys
            20                  25                  30

Pro Ala Pro Glu Leu Leu Gly Gly Pro Ser Val Phe Leu Phe Pro Pro
        35                  40                  45

Lys Pro Lys Asp Thr Leu Met Ile Ser Arg Thr Pro Glu Val Thr Cys
50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Ala Leu Pro Ala Pro Ile Glu Lys Thr Ile Ser Lys Ala Lys Gly
    130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
            245                 250

<210> SEQ ID NO 11
<211> LENGTH: 250
<212> TYPE: PRT
<213> ORGANISM: Artificial Sequence
<220> FEATURE:
<223> OTHER INFORMATION: Synthetic Peptide K5(70-89 Active Zone with Ile
      sub Cys)frag-Fc

<400> SEQUENCE: 11

Tyr Thr Thr Asn Pro Arg Lys Leu Tyr Asp Tyr Ile Asp Val Pro Gln
1               5                   10                  15

Ile Ala Ala Pro Lys Ser Cys Asp Lys Thr His Thr Cys Pro Pro Cys
            20                  25                  30

Pro Ala Pro Glu Leu Leu Gly Gly Pro Ser Val Phe Leu Phe Pro Pro
         35                  40                  45

Lys Pro Lys Asp Thr Leu Met Ile Ser Arg Thr Pro Glu Val Thr Cys
 50                  55                  60

Val Val Val Asp Val Ser His Glu Asp Pro Glu Val Lys Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
                115                 120                 125

Lys Ala Leu Pro Ala Pro Ile Glu Lys Thr Ile Ser Lys Ala Lys Gly
130                 135                 140

Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
                180                 185                 190

Asn Tyr Lys Thr Thr Pro Pro Val Leu Asp Ser Asp Gly Ser Phe Phe
                195                 200                 205

Leu Tyr Ser Lys Leu Thr Val Asp Lys Ser Arg Trp Gln Gln Gly Asn
210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 12
<211> LENGTH: 250
<212> TYPE: PRT
<213> ORGANISM: Artificial Sequence
<220> FEATURE:
<223> OTHER INFORMATION: Synthetic Peptide K5(70-89 Active Zone with Leu
      sub Cys)frag-Fc

<400> SEQUENCE: 12

Tyr Thr Thr Asn Pro Arg Lys Leu Tyr Asp Tyr Leu Asp Val Pro Gln
 1                5                  10                  15

Leu Ala Ala Pro Lys Ser Cys Asp Lys Thr His Thr Cys Pro Pro Cys
                 20                  25                  30

Pro Ala Pro Glu Leu Leu Gly Gly Pro Ser Val Phe Leu Phe Pro Pro
         35                  40                  45

Lys Pro Lys Asp Thr Leu Met Ile Ser Arg Thr Pro Glu Val Thr Cys
 50                  55                  60

Val Val Val Asp Val Ser His Glu Asp Pro Glu Val Lys Phe Asn Trp
 65                  70                  75                  80

Tyr Val Asp Gly Val Glu Val His Asn Ala Lys Thr Lys Pro Arg Glu
                 85                  90                  95

Glu Gln Tyr Asn Ser Thr Tyr Arg Val Val Ser Val Leu Thr Val Leu
                100                 105                 110

His Gln Asp Trp Leu Asn Gly Lys Glu Tyr Lys Cys Lys Val Ser Asn
                115                 120                 125

Lys Ala Leu Pro Ala Pro Ile Glu Lys Thr Ile Ser Lys Ala Lys Gly

```
                130                 135                 140
Gln Pro Arg Glu Pro Gln Val Tyr Thr Leu Pro Pro Ser Arg Asp Glu
145                 150                 155                 160

Leu Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
                180                 185                 190

Asn Tyr Lys Thr Thr Pro Pro Val Leu Asp Ser Asp Gly Ser Phe Phe
                195                 200                 205

Leu Tyr Ser Lys Leu Thr Val Asp Lys Ser Arg Trp Gln Gln Gly Asn
                210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 13
<211> LENGTH: 246
<212> TYPE: PRT
<213> ORGANISM: Artificial Sequence
<220> FEATURE:
<223> OTHER INFORMATION: Synthetic Peptide K5(74-89 Active Zone)frag-Fc

<400> SEQUENCE: 13

Pro Arg Lys Leu Tyr Asp Tyr Cys Asp Val Pro Gln Cys Ala Ala Pro
1               5                   10                  15

Lys Ser Cys Asp Lys Thr His Thr Cys Pro Pro Cys Pro Ala Pro Glu
                20                  25                  30

Leu Leu Gly Gly Pro Ser Val Phe Leu Phe Pro Pro Lys Pro Lys Asp
                35                  40                  45

Thr Leu Met Ile Ser Arg Thr Pro Glu Val Thr Cys Val Val Val Asp
                50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
                100                 105                 110

Leu Asn Gly Lys Glu Tyr Lys Cys Lys Val Ser Asn Lys Ala Leu Pro
                115                 120                 125

Ala Pro Ile Glu Lys Thr Ile Ser Lys Ala Lys Gly Gln Pro Arg Glu
130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
                180                 185                 190

Thr Pro Pro Val Leu Asp Ser Asp Gly Ser Phe Phe Leu Tyr Ser Lys
                195                 200                 205

Leu Thr Val Asp Lys Ser Arg Trp Gln Gln Gly Asn Val Phe Ser Cys
                210                 215                 220

Ser Val Met His Glu Ala Leu His Asn His Tyr Thr Gln Lys Ser Leu
225                 230                 235                 240

Ser Leu Ser Pro Gly Lys
```

<210> SEQ ID NO 14
<211> LENGTH: 246
<212> TYPE: PRT
<213> ORGANISM: Artificial Sequence
<220> FEATURE:
<223> OTHER INFORMATION: Synthetic Peptide K5(74-89 Active Zone w Ala sub Cys)frag-Fc

<400> SEQUENCE: 14

```
Pro Arg Lys Leu Tyr Asp Tyr Ala Asp Val Pro Gln Ala Ala Ala Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245
```

<210> SEQ ID NO 15
<211> LENGTH: 246
<212> TYPE: PRT
<213> ORGANISM: Artificial Sequence
<220> FEATURE:
<223> OTHER INFORMATION: Synthetic Peptide K5(74-89 Active Zone w Val sub Cys)frag-Fc

<400> SEQUENCE: 15

```
Pro Arg Lys Leu Tyr Asp Tyr Val Asp Val Pro Gln Val Ala Ala Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
```

```
        35                  40                  45
Thr Leu Met Ile Ser Arg Thr Pro Glu Val Thr Cys Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                     85                  90                  95

Ser Thr Tyr Arg Val Val Ser Val Leu Thr Val Leu His Gln Asp Trp
                    100                 105                 110

Leu Asn Gly Lys Glu Tyr Lys Cys Lys Val Ser Asn Lys Ala Leu Pro
                    115                 120                 125

Ala Pro Ile Glu Lys Thr Ile Ser Lys Ala Lys Gly Gln Pro Arg Glu
130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                    165                 170                 175

Ala Val Glu Trp Glu Ser Asn Gly Gln Pro Glu Asn Asn Tyr Lys Thr
                    180                 185                 190

Thr Pro Pro Val Leu Asp Ser Asp Gly Ser Phe Phe Leu Tyr Ser Lys
                    195                 200                 205

Leu Thr Val Asp Lys Ser Arg Trp Gln Gln Gly Asn Val Phe Ser Cys
210                 215                 220

Ser Val Met His Glu Ala Leu His Asn His Tyr Thr Gln Lys Ser Leu
225                 230                 235                 240

Ser Leu Ser Pro Gly Lys
                    245

<210> SEQ ID NO 16
<211> LENGTH: 246
<212> TYPE: PRT
<213> ORGANISM: Artificial Sequence
<220> FEATURE:
<223> OTHER INFORMATION: Synthetic Peptide K5(74-89 Active Zone w Ile
      sub Cys)frag-Fc

<400> SEQUENCE: 16

Pro Arg Lys Leu Tyr Asp Tyr Ile Asp Val Pro Gln Ile Ala Ala Pro
 1                   5                  10                  15

Lys Ser Cys Asp Lys Thr His Thr Cys Pro Pro Cys Pro Ala Pro Glu
                     20                  25                  30

Leu Leu Gly Gly Pro Ser Val Phe Leu Phe Pro Pro Lys Pro Lys Asp
                     35                  40                  45

Thr Leu Met Ile Ser Arg Thr Pro Glu Val Thr Cys Val Val Asp
 50                  55                  60

Val Ser His Glu Asp Pro Glu Val Lys Phe Asn Trp Tyr Val Asp Gly
 65                  70                  75                  80

Val Glu Val His Asn Ala Lys Thr Lys Pro Arg Glu Glu Gln Tyr Asn
                     85                  90                  95

Ser Thr Tyr Arg Val Val Ser Val Leu Thr Val Leu His Gln Asp Trp
                    100                 105                 110

Leu Asn Gly Lys Glu Tyr Lys Cys Lys Val Ser Asn Lys Ala Leu Pro
                    115                 120                 125

Ala Pro Ile Glu Lys Thr Ile Ser Lys Ala Lys Gly Gln Pro Arg Glu
130                 135                 140
```

```
Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
            165                 170                 175

Ala Val Glu Trp Glu Ser Asn Gly Gln Pro Glu Asn Asn Tyr Lys Thr
                180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 17
<211> LENGTH: 246
<212> TYPE: PRT
<213> ORGANISM: Artificial Sequence
<220> FEATURE:
<223> OTHER INFORMATION: Synthetic Peptide K5(74-89 Active Zone w Leu
      sub Cys)frag-Fc

<400> SEQUENCE: 17

Pro Arg Lys Leu Tyr Asp Tyr Leu Asp Val Pro Gln Leu Ala Ala Pro
1               5                   10                  15

Lys Ser Cys Asp Lys Thr His Thr Cys Pro Pro Cys Pro Ala Pro Glu
            20                  25                  30

Leu Leu Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
            165                 170                 175

Ala Val Glu Trp Glu Ser Asn Gly Gln Pro Glu Asn Asn Tyr Lys Thr
                180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245
```

<210> SEQ ID NO 18
<211> LENGTH: 237
<212> TYPE: PRT
<213> ORGANISM: Artificial Sequence
<220> FEATURE:
<223> OTHER INFORMATION: Synthetic Peptide K5(74-80 Active Zone)frag-Fc

<400> SEQUENCE: 18

Pro Arg Lys Leu Tyr Asp Tyr Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Asp Glu Leu Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 19
<211> LENGTH: 93
<212> TYPE: PRT
<213> ORGANISM: Artificial Sequence
<220> FEATURE:
<223> OTHER INFORMATION: Synthetic Peptide Kr1(1-93 Active Zone)frag

<400> SEQUENCE: 19

Gly Ser Asn Lys Asn His Lys Cys Tyr Asn Ser Thr Gly Val Asp Tyr
1               5                   10                  15

Arg Gly Thr Val Ser Val Thr Lys Ser Gly Arg Gln Cys Gln Pro Trp
            20                  25                  30

Asn Ser Gln Tyr Pro His Thr His Thr Phe Thr Ala Leu Arg Phe Pro
        35                  40                  45

Glu Leu Asn Gly Gly His Ser Tyr Cys Arg Asn Pro Gly Asn Gln Lys
    50                  55                  60

Glu Ala Pro Trp Cys Phe Thr Leu Asp Glu Asn Phe Lys Ser Asp Leu

```
                65                  70                  75                  80
Cys Asp Ile Pro Ala Cys Asp Ser Lys Asp Ser Asp Ile
                    85                  90

<210> SEQ ID NO 20
<211> LENGTH: 317
<212> TYPE: PRT
<213> ORGANISM: Artificial Sequence
<220> FEATURE:
<223> OTHER INFORMATION: Synthetic Peptide Kr1(3-91 Active Zone)frag-Fc

<400> SEQUENCE: 20

Asn Lys Asn His Lys Cys Tyr Asn Ser Thr Gly Val Asp Tyr Arg Gly
1               5                   10                  15

Thr Val Ser Val Thr Lys Ser Gly Arg Gln Cys Gln Pro Trp Asn Ser
            20                  25                  30

Gln Tyr Pro His Thr His Thr Phe Thr Ala Leu Arg Phe Pro Glu Leu
        35                  40                  45

Asn Gly Gly His Ser Tyr Cys Arg Asn Pro Gly Asn Gln Lys Glu Ala
    50                  55                  60

Pro Trp Cys Phe Thr Leu Asp Glu Asn Phe Lys Ser Asp Leu Cys Asp
65                  70                  75                  80

Ile Pro Ala Cys Asp Ser Lys Asp Ser Cys Asp Lys Thr His Thr Cys
                85                  90                  95

Pro Pro Cys Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
        115                 120                 125

Val Thr Cys Val Val Val Asp Val Ser His Glu Asp Pro Glu Val Lys
    130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
        195                 200                 205

Ala Lys Gly Gln Pro Arg Glu Pro Gln Val Tyr Thr Leu Pro Pro Ser
    210                 215                 220

Arg Asp Glu Leu Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
            260                 265                 270

Ser Phe Phe Leu Tyr Ser Lys Leu Thr Val Asp Lys Ser Arg Trp Gln
        275                 280                 285

Gln Gly Asn Val Phe Ser Cys Ser Val Met His Glu Ala Leu His Asn
    290                 295                 300

His Tyr Thr Gln Lys Ser Leu Ser Leu Ser Pro Gly Lys
305                 310                 315

<210> SEQ ID NO 21
<211> LENGTH: 262
<212> TYPE: PRT
```

-continued

```
<213> ORGANISM: Artificial Sequence
<220> FEATURE:
<223> OTHER INFORMATION: Synthetic Peptide Kr1(58-91 Active Zone)frag-Fc

<400> SEQUENCE: 21

Arg Asn Pro Gly Asn Gln Lys Glu Ala Pro Trp Cys Phe Thr Leu Asp
1               5                   10                  15

Glu Asn Phe Lys Ser Asp Leu Cys Asp Ile Pro Ala Cys Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
            85                  90                  95

Val Glu Val His Asn Ala Lys Thr Lys Pro Arg Glu Glu Gln Tyr Asn
        100                 105                 110

Ser Thr Tyr Arg Val Val Ser Val Leu Thr Val Leu His Gln Asp Trp
    115                 120                 125

Leu Asn Gly Lys Glu Tyr Lys Cys Lys Val Ser Asn Lys Ala Leu Pro
130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
            165                 170                 175

Gln Val Ser Leu Thr Cys Leu Val Lys Gly Phe Tyr Pro Ser Asp Ile
        180                 185                 190

Ala Val Glu Trp Glu Ser Asn Gly Gln Pro Glu Asn Asn Tyr Lys Thr
    195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
            245                 250                 255

Ser Leu Ser Pro Gly Lys
            260

<210> SEQ ID NO 22
<211> LENGTH: 262
<212> TYPE: PRT
<213> ORGANISM: Artificial Sequence
<220> FEATURE:
<223> OTHER INFORMATION: Synthetic Peptide Kr1(58-91 Active Zone with
      Ala sub Cys)frag-Fc

<400> SEQUENCE: 22

Arg Asn Pro Gly Asn Gln Lys Glu Ala Pro Trp Ala Phe Thr Leu Asp
1               5                   10                  15

Glu Asn Phe Lys Ser Asp Leu Ala Asp Ile Pro Ala Ala Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60
```

```
Thr Leu Met Ile Ser Arg Thr Pro Glu Val Thr Cys Val Val Val Asp
 65                  70                  75                  80

Val Ser His Glu Asp Pro Glu Val Lys Phe Asn Trp Tyr Val Asp Gly
                 85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 23
<211> LENGTH: 262
<212> TYPE: PRT
<213> ORGANISM: Artificial Sequence
<220> FEATURE:
<223> OTHER INFORMATION: Synthetic Peptide Kr1(58-91 Active Zone with
      Val sub Cys)frag-Fc

<400> SEQUENCE: 23

Arg Asn Pro Gly Asn Gln Lys Glu Ala Pro Trp Val Phe Thr Leu Asp
1               5                   10                  15

Glu Asn Phe Lys Ser Asp Leu Val Asp Ile Pro Ala Val Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
130                 135                 140

Ala Pro Ile Glu Lys Thr Ile Ser Lys Ala Lys Gly Gln Pro Arg Glu
```

```
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 24
<211> LENGTH: 262
<212> TYPE: PRT
<213> ORGANISM: Artificial Sequence
<220> FEATURE:
<223> OTHER INFORMATION: Synthetic Peptide Kr1(58-91 Active Zone with
      Ile sub Cys)frag-Fc

<400> SEQUENCE: 24

Arg Asn Pro Gly Asn Gln Lys Glu Ala Pro Trp Ile Phe Thr Leu Asp
1               5                   10                  15

Glu Asn Phe Lys Ser Asp Leu Ile Asp Ile Pro Ala Ile Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240
```

```
Ser Val Met His Glu Ala Leu His Asn His Tyr Thr Gln Lys Ser Leu
            245                 250                 255

Ser Leu Ser Pro Gly Lys
            260

<210> SEQ ID NO 25
<211> LENGTH: 262
<212> TYPE: PRT
<213> ORGANISM: Artificial Sequence
<220> FEATURE:
<223> OTHER INFORMATION: Synthetic Peptide Kr1(58-91 Active Zone with
      Leu sub Cys)frag-Fc

<400> SEQUENCE: 25

Arg Asn Pro Gly Asn Gln Lys Glu Ala Pro Trp Leu Phe Thr Leu Asp
1               5                   10                  15

Glu Asn Phe Lys Ser Asp Leu Leu Asp Ile Pro Ala Leu Asp Ser Lys
            20                  25                  30

Asp Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 26
<211> LENGTH: 251
<212> TYPE: PRT
<213> ORGANISM: Artificial Sequence
<220> FEATURE:
<223> OTHER INFORMATION: Synthetic Peptide Kr1(58-80 Active Zone)frag-Fc

<400> SEQUENCE: 26

Arg Asn Pro Gly Asn Gln Lys Glu Ala Pro Trp Cys Phe Thr Leu Asp
```

```
                1               5                   10                  15
            Glu Asn Phe Lys Ser Asp Leu Cys Asp Lys Thr His Thr Cys Pro Pro
                            20                  25                  30

Cys Pro Ala Pro Glu Leu Leu Gly Gly Pro Ser Val Phe Leu Phe Pro
                            35                  40                  45

Pro Lys Pro Lys Asp Thr Leu Met Ile Ser Arg Thr Pro Glu Val Thr
                50                          55                  60

Cys Val Val Val Asp Val Ser His Glu Asp Pro Glu Val Lys Phe Asn
            65                  70                  75                  80

Trp Tyr Val Asp Gly Val Glu Val His Asn Ala Lys Thr Lys Pro Arg
                            85                  90                  95

Glu Glu Gln Tyr Asn Ser Thr Tyr Arg Val Val Ser Val Leu Thr Val
                            100                 105                 110

Leu His Gln Asp Trp Leu Asn Gly Lys Glu Tyr Lys Cys Lys Val Ser
                        115                 120                 125

Asn Lys Ala Leu Pro Ala Pro Ile Glu Lys Thr Ile Ser Lys Ala Lys
                        130                 135                 140

Gly Gln Pro Arg Glu Pro Gln Val Tyr Thr Leu Pro Pro Ser Arg Asp
            145                 150                 155                 160

Glu Leu Thr Lys Asn Gln Val Ser Leu Thr Cys Leu Val Lys Gly Phe
                            165                 170                 175

Tyr Pro Ser Asp Ile Ala Val Glu Trp Glu Ser Asn Gly Gln Pro Glu
                        180                 185                 190

Asn Asn Tyr Lys Thr Thr Pro Pro Val Leu Asp Ser Asp Gly Ser Phe
                        195                 200                 205

Phe Leu Tyr Ser Lys Leu Thr Val Asp Lys Ser Arg Trp Gln Gln Gly
                210                 215                 220

Asn Val Phe Ser Cys Ser Val Met His Glu Ala Leu His Asn His Tyr
            225                 230                 235                 240

Thr Gln Lys Ser Leu Ser Leu Ser Pro Gly Lys
                            245                 250

<210> SEQ ID NO 27
<211> LENGTH: 251
<212> TYPE: PRT
<213> ORGANISM: Artificial Sequence
<220> FEATURE:
<223> OTHER INFORMATION: Synthetic Peptide Kr1(58-80 Active Zone w Ala
      sub Cys)frag-Fc

<400> SEQUENCE: 27

Arg Asn Pro Gly Asn Gln Lys Glu Ala Pro Trp Ala Phe Thr Leu Asp
            1               5                   10                  15

Glu Asn Phe Lys Ser Asp Leu Cys Asp Lys Thr His Thr Cys Pro Pro
                            20                  25                  30

Cys Pro Ala Pro Glu Leu Leu Gly Gly Pro Ser Val Phe Leu Phe Pro
                            35                  40                  45

Pro Lys Pro Lys Asp Thr Leu Met Ile Ser Arg Thr Pro Glu Val Thr
                50                          55                  60

Cys Val Val Val Asp Val Ser His Glu Asp Pro Glu Val Lys Phe Asn
            65                  70                  75                  80

Trp Tyr Val Asp Gly Val Glu Val His Asn Ala Lys Thr Lys Pro Arg
                            85                  90                  95

Glu Glu Gln Tyr Asn Ser Thr Tyr Arg Val Val Ser Val Leu Thr Val
                            100                 105                 110
```

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
        130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 28
<211> LENGTH: 251
<212> TYPE: PRT
<213> ORGANISM: Artificial Sequence
<220> FEATURE:
<223> OTHER INFORMATION: Synthetic Peptide Kr1(58-80 Active Zone w Val
      sub Cys)frag-Fc

<400> SEQUENCE: 28

Arg Asn Pro Gly Asn Gln Lys Glu Ala Pro Trp Val Phe Thr Leu Asp
1               5                   10                  15

Glu Asn Phe Lys Ser Asp Leu Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
            115                 120                 125

Asn Lys Ala Leu Pro Ala Pro Ile Glu Lys Thr Ile Ser Lys Ala Lys
        130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

```
Asn Val Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 29
<211> LENGTH: 251
<212> TYPE: PRT
<213> ORGANISM: Artificial Sequence
<220> FEATURE:
<223> OTHER INFORMATION: Synthetic Peptide Kr1(58-80 Active Zone w Ile
      sub Cys)frag-Fc

<400> SEQUENCE: 29

Arg Asn Pro Gly Asn Gln Lys Glu Ala Pro Trp Ile Phe Thr Leu Asp
1               5                   10                  15

Glu Asn Phe Lys Ser Asp Leu Cys Asp Lys Thr His Thr Cys Pro Pro
                20                  25                  30

Cys Pro Ala Pro Glu Leu Leu Gly Gly Pro Ser Val Phe Leu Phe Pro
            35                  40                  45

Pro Lys Pro Lys Asp Thr Leu Met Ile Ser Arg Thr Pro Glu Val Thr
50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
            245                 250

<210> SEQ ID NO 30
<211> LENGTH: 251
<212> TYPE: PRT
<213> ORGANISM: Artificial Sequence
<220> FEATURE:
<223> OTHER INFORMATION: Synthetic Peptide Kr1(58-80 Active Zone w Leu
      sub Cys)frag-Fc

<400> SEQUENCE: 30

Arg Asn Pro Gly Asn Gln Lys Glu Ala Pro Trp Leu Phe Thr Leu Asp
1               5                   10                  15
```

```
Glu Asn Phe Lys Ser Asp Leu Cys Asp Lys Thr His Thr Cys Pro Pro
                20                  25                  30

Cys Pro Ala Pro Glu Leu Leu Gly Gly Pro Ser Val Phe Leu Phe Pro
             35                  40                  45

Pro Lys Pro Lys Asp Thr Leu Met Ile Ser Arg Thr Pro Glu Val Thr
 50                  55                  60

Cys Val Val Val Asp Val Ser His Glu Asp Pro Glu Val Lys Phe Asn
 65                  70                  75                  80

Trp Tyr Val Asp Gly Val Glu Val His Asn Ala Lys Thr Lys Pro Arg
                 85                  90                  95

Glu Glu Gln Tyr Asn Ser Thr Tyr Arg Val Val Ser Val Leu Thr Val
                100                 105                 110

Leu His Gln Asp Trp Leu Asn Gly Lys Glu Tyr Lys Cys Lys Val Ser
             115                 120                 125

Asn Lys Ala Leu Pro Ala Pro Ile Glu Lys Thr Ile Ser Lys Ala Lys
130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 31
<211> LENGTH: 239
<212> TYPE: PRT
<213> ORGANISM: Artificial Sequence
<220> FEATURE:
<223> OTHER INFORMATION: Synthetic Peptide Kr1(70-80 Active Zone)frag-Fc

<400> SEQUENCE: 31

Phe Thr Leu Asp Glu Asn Phe Lys Ser Asp Leu Cys Asp Lys Thr His
 1               5                  10                  15

Thr Cys Pro Pro Cys Pro Ala Pro Glu Leu Leu Gly Gly Pro Ser Val
                20                  25                  30

Phe Leu Phe Pro Pro Lys Pro Lys Asp Thr Leu Met Ile Ser Arg Thr
             35                  40                  45

Pro Glu Val Thr Cys Val Val Val Asp Val Ser His Glu Asp Pro Glu
 50                  55                  60

Val Lys Phe Asn Trp Tyr Val Asp Gly Val Glu Val His Asn Ala Lys
 65                  70                  75                  80

Thr Lys Pro Arg Glu Glu Gln Tyr Asn Ser Thr Tyr Arg Val Val Ser
                 85                  90                  95

Val Leu Thr Val Leu His Gln Asp Trp Leu Asn Gly Lys Glu Tyr Lys
                100                 105                 110

Cys Lys Val Ser Asn Lys Ala Leu Pro Ala Pro Ile Glu Lys Thr Ile
            115                 120                 125
```

```
Ser Lys Ala Lys Gly Gln Pro Arg Glu Pro Gln Val Tyr Thr Leu Pro
        130                 135                 140

Pro Ser Arg Asp Glu Leu Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Val Leu Asp Ser
            180                 185                 190

Asp Gly Ser Phe Phe Leu Tyr Ser Lys Leu Thr Val Asp Lys Ser Arg
        195                 200                 205

Trp Gln Gln Gly Asn Val Phe Ser Cys Ser Val Met His Glu Ala Leu
    210                 215                 220

His Asn His Tyr Thr Gln Lys Ser Leu Ser Leu Ser Pro Gly Lys
225                 230                 235
```

<210> SEQ ID NO 32
<211> LENGTH: 236
<212> TYPE: PRT
<213> ORGANISM: Artificial Sequence
<220> FEATURE:
<223> OTHER INFORMATION: Synthetic Peptide Kr1(73-80 Active Zone)frag-Fc

<400> SEQUENCE: 32

```
Asp Glu Asn Phe Lys Ser Asp Leu Cys Asp Lys Thr His Thr Cys Pro
1               5                   10                  15

Pro Cys Pro Ala Pro Glu Leu Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235
```

<210> SEQ ID NO 33

```
<211> LENGTH: 85
<212> TYPE: PRT
<213> ORGANISM: Artificial Sequence
<220> FEATURE:
<223> OTHER INFORMATION: Synthetic Peptide Kr2(1-85 Active Zone)frag

<400> SEQUENCE: 33

Gly Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
                20                  25                  30

Gln His Pro His Ser His His Leu Ser Ser Thr Asp Phe Pro Glu Leu
            35                  40                  45

Gly Gly Gly His Ala Tyr Cys Arg Asn Pro Gly Gly Gln Met Glu Gly
        50                  55                  60

Pro Trp Cys Phe Thr Gln Asn Lys Asn Val Arg Met Glu Leu Cys Asp
65                  70                  75                  80

Val Pro Ser Cys Ser
                85

<210> SEQ ID NO 34
<211> LENGTH: 316
<212> TYPE: PRT
<213> ORGANISM: Artificial Sequence
<220> FEATURE:
<223> OTHER INFORMATION: Synthetic Peptide Kr2(1-85 Active Zone)frag-Fc

<400> SEQUENCE: 34

Gly Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
                20                  25                  30

Gln His Pro His Ser His His Leu Ser Ser Thr Asp Phe Pro Glu Leu
            35                  40                  45

Gly Gly Gly His Ala Tyr Cys Arg Asn Pro Gly Gly Gln Met Glu Gly
        50                  55                  60

Pro Trp Cys Phe Thr Gln Asn Lys Asn Val Arg Met Glu Leu Cys Asp
65                  70                  75                  80

Val Pro Ser Cys Ser Pro Lys Ser Cys Asp Lys Thr His Thr Cys Pro
                85                  90                  95

Pro Cys Pro Ala Pro Glu Leu Leu Gly Gly Pro Ser Val Phe Leu Phe
            100                 105                 110

Pro Pro Lys Pro Lys Asp Thr Leu Met Ile Ser Arg Thr Pro Glu Val
        115                 120                 125

Thr Cys Val Val Val Asp Val Ser His Glu Asp Pro Glu Val Lys Phe
    130                 135                 140

Asn Trp Tyr Val Asp Gly Val Glu Val His Asn Ala Lys Thr Lys Pro
145                 150                 155                 160

Arg Glu Glu Gln Tyr Asn Ser Thr Tyr Arg Val Val Ser Val Leu Thr
                165                 170                 175

Val Leu His Gln Asp Trp Leu Asn Gly Lys Glu Tyr Lys Cys Lys Val
            180                 185                 190

Ser Asn Lys Ala Leu Pro Ala Pro Ile Glu Lys Thr Ile Ser Lys Ala
        195                 200                 205

Lys Gly Gln Pro Arg Glu Pro Gln Val Tyr Thr Leu Pro Pro Ser Arg
    210                 215                 220

Asp Glu Leu Thr Lys Asn Gln Val Ser Leu Thr Cys Leu Val Lys Gly
```

```
            225                 230                 235                 240

Phe Tyr Pro Ser Asp Ile Ala Val Glu Trp Glu Ser Asn Gly Gln Pro
                        245                 250                 255

Glu Asn Asn Tyr Lys Thr Thr Pro Pro Val Leu Asp Ser Asp Gly Ser
                        260                 265                 270

Phe Phe Leu Tyr Ser Lys Leu Thr Val Asp Lys Ser Arg Trp Gln Gln
                        275                 280                 285

Gly Asn Val Phe Ser Cys Ser Val Met His Glu Ala Leu His Asn His
                        290                 295                 300

Tyr Thr Gln Lys Ser Leu Ser Leu Ser Pro Gly Lys
        305                 310                 315

<210> SEQ ID NO 35
<211> LENGTH: 261
<212> TYPE: PRT
<213> ORGANISM: Artificial Sequence
<220> FEATURE:
<223> OTHER INFORMATION: Synthetic Peptide Kr2(56-85 Active Zone)frag-Fc

<400> SEQUENCE: 35

Arg Asn Pro Gly Gly Gln Met Glu Gly Pro Trp Cys Phe Thr Gln Asn
        1               5                   10                  15

Lys Asn Val Arg Met Glu Leu Cys Asp Val Pro Ser Cys Ser Pro Lys
                        20                  25                  30

Ser Cys Asp Lys Thr His Thr Cys Pro Pro Cys Pro Ala Pro Glu Leu
                        35                  40                  45

Leu Gly Gly Pro Ser Val Phe Leu Phe Pro Pro Lys Pro Lys Asp Thr
        50                  55                  60

Leu Met Ile Ser Arg Thr Pro Glu Val Thr Cys Val Val Val Asp Val
        65                  70                  75                  80

Ser His Glu Asp Pro Glu Val Lys Phe Asn Trp Tyr Val Asp Gly Val
                        85                  90                  95

Glu Val His Asn Ala Lys Thr Lys Pro Arg Glu Glu Gln Tyr Asn Ser
                        100                 105                 110

Thr Tyr Arg Val Val Ser Val Leu Thr Val Leu His Gln Asp Trp Leu
                        115                 120                 125

Asn Gly Lys Glu Tyr Lys Cys Lys Val Ser Asn Lys Ala Leu Pro Ala
        130                 135                 140

Pro Ile Glu Lys Thr Ile Ser Lys Ala Lys Gly Gln Pro Arg Glu Pro
        145                 150                 155                 160

Gln Val Tyr Thr Leu Pro Pro Ser Arg Asp Glu Leu Thr Lys Asn Gln
                        165                 170                 175

Val Ser Leu Thr Cys Leu Val Lys Gly Phe Tyr Pro Ser Asp Ile Ala
                        180                 185                 190

Val Glu Trp Glu Ser Asn Gly Gln Pro Glu Asn Asn Tyr Lys Thr Thr
                        195                 200                 205

Pro Pro Val Leu Asp Ser Asp Gly Ser Phe Phe Leu Tyr Ser Lys Leu
        210                 215                 220

Thr Val Asp Lys Ser Arg Trp Gln Gln Gly Asn Val Phe Ser Cys Ser
        225                 230                 235                 240

Val Met His Glu Ala Leu His Asn His Tyr Thr Gln Lys Ser Leu Ser
                        245                 250                 255

Leu Ser Pro Gly Lys
                        260
```

<210> SEQ ID NO 36
<211> LENGTH: 261
<212> TYPE: PRT
<213> ORGANISM: Artificial Sequence
<220> FEATURE:
<223> OTHER INFORMATION: Synthetic Peptide Kr2(56-85 Active Zone w Ala sub Cys)frag-Fc

<400> SEQUENCE: 36

```
Arg Asn Pro Gly Gly Gln Met Glu Gly Pro Trp Ala Phe Thr Gln Asn
1               5                   10                  15

Lys Asn Val Arg Met Glu Leu Ala Asp Val Pro Ser Ala Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260
```

<210> SEQ ID NO 37
<211> LENGTH: 261
<212> TYPE: PRT
<213> ORGANISM: Artificial Sequence
<220> FEATURE:
<223> OTHER INFORMATION: Synthetic Peptide Kr2(56-85 Active Zone w Val sub Cys)frag-Fc

<400> SEQUENCE: 37

```
Arg Asn Pro Gly Gly Gln Met Glu Gly Pro Trp Val Phe Thr Gln Asn
1               5                   10                  15

Lys Asn Val Arg Met Glu Leu Val Asp Val Pro Ser Val Ser Pro Lys
            20                  25                  30

Ser Cys Asp Lys Thr His Thr Cys Pro Pro Cys Pro Ala Pro Glu Leu
```

```
                    35                  40                  45
Leu Gly Gly Pro Ser Val Phe Leu Phe Pro Pro Lys Pro Lys Asp Thr
             50                  55                  60
Leu Met Ile Ser Arg Thr Pro Glu Val Thr Cys Val Val Val Asp Val
 65                  70                  75                  80
Ser His Glu Asp Pro Glu Val Lys Phe Asn Trp Tyr Val Asp Gly Val
                 85                  90                  95
Glu Val His Asn Ala Lys Thr Lys Pro Arg Glu Glu Gln Tyr Asn Ser
                100                 105                 110
Thr Tyr Arg Val Val Ser Val Leu Thr Val Leu His Gln Asp Trp Leu
            115                 120                 125
Asn Gly Lys Glu Tyr Lys Cys Lys Val Ser Asn Lys Ala Leu Pro Ala
        130                 135                 140
Pro Ile Glu Lys Thr Ile Ser Lys Ala Lys Gly Gln Pro Arg Glu Pro
145                 150                 155                 160
Gln Val Tyr Thr Leu Pro Pro Ser Arg Asp Glu Leu Thr Lys Asn Gln
                165                 170                 175
Val Ser Leu Thr Cys Leu Val Lys Gly Phe Tyr Pro Ser Asp Ile Ala
            180                 185                 190
Val Glu Trp Glu Ser Asn Gly Gln Pro Glu Asn Asn Tyr Lys Thr Thr
        195                 200                 205
Pro Pro Val Leu Asp Ser Asp Gly Ser Phe Phe Leu Tyr Ser Lys Leu
210                 215                 220
Thr Val Asp Lys Ser Arg Trp Gln Gln Gly Asn Val Phe Ser Cys Ser
225                 230                 235                 240
Val Met His Glu Ala Leu His Asn His Tyr Thr Gln Lys Ser Leu Ser
                245                 250                 255
Leu Ser Pro Gly Lys
            260

<210> SEQ ID NO 38
<211> LENGTH: 261
<212> TYPE: PRT
<213> ORGANISM: Artificial Sequence
<220> FEATURE:
<223> OTHER INFORMATION: Synthetic Peptide Kr2(56-85 Active Zone w Ile
      sub Cys)frag-Fc

<400> SEQUENCE: 38

Arg Asn Pro Gly Gly Gln Met Glu Gly Pro Trp Ile Phe Thr Gln Asn
 1                   5                  10                  15
Lys Asn Val Arg Met Glu Leu Ile Asp Val Pro Ser Ile Ser Pro Lys
                 20                  25                  30
Ser Cys Asp Lys Thr His Thr Cys Pro Pro Cys Pro Ala Pro Glu Leu
            35                  40                  45
Leu Gly Gly Pro Ser Val Phe Leu Phe Pro Pro Lys Pro Lys Asp Thr
        50                  55                  60
Leu Met Ile Ser Arg Thr Pro Glu Val Thr Cys Val Val Val Asp Val
 65                  70                  75                  80
Ser His Glu Asp Pro Glu Val Lys Phe Asn Trp Tyr Val Asp Gly Val
                 85                  90                  95
Glu Val His Asn Ala Lys Thr Lys Pro Arg Glu Glu Gln Tyr Asn Ser
                100                 105                 110
Thr Tyr Arg Val Val Ser Val Leu Thr Val Leu His Gln Asp Trp Leu
            115                 120                 125
```

Asn Gly Lys Glu Tyr Lys Cys Lys Val Ser Asn Lys Ala Leu Pro Ala
        130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 39
<211> LENGTH: 261
<212> TYPE: PRT
<213> ORGANISM: Artificial Sequence
<220> FEATURE:
<223> OTHER INFORMATION: Synthetic Peptide Kr2(56-85 Active Zone w Leu
      sub Cys)frag-Fc

<400> SEQUENCE: 39

Arg Asn Pro Gly Gly Gln Met Glu Gly Pro Trp Leu Phe Thr Gln Asn
1               5                   10                  15

Lys Asn Val Arg Met Glu Leu Leu Asp Val Pro Ser Leu Ser Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

```
Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 40
<211> LENGTH: 249
<212> TYPE: PRT
<213> ORGANISM: Artificial Sequence
<220> FEATURE:
<223> OTHER INFORMATION: Synthetic Peptide Kr2(68-85 Active Zone)frag-Fc

<400> SEQUENCE: 40

Phe Thr Gln Asn Lys Asn Val Arg Met Glu Leu Cys Asp Val Pro Ser
1               5                   10                  15

Cys Ser Pro Lys Ser Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 41
<211> LENGTH: 249
<212> TYPE: PRT
<213> ORGANISM: Artificial Sequence
<220> FEATURE:
<223> OTHER INFORMATION: Synthetic Peptide Kr2(68-85 Active Zone w Ala
      sub Cys)frag-Fc

<400> SEQUENCE: 41
```

```
Phe Thr Gln Asn Lys Asn Val Arg Met Glu Leu Ala Asp Val Pro Ser
1               5                   10                  15

Ala Ser Pro Lys Ser Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
    210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 42
<211> LENGTH: 249
<212> TYPE: PRT
<213> ORGANISM: Artificial Sequence
<220> FEATURE:
<223> OTHER INFORMATION: Synthetic Peptide Kr2(68-85 Active Zone w Val
      sub Cys)frag-Fc

<400> SEQUENCE: 42

Phe Thr Gln Asn Lys Asn Val Arg Met Glu Leu Val Asp Val Pro Ser
1               5                   10                  15

Val Ser Pro Lys Ser Cys Asp Lys Thr His Thr Cys Pro Pro Cys Pro
                20                  25                  30

Ala Pro Glu Leu Leu Gly Gly Pro Ser Val Phe Leu Phe Pro Pro Lys
            35                  40                  45

Pro Lys Asp Thr Leu Met Ile Ser Arg Thr Pro Glu Val Thr Cys Val
        50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110
```

```
Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 43
<211> LENGTH: 249
<212> TYPE: PRT
<213> ORGANISM: Artificial Sequence
<220> FEATURE:
<223> OTHER INFORMATION: Synthetic Peptide Kr2(68-85 Active Zone w Ile
      sub Cys)frag-Fc

<400> SEQUENCE: 43

Phe Thr Gln Asn Lys Asn Val Arg Met Glu Leu Ile Asp Val Pro Ser
1               5                   10                  15

Ile Ser Pro Lys Ser Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
    130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
```

```
            210                 215                 220
Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 44
<211> LENGTH: 249
<212> TYPE: PRT
<213> ORGANISM: Artificial Sequence
<220> FEATURE:
<223> OTHER INFORMATION: Synthetic Peptide Kr2(68-85 Active Zone w Leu
      sub Cys)frag-Fc

<400> SEQUENCE: 44

Phe Thr Gln Asn Lys Asn Val Arg Met Glu Leu Leu Asp Val Pro Ser
1               5                   10                  15

Leu Ser Pro Lys Ser Cys Asp Lys Thr His Thr Cys Pro Pro Cys Pro
            20                  25                  30

Ala Pro Glu Leu Leu Gly Gly Pro Ser Val Phe Leu Phe Pro Pro Lys
        35                  40                  45

Pro Lys Asp Thr Leu Met Ile Ser Arg Thr Pro Glu Val Thr Cys Val
50                  55                  60

Val Val Asp Val Ser His Glu Asp Pro Glu Val Lys Phe Asn Trp Tyr
65                  70                  75                  80

Val Asp Gly Val Glu Val His Asn Ala Lys Thr Lys Pro Arg Glu Glu
                85                  90                  95

Gln Tyr Asn Ser Thr Tyr Arg Val Val Ser Val Leu Thr Val Leu His
            100                 105                 110

Gln Asp Trp Leu Asn Gly Lys Glu Tyr Lys Cys Lys Val Ser Asn Lys
        115                 120                 125

Ala Leu Pro Ala Pro Ile Glu Lys Thr Ile Ser Lys Ala Lys Gly Gln
130                 135                 140

Pro Arg Glu Pro Gln Val Tyr Thr Leu Pro Pro Ser Arg Asp Glu Leu
145                 150                 155                 160

Thr Lys Asn Gln Val Ser Leu Thr Cys Leu Val Lys Gly Phe Tyr Pro
                165                 170                 175

Ser Asp Ile Ala Val Glu Trp Glu Ser Asn Gly Gln Pro Glu Asn Asn
            180                 185                 190

Tyr Lys Thr Thr Pro Pro Val Leu Asp Ser Asp Gly Ser Phe Phe Leu
        195                 200                 205

Tyr Ser Lys Leu Thr Val Asp Lys Ser Arg Trp Gln Gln Gly Asn Val
210                 215                 220

Phe Ser Cys Ser Val Met His Glu Ala Leu His Asn His Tyr Thr Gln
225                 230                 235                 240

Lys Ser Leu Ser Leu Ser Pro Gly Lys
                245

<210> SEQ ID NO 45
<211> LENGTH: 241
<212> TYPE: PRT
<213> ORGANISM: Artificial Sequence
<220> FEATURE:
<223> OTHER INFORMATION: Synthetic Peptide Kr2(68-79 Active Zone w Lys
      sub Cys)frag-Fc

<400> SEQUENCE: 45

Phe Thr Gln Asn Lys Asn Val Arg Met Glu Leu Lys Ser Cys Asp Lys
```

```
            1               5                  10                 15
        Thr His Thr Cys Pro Pro Cys Pro Ala Pro Glu Leu Gly Gly Pro
                       20                 25                 30
        Ser Val Phe Leu Phe Pro Pro Lys Pro Lys Asp Thr Leu Met Ile Ser
                       35                 40                 45
        Arg Thr Pro Glu Val Thr Cys Val Val Val Asp Val Ser His Glu Asp
                  50                 55                 60
        Pro Glu Val Lys Phe Asn Trp Tyr Val Asp Gly Val Glu Val His Asn
         65                 70                 75                 80
        Ala Lys Thr Lys Pro Arg Glu Glu Gln Tyr Asn Ser Thr Tyr Arg Val
                       85                 90                 95
        Val Ser Val Leu Thr Val Leu His Gln Asp Trp Leu Asn Gly Lys Glu
                      100                105                110
        Tyr Lys Cys Lys Val Ser Asn Lys Ala Leu Pro Ala Pro Ile Glu Lys
                      115                120                125
        Thr Ile Ser Lys Ala Lys Gly Gln Pro Arg Glu Pro Gln Val Tyr Thr
                      130                135                140
        Leu Pro Pro Ser Arg Asp Glu Leu Thr Lys Asn Gln Val Ser Leu Thr
        145                150                155                160
        Cys Leu Val Lys Gly Phe Tyr Pro Ser Asp Ile Ala Val Glu Trp Glu
                      165                170                175
        Ser Asn Gly Gln Pro Glu Asn Asn Tyr Lys Thr Thr Pro Pro Val Leu
                      180                185                190
        Asp Ser Asp Gly Ser Phe Phe Leu Tyr Ser Lys Leu Thr Val Asp Lys
                      195                200                205
        Ser Arg Trp Gln Gln Gly Asn Val Phe Ser Cys Ser Val Met His Glu
                      210                215                220
        Ala Leu His Asn His Tyr Thr Gln Lys Ser Leu Ser Leu Ser Pro Gly
        225                230                235                240
        Lys

<210> SEQ ID NO 46
<211> LENGTH: 24
<212> TYPE: PRT
<213> ORGANISM: Artificial Sequence
<220> FEATURE:
<223> OTHER INFORMATION: Synthetic Peptide Kr1(58-81 Active Zone w Ala
      sub Cys and w Lys sub Cys)frag

<400> SEQUENCE: 46

Arg Asn Pro Gly Asn Gln Lys Glu Ala Pro Trp Ala Phe Thr Leu Asp
 1               5                  10                 15

Glu Asn Phe Lys Ser Asp Leu Lys
            20

<210> SEQ ID NO 47
<211> LENGTH: 24
<212> TYPE: PRT
<213> ORGANISM: Artificial Sequence
<220> FEATURE:
<223> OTHER INFORMATION: Synthetic Peptide Kr1(58-81 Active Zone w Val
      sub Cys and w Lys sub Cys)frag

<400> SEQUENCE: 47

Arg Asn Pro Gly Asn Gln Lys Glu Ala Pro Trp Val Phe Thr Leu Asp
 1               5                  10                 15

Glu Asn Phe Lys Ser Asp Leu Lys
            20
```

```
<210> SEQ ID NO 48
<211> LENGTH: 24
<212> TYPE: PRT
<213> ORGANISM: Artificial Sequence
<220> FEATURE:
<223> OTHER INFORMATION: Synthetic Peptide Kr1(58-81 Active Zone w Ile
      sub Cys and w Lys sub Cys)frag

<400> SEQUENCE: 48

Arg Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 49
<211> LENGTH: 24
<212> TYPE: PRT
<213> ORGANISM: Artificial Sequence
<220> FEATURE:
<223> OTHER INFORMATION: Synthetic Peptide Kr1(58-81 Active Zone w Leu
      sub Cys and w Lys sub Cys)frag

<400> SEQUENCE: 49

Arg Asn Pro Gly Asn Gln Lys Glu Ala Pro Trp Leu Phe Thr Leu Asp
1               5                   10                  15

Glu Asn Phe Lys Ser Asp Leu Lys
            20

<210> SEQ ID NO 50
<211> LENGTH: 23
<212> TYPE: PRT
<213> ORGANISM: Artificial Sequence
<220> FEATURE:
<223> OTHER INFORMATION: Synthetic Peptide Kr1(58-80 Active Zone w Ala
      sub Cys)frag

<400> SEQUENCE: 50

Arg Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic Peptide Kr1(58-80 Active Zone w Val
      sub Cys)frag

<400> SEQUENCE: 51

Arg Asn Pro Gly Asn Gln Lys Glu Ala Pro Trp Val Phe Thr Leu Asp
1               5                   10                  15

Glu Asn Phe Lys Ser Asp Leu
            20

<210> SEQ ID NO 52
<211> LENGTH: 23
<212> TYPE: PRT
<213> ORGANISM: Artificial Sequence
<220> FEATURE:
<223> OTHER INFORMATION: Synthetic Peptide Kr1(58-80 Active Zone w Ile
      sub Cys)frag

<400> SEQUENCE: 52
```

Arg Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 53
<211> LENGTH: 23
<212> TYPE: PRT
<213> ORGANISM: Artificial Sequence
<220> FEATURE:
<223> OTHER INFORMATION: Synthetic Peptide Kr1(58-80 Active Zone w Leu
      sub Cys)frag

<400> SEQUENCE: 53

Arg Asn Pro Gly Asn Gln Lys Glu Ala Pro Trp Leu Phe Thr Leu Asp
1               5                   10                  15

Glu Asn Phe Lys Ser Asp Leu
            20

<210> SEQ ID NO 54
<211> LENGTH: 12
<212> TYPE: PRT
<213> ORGANISM: Artificial Sequence
<220> FEATURE:
<223> OTHER INFORMATION: Synthetic Peptide Kr1(58-69 Active Zone w Lys
      sub Cys)frag

<400> SEQUENCE: 54

Arg Asn Pro Gly Asn Gln Lys Glu Ala Pro Trp Lys
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Peptide Kr1(58-68 Active Zone)frag

<400> SEQUENCE: 55

Arg Asn Pro Gly Asn Gln Lys Glu Ala Pro Trp
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Peptide Kr1(70-81 Active Zone w Lys
      sub Cys)frag

<400> SEQUENCE: 56

Phe Thr Leu Asp Glu Asn Phe Lys Ser Asp Leu Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide Kr1(70-80 Active Zone)frag

<400> SEQUENCE: 57

Phe Thr Leu Asp Glu Asn Phe Lys Ser Asp Leu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic Peptide Kr1(71-80 Active Zone)frag

<400> SEQUENCE: 58

Thr Leu Asp Glu Asn Phe Lys Ser Asp Leu
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic Peptide Kr1(72-80 Active Zone)frag

<400> SEQUENCE: 59

Leu Asp Glu Asn Phe Lys Ser Asp Leu
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Peptide Kr1(73-80 Active Zone)frag

<400> SEQUENCE: 60

Asp Glu Asn Phe Lys Ser Asp Leu
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Peptide Kr1(73-79 Active Zone)frag

<400> SEQUENCE: 61

Asp Glu Asn Phe Lys Ser Asp
1               5

<210> SEQ ID NO 62
<211> LENGTH: 79
<212> TYPE: PRT
<213> ORGANISM: Artificial Sequence
<220> FEATURE:
<223> OTHER INFORMATION: Synthetic Peptide Kr2(6-84 Active Zone)frag

<400> SEQUENCE: 62

Cys Tyr Asn Gly Ser Gly Met Asp Tyr Arg Gly Thr Ala Ser Thr Thr
1               5                   10                  15

Lys Ser Gly His Gln Cys Gln Pro Trp Ala Leu Gln His Pro His Ser
            20                  25                  30

His His Leu Ser Ser Thr Asp Phe Pro Glu Leu Gly Gly Gly His Ala
        35                  40                  45

Tyr Cys Arg Asn Pro Gly Gly Gln Met Glu Gly Pro Trp Cys Phe Thr
    50                  55                  60

Gln Asn Lys Asn Val Arg Met Glu Leu Cys Asp Val Pro Ser Cys
65                  70                  75

<210> SEQ ID NO 63
<211> LENGTH: 24

```
<212> TYPE: PRT
<213> ORGANISM: Artificial Sequence
<220> FEATURE:
<223> OTHER INFORMATION: Synthetic Peptide Kr2(56-79 Active Zone w Ala
      sub Cys and Lys sub Cys)frag

<400> SEQUENCE: 63

Arg Asn Pro Gly Gly Gln Met Glu Gly Pro Trp Ala Phe Thr Gln Asn
1               5                   10                  15

Lys Asn Val Arg Met Glu Leu Lys
            20

<210> SEQ ID NO 64
<211> LENGTH: 24
<212> TYPE: PRT
<213> ORGANISM: Artificial Sequence
<220> FEATURE:
<223> OTHER INFORMATION: Synthetic Peptide Kr2(56-79 Active Zone w Val
      sub Cys and Lys sub Cys)frag

<400> SEQUENCE: 64

Arg Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 65
<211> LENGTH: 24
<212> TYPE: PRT
<213> ORGANISM: Artificial Sequence
<220> FEATURE:
<223> OTHER INFORMATION: Synthetic Peptide Kr2(56-79 Active Zone w Ile
      sub Cys and Lys sub Cys)

<400> SEQUENCE: 65

Arg Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 66
<211> LENGTH: 24
<212> TYPE: PRT
<213> ORGANISM: Artificial Sequence
<220> FEATURE:
<223> OTHER INFORMATION: Synthetic Peptide Kr2(56-79 Active Zone w Leu
      sub Cys and Lys sub Cys)frag

<400> SEQUENCE: 66

Arg Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 67
<211> LENGTH: 23
<212> TYPE: PRT
<213> ORGANISM: Artificial Sequence
<220> FEATURE:
<223> OTHER INFORMATION: Synthetic Peptide Kr2(56-78 Active Zone w Ala
      sub Cys)frag

<400> SEQUENCE: 67

Arg Asn Pro Gly Gly Gln Met Glu Gly Pro Trp Ala Phe Thr Gln Asn
1               5                   10                  15
```

```
Lys Asn Val Arg Met Glu Leu
            20

<210> SEQ ID NO 68
<211> LENGTH: 23
<212> TYPE: PRT
<213> ORGANISM: Artificial Sequence
<220> FEATURE:
<223> OTHER INFORMATION: Synthetic Peptide Kr2(56-78 Active Zone w Val
      sub Cys)frag

<400> SEQUENCE: 68

Arg Asn Pro Gly Gly Gln Met Glu Gly Pro Trp Val Phe Thr Gln Asn
1               5                   10                  15

Lys Asn Val Arg Met Glu Leu
            20

<210> SEQ ID NO 69
<211> LENGTH: 23
<212> TYPE: PRT
<213> ORGANISM: Artificial Sequence
<220> FEATURE:
<223> OTHER INFORMATION: Synthetic Peptide Kr2(56-78 Active Zone w Ile
      sub Cys)frag

<400> SEQUENCE: 69

Arg Asn Pro Gly Gly Gln Met Glu Gly Pro Trp Ile Phe Thr Gln Asn
1               5                   10                  15

Lys Asn Val Arg Met Glu Leu
            20

<210> SEQ ID NO 70
<211> LENGTH: 23
<212> TYPE: PRT
<213> ORGANISM: Artificial Sequence
<220> FEATURE:
<223> OTHER INFORMATION: Synthetic Peptide Kr2(56-78 Active Zone w Leu
      sub Cys)frag

<400> SEQUENCE: 70

Arg Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 71
<211> LENGTH: 12
<212> TYPE: PRT
<213> ORGANISM: Artificial Sequence
<220> FEATURE:
<223> OTHER INFORMATION: Synthetic Peptide Kr2(56-67 Active Zone with
      Lys sub Cys)frag

<400> SEQUENCE: 71

Arg Asn Pro Gly Gly Gln Met Glu Gly Pro Trp Lys
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Peptide Kr2(56-66 Active Zone)frag

<400> SEQUENCE: 72

Arg Asn Pro Gly Gly Gln Met Glu Gly Pro Trp
```

```
<210> SEQ ID NO 73
<211> LENGTH: 12
<212> TYPE: PRT
<213> ORGANISM: Artificial Sequence
<220> FEATURE:
<223> OTHER INFORMATION: Synthetic Peptide Kr2(68-79 Active Zone w Lys
      sub Cys)frag

<400> SEQUENCE: 73

Phe Thr Gln Asn Lys Asn Val Arg Met Glu Leu Lys
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Peptide Kr2(68-78 Active Zone)frag

<400> SEQUENCE: 74

Phe Thr Gln Asn Lys Asn Val Arg Met Glu Leu
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Peptide Kr2(69-78 Active Zone)frag

<400> SEQUENCE: 75

Thr Gln Asn Lys Asn Val Arg Met Glu Leu
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide Kr2(70-78 Active Zone)frag

<400> SEQUENCE: 76

Gln Asn Lys Asn Val Arg Met Glu Leu
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Peptide Kr2(70-77 Active Zone)frag

<400> SEQUENCE: 77

Gln Asn Lys Asn Val Arg Met Glu
1               5

<210> SEQ ID NO 78
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Ala sub Cys and w Lys sub Cys)frag
<220> FEATURE:
<221> NAME/KEY: VARIANT
<222> LOCATION: (1)..(1)
```

<223> OTHER INFORMATION: Xaa is Arg linked to NAc

<400> SEQUENCE: 78

Xaa Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 79
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Val sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 79

Xaa Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 80
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Ile sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 80

Xaa Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 81
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Leu sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 81

Xaa Asn Pro Gly Asn Gln Lys Glu Ala Pro Trp Leu Phe Thr Leu Asp
1               5                   10                  15

Glu Asn Phe Lys Ser Asp Leu Lys
            20

<210> SEQ ID NO 82
<211> LENGTH: 24
<212> TYPE: PRT
<213> ORGANISM: Artificial Sequence
<220> FEATURE:

```
<223> OTHER INFORMATION: Synthetic Peptide Mod-Kr1(58-81 Active Zone w
      Ala sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 82

Xaa Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 83
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Val sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 83

Xaa Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 84
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Ile sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 84

Xaa Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 85
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Leu sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 85

Xaa Asn Pro Gly Asn Gln Lys Glu Ala Pro Trp Leu Phe Thr Leu Asp
1               5                   10                  15

Glu Asn Phe Lys Ser Asp Leu Lys
            20
```

```
<210> SEQ ID NO 86
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Ala sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 86

Xaa Asn Pro Gly Asn Gln Lys Glu Ala Pro Trp Ala Phe Thr Leu Asp
1               5                   10                  15

Glu Asn Phe Lys Ser Asp Leu Lys
            20

<210> SEQ ID NO 87
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Val sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 87

Xaa Asn Pro Gly Asn Gln Lys Glu Ala Pro Trp Val Phe Thr Leu Asp
1               5                   10                  15

Glu Asn Phe Lys Ser Asp Leu Lys
            20

<210> SEQ ID NO 88
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Ile sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 88

Xaa Asn Pro Gly Asn Gln Lys Glu Ala Pro Trp Ile Phe Thr Leu Asp
1               5                   10                  15

Glu Asn Phe Lys Ser Asp Leu Lys
            20

<210> SEQ ID NO 89
<211> LENGTH: 24
<212> TYPE: PRT
<213> ORGANISM: Artificial Sequence
<220> FEATURE:
<223> OTHER INFORMATION: Synthetic Peptide Mod-Kr1(58-81 Active Zone w
      Leu sub Cys and w Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 89

Xaa Asn Pro Gly Asn Gln Lys Glu Ala Pro Trp Leu Phe Thr Leu Asp
1               5                   10                  15
```

```
Glu Asn Phe Lys Ser Asp Leu Lys
            20

<210> SEQ ID NO 90
<211> LENGTH: 23
<212> TYPE: PRT
<213> ORGANISM: Artificial Sequence
<220> FEATURE:
<223> OTHER INFORMATION: Synthetic Peptide Mod-Kr1(58-81 Active Zone w
      Ala sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (23)..(23)
<223> OTHER INFORMATION: Xaa is Lys linked to N-epsilon-MPA

<400> SEQUENCE: 90

Xaa Pro Gly Asn Gln Lys Glu Ala Pro Trp Ala Phe Thr Leu Asp Glu
1               5                   10                  15

Asn Phe Lys Ser Asp Leu Xaa
            20

<210> SEQ ID NO 91
<211> LENGTH: 23
<212> TYPE: PRT
<213> ORGANISM: Artificial Sequence
<220> FEATURE:
<223> OTHER INFORMATION: Synthetic Peptide Mod-Kr1(58-81 Active Zone w
      Val sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (23)..(23)
<223> OTHER INFORMATION: Xaa is Lys linked to N-epsilon-MPA

<400> SEQUENCE: 91

Xaa Pro Gly Asn Gln Lys Glu Ala Pro Trp Val Phe Thr Leu Asp Glu
1               5                   10                  15

Asn Phe Lys Ser Asp Leu Xaa
            20

<210> SEQ ID NO 92
<211> LENGTH: 23
<212> TYPE: PRT
<213> ORGANISM: Artificial Sequence
<220> FEATURE:
<223> OTHER INFORMATION: Synthetic Peptide Mod-Kr1(58-81 Active Zone w
      Ile sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (23)..(23)
<223> OTHER INFORMATION: Xaa is Lys linked to N-epsilon-MPA

<400> SEQUENCE: 92

Xaa Pro Gly Asn Gln Lys Glu Ala Pro Trp Ile Phe Thr Leu Asp Glu
1               5                   10                  15

Asn Phe Lys Ser Asp Leu Xaa
            20
```

<210> SEQ ID NO 93
<211> LENGTH: 23
<212> TYPE: PRT
<213> ORGANISM: Artificial Sequence
<220> FEATURE:
<223> OTHER INFORMATION: Synthetic Peptide Mod-Kr1(58-81 Active Zone w
     Leu sub Cys and w Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (23)..(23)
<223> OTHER INFORMATION: Xaa is Lys linked to N-epsilon-MPA

<400> SEQUENCE: 93

Xaa Pro Gly Asn Gln Lys Glu Ala Pro Trp Leu Phe Thr Leu Asp Glu
1               5                   10                  15

Asn Phe Lys Ser Asp Leu Xaa
            20

<210> SEQ ID NO 94
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
     Ala sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 94

Xaa Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 95
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
     Val sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 95

Xaa Asn Pro Gly Asn Gln Lys Glu Ala Pro Trp Val Phe Thr Leu Asp
1               5                   10                  15

Glu Asn Phe Lys Ser Asp Leu
            20

<210> SEQ ID NO 96
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
     Ile sub Cys)frag
<220> FEATURE:
<221> NAME/KEY: VARIANT
<222> LOCATION: (1)..(1)
<223> OTHER INFORMATION: Xaa is Arg linked to NAc -continued

```
<400> SEQUENCE: 96

Xaa Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 97
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
      Leu sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 97

Xaa Asn Pro Gly Asn Gln Lys Glu Ala Pro Trp Leu Phe Thr Leu Asp
1               5                   10                  15

Glu Asn Phe Lys Ser Asp Leu
            20

<210> SEQ ID NO 98
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
      Ala sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 98

Xaa Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 99
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
      Val sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 99

Xaa Asn Pro Gly Asn Gln Lys Glu Ala Pro Trp Val Phe Thr Leu Asp
1               5                   10                  15

Glu Asn Phe Lys Ser Asp Leu
            20

<210> SEQ ID NO 100
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
```

```
                Ile sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 100

Xaa Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 101
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone w
                Leu sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 101

Xaa Asn Pro Gly Asn Gln Lys Glu Ala Pro Trp Leu Phe Thr Leu Asp
1               5                   10                  15

Glu Asn Phe Lys Ser Asp Leu
            20

<210> SEQ ID NO 102
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active Zone)
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 102

Xaa Asn Pro Gly Asn Gln Lys Glu Ala Pro Trp Ala Phe Thr Leu Asp
1               5                   10                  15

Glu Asn Phe Lys Ser Asp Leu
            20

<210> SEQ ID NO 103
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active
                Zone)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 103

Xaa Asn Pro Gly Asn Gln Lys Glu Ala Pro Trp Val Phe Thr Leu Asp
1               5                   10                  15

Glu Asn Phe Lys Ser Asp Leu
            20

<210> SEQ ID NO 104
<211> LENGTH: 23
```

```
<212> TYPE: PRT
<213> ORGANISM: Artificial Sequence
<220> FEATURE:
<223> OTHER INFORMATION: Synthetic Peptide Mod-Kr1(58-80 Active
      Zone)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 104

Xaa Asn Pro Gly Asn Gln Lys Glu Ala Pro Trp Ile Phe Thr Leu Asp
1               5                   10                  15

Glu Asn Phe Lys Ser Asp Leu
            20

<210> SEQ ID NO 105
<211> LENGTH: 23
<212> TYPE: PRT
<213> ORGANISM: Artificial Sequence
<220> FEATURE:
<223> OTHER INFORMATION: Synthetic Peptide Mod-Kr1(58-80 Active
      Zone)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 105

Xaa Asn Pro Gly Asn Gln Lys Glu Ala Pro Trp Leu Phe Thr Leu Asp
1               5                   10                  15

Glu Asn Phe Lys Ser Asp Leu
            20

<210> SEQ ID NO 106
<211> LENGTH: 12
<212> TYPE: PRT
<213> ORGANISM: Artificial Sequence
<220> FEATURE:
<223> OTHER INFORMATION: Synthetic Peptide Mod-Kr1(58-69 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 106

Xaa Asn Pro Gly Asn Gln Lys Glu Ala Pro Trp Lys
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic Peptide Mod-Kr1(58-69 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 107

Xaa Asn Pro Gly Asn Gln Lys Glu Ala Pro Trp Lys
1               5                   10

<210> SEQ ID NO 108
<211> LENGTH: 12
<212> TYPE: PRT
```

-continued

```
<213> ORGANISM: Artificial Sequence
<220> FEATURE:
<223> OTHER INFORMATION: Synthetic Peptide Mod-Kr1(58-69 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 108

Xaa Asn Pro Gly Asn Gln Lys Glu Ala Pro Trp Lys
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic Peptide Mod-Kr1(58-69 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (12)..(12)
<223> OTHER INFORMATION: Xaa is Lys linked to N-epsilon-MPA

<400> SEQUENCE: 109

Xaa Asn Pro Gly Asn Gln Lys Glu Ala Pro Trp Xaa
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic Peptide Mod-Kr1(58-68 Active
      Zone)frag
<220> FEATURE:
<221> NAME/KEY: VARIANT
<222> LOCATION: (1)..(1)
<223> OTHER INFORMATION: Xaa is Arg linked to NAc

<400> SEQUENCE: 110

Xaa Asn Pro Gly Asn Gln Lys Glu Ala Pro Trp
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Synthetic Peptide Mod-Kr1(58-68 Active
      Zone)frag
<220> FEATURE:
<221> NAME/KEY: VARIANT
<222> LOCATION: (1)..(1)
<223> OTHER INFORMATION: Xaa is Arg linked to MPA

<400> SEQUENCE: 111

Xaa Asn Pro Gly Asn Gln Lys Glu Ala Pro Trp
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic Peptide Mod-Kr1(58-68 Active
```

Zone)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 112

Xaa Asn Pro Gly Asn Gln Lys Glu Ala Pro Trp
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic Peptide Mod-Kr1(70-81 Active Zone w
      Lys sub Cys)frag
<220> FEATURE:
<221> NAME/KEY: VARIANT
<222> LOCATION: (1)..(1)
<223> OTHER INFORMATION: Xaa is Phe linked to NAc

<400> SEQUENCE: 113

Xaa Thr Leu Asp Glu Asn Phe Lys Ser Asp Leu Lys
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic Peptide Mod-Kr1(70-81 Active Zone w
      Lys sub Cys)frag
<220> FEATURE:
<221> NAME/KEY: VARIANT
<222> LOCATION: (1)..(1)
<223> OTHER INFORMATION: Xaa is Phe linked to MPA

<400> SEQUENCE: 114

Xaa Thr Leu Asp Glu Asn Phe Lys Ser Asp Leu Lys
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic Peptide Mod-Kr1(70-81 Active Zone w
      Lys sub Cys)frag
<220> FEATURE:
<221> NAME/KEY: VARIANT
<222> LOCATION: (1)..(1)
<223> OTHER INFORMATION: Xaa is Phe linked to MPA-AEEA

<400> SEQUENCE: 115

Xaa Thr Leu Asp Glu Asn Phe Lys Ser Asp Leu Lys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic Peptide Mod-Kr1(70-81 Active Zone w
      Lys sub Cys)frag
<220> FEATURE:
<221> NAME/KEY: VARIANT
<222> LOCATION: (1)..(1)
<223> OTHER INFORMATION: Xaa is Phe linked to NAc
<220> FEATURE:
<221> NAME/KEY: VARIANT

```
<222> LOCATION: (12)..(12)
<223> OTHER INFORMATION: Xaa is Lys linked to N-epsilon-MPA

<400> SEQUENCE: 116

Xaa Thr Leu Asp Glu Asn Phe Lys Ser Asp Leu Xaa
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic Peptide Mod-Kr1(70-80 Active
      Zone)frag
<220> FEATURE:
<221> NAME/KEY: VARIANT
<222> LOCATION: (1)..(1)
<223> OTHER INFORMATION: Xaa is Phe linked to NAc

<400> SEQUENCE: 117

Xaa Thr Leu Asp Glu Asn Phe Lys Ser Asp Leu
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Peptide Mod-Kr1(70-80 Active
      Zone)frag
<220> FEATURE:
<221> NAME/KEY: VARIANT
<222> LOCATION: (1)..(1)
<223> OTHER INFORMATION: Xaa is Phe linked to MPA

<400> SEQUENCE: 118

Xaa Thr Leu Asp Glu Asn Phe Lys Ser Asp Leu
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic Peptide Mod-Kr1(70-80 Active
      Zone)frag
<220> FEATURE:
<221> NAME/KEY: VARIANT
<222> LOCATION: (1)..(1)
<223> OTHER INFORMATION: Xaa is Phe linked to MPA-AEEA

<400> SEQUENCE: 119

Xaa Thr Leu Asp Glu Asn Phe Lys Ser Asp Leu
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic Peptide Mod-Kr1(71-80 Active
      Zone)frag
<220> FEATURE:
<221> NAME/KEY: VARIANT
<222> LOCATION: (1)..(1)
<223> OTHER INFORMATION: Xaa is Thr linked to NAc

<400> SEQUENCE: 120

Xaa Leu Asp Glu Asn Phe Lys Ser Asp Leu
1               5                   10
```

```
<210> SEQ ID NO 121
<211> LENGTH: 10
<212> TYPE: PRT
<213> ORGANISM: Artificial Sequence
<220> FEATURE:
<223> OTHER INFORMATION: Synthetic Peptide Mod-Kr1(71-80 Active
      Zone)frag
<220> FEATURE:
<221> NAME/KEY: VARIANT
<222> LOCATION: (1)..(1)
<223> OTHER INFORMATION: Xaa is Thr linked to MPA

<400> SEQUENCE: 121

Xaa Leu Asp Glu Asn Phe Lys Ser Asp Leu
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic Peptide Mod-Kr1(71-80 Active
      Zone)frag
<220> FEATURE:
<221> NAME/KEY: VARIANT
<222> LOCATION: (1)..(1)
<223> OTHER INFORMATION: Xaa is Thr linked to MPA-AEEA

<400> SEQUENCE: 122

Xaa Leu Asp Glu Asn Phe Lys Ser Asp Leu
1               5                   10

<210> SEQ ID NO 123
<211> LENGTH: 9
<212> TYPE: PRT
<213> ORGANISM: Artificial Sequence
<220> FEATURE:
<223> OTHER INFORMATION: Synthetic Peptide Mod-Kr1(72-80 Active
      Zone)frag
<220> FEATURE:
<221> NAME/KEY: VARIANT
<222> LOCATION: (1)..(1)
<223> OTHER INFORMATION: Xaa is Leu linked to NAc

<400> SEQUENCE: 123

Xaa Asp Glu Asn Phe Lys Ser Asp Leu
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic Peptide Mod-Kr1(72-80 Active
      Zone)frag
<220> FEATURE:
<221> NAME/KEY: VARIANT
<222> LOCATION: (1)..(1)
<223> OTHER INFORMATION: Xaa is Leu linked to MPA

<400> SEQUENCE: 124

Xaa Asp Glu Asn Phe Lys Ser Asp Leu
1               5

<210> SEQ ID NO 125
<211> LENGTH: 9
<212> TYPE: PRT
<213> ORGANISM: Artificial Sequence
<220> FEATURE:
```

```
<223> OTHER INFORMATION: Synthetic Peptide Mod-Kr1(72-80 Active
      Zone)frag
<220> FEATURE:
<221> NAME/KEY: VARIANT
<222> LOCATION: (1)..(1)
<223> OTHER INFORMATION: Xaa is Leu linked to MPA-AEEA

<400> SEQUENCE: 125

Xaa Asp Glu Asn Phe Lys Ser Asp Leu
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Peptide Mod-Kr1(73-80 Active
      Zone)frag
<220> FEATURE:
<221> NAME/KEY: VARIANT
<222> LOCATION: (1)..(1)
<223> OTHER INFORMATION: Xaa is Asp linked to NAc

<400> SEQUENCE: 126

Xaa Glu Asn Phe Lys Ser Asp Leu
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic Peptide Mod-Kr1(73-80 Active
Zone)frag
<220> FEATURE:
<221> NAME/KEY: VARIANT
<222> LOCATION: (1)..(1)
<223> OTHER INFORMATION: Xaa is Asp linked to MPA

<400> SEQUENCE: 127

Xaa Glu Asn Phe Lys Ser Asp Leu
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Peptide Mod-Kr1(73-80 Active
      Zone)frag
<220> FEATURE:
<221> NAME/KEY: VARIANT
<222> LOCATION: (1)..(1)
<223> OTHER INFORMATION: Xaa is Asp linked to MPA-AEEA

<400> SEQUENCE: 128

Xaa Glu Asn Phe Lys Ser Asp Leu
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic Peptide Mod-Kr1(73-79 Active
      Zone)frag
<220> FEATURE:
<221> NAME/KEY: VARIANT
<222> LOCATION: (1)..(1)
<223> OTHER INFORMATION: Xaa is Asp linked to NAc
```

<400> SEQUENCE: 129

Xaa Glu Asn Phe Lys Ser Asp
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic Peptide Mod-Kr1(73-79 Active
Zone)frag
<220> FEATURE:
<221> NAME/KEY: VARIANT
<222> LOCATION: (1)..(1)
<223> OTHER INFORMATION: Xaa is Asp linked to MPA

<400> SEQUENCE: 130

Xaa Glu Asn Phe Lys Ser Asp
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic Peptide Mod-Kr1(73-79 Active
      Zone)frag
<220> FEATURE:
<221> NAME/KEY: VARIANT
<222> LOCATION: (1)..(1)
<223> OTHER INFORMATION: Xaa is Asp linked to MPA-AEEA

<400> SEQUENCE: 131

Xaa Glu Asn Phe Lys Ser Asp
1               5

<210> SEQ ID NO 132
<211> LENGTH: 85
<212> TYPE: PRT
<213> ORGANISM: Artificial Sequence
<220> FEATURE:
<223> OTHER INFORMATION: Synthetic Peptide Kr2(1-85 Active Zone)frag
<220> FEATURE:
<221> NAME/KEY: VARIANT
<222> LOCATION: (1)..(1)
<223> OTHER INFORMATION: Xaa is Gly is linked to NAc

<400> SEQUENCE: 132

Xaa Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
            20                  25                  30

Gln His Pro His Ser His His Leu Ser Ser Thr Asp Phe Pro Glu Leu
        35                  40                  45

Gly Gly Gly His Ala Tyr Cys Arg Asn Pro Gly Gly Gln Met Glu Gly
    50                  55                  60

Pro Trp Cys Phe Thr Gln Asn Lys Asn Val Arg Met Glu Leu Cys Asp
65                  70                  75                  80

Val Pro Ser Cys Ser
                85

<210> SEQ ID NO 133
<211> LENGTH: 85
<212> TYPE: PRT
<213> ORGANISM: Artificial Sequence
<220> FEATURE:

<223> OTHER INFORMATION: Synthetic Peptide Kr2(1-85 Active Zone)frag
<220> FEATURE:
<221> NAME/KEY: VARIANT
<222> LOCATION: (1)..(1)
<223> OTHER INFORMATION: Xaa is Gly is linked to MPA

<400> SEQUENCE: 133

Xaa Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
            20                  25                  30

Gln His Pro His Ser His His Leu Ser Ser Thr Asp Phe Pro Glu Leu
        35                  40                  45

Gly Gly Gly His Ala Tyr Cys Arg Asn Pro Gly Gly Gln Met Glu Gly
    50                  55                  60

Pro Trp Cys Phe Thr Gln Asn Lys Asn Val Arg Met Glu Leu Cys Asp
65                  70                  75                  80

Val Pro Ser Cys Ser
                85

<210> SEQ ID NO 134
<211> LENGTH: 85
<212> TYPE: PRT
<213> ORGANISM: Artificial Sequence
<220> FEATURE:
<223> OTHER INFORMATION: Synthetic Peptide Kr2(1-85 Active Zone)frag
<220> FEATURE:
<221> NAME/KEY: VARIANT
<222> LOCATION: (1)..(1)
<223> OTHER INFORMATION: Xaa is Gly is linked to MPA-AEEA

<400> SEQUENCE: 134

Xaa Arg Tyr His Gln Cys Tyr Asn Gly Ser Gly Met Asp Tyr Arg Gly
1               5                   10                  15

Thr Ala Ser Thr Thr Lys Ser Gly His Gln Cys Gln Pro Trp Ala Leu
            20                  25                  30

Gln His Pro His Ser His His Leu Ser Ser Thr Asp Phe Pro Glu Leu
        35                  40                  45

Gly Gly Gly His Ala Tyr Cys Arg Asn Pro Gly Gly Gln Met Glu Gly
    50                  55                  60

Pro Trp Cys Phe Thr Gln Asn Lys Asn Val Arg Met Glu Leu Cys Asp
65                  70                  75                  80

Val Pro Ser Cys Ser
                85

<210> SEQ ID NO 135
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Ala sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 135

Xaa Asn Pro Gly Gly Gln Met Glu Gly Pro Trp Ala Phe Thr Gln Asn
1               5                   10                  15

Lys Asn Val Arg Met Glu Leu Lys
            20

<210> SEQ ID NO 136
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
    Val sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 136

Xaa Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 137
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
    Ile sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 137

Xaa Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 138
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
    Leu sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 138

Xaa Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 139
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
    Ala sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 139

Xaa Asn Pro Gly Gly Gln Met Glu Gly Pro Trp Ala Phe Thr Gln Asn

```
1               5                   10                  15

Lys Asn Val Arg Met Glu Leu Lys
            20

<210> SEQ ID NO 140
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Val sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 140

Xaa Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 141
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Ile sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 141

Xaa Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 142
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Leu sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 142

Xaa Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 143
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Ala sub Cys and Lys sub Cys)frag
<220> FEATURE:
<221> NAME/KEY: VARIANT
<222> LOCATION: (1)..(1)
```

<223> OTHER INFORMATION: Xaa is Arg linked to MPA-AEEA

<400> SEQUENCE: 143

Xaa Asn Pro Gly Gly Gln Met Glu Gly Pro Trp Ala Phe Thr Gln Asn
1               5                   10                  15

Lys Asn Val Arg Met Glu Leu Lys
            20

<210> SEQ ID NO 144
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Val sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 144

Xaa Asn Pro Gly Gly Gln Met Glu Gly Pro Trp Val Phe Thr Gln Asn
1               5                   10                  15

Lys Asn Val Arg Met Glu Leu Lys
            20

<210> SEQ ID NO 145
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Ile sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 145

Xaa Asn Pro Gly Gly Gln Met Glu Gly Pro Trp Ile Phe Thr Gln Asn
1               5                   10                  15

Lys Asn Val Arg Met Glu Leu Lys
            20

<210> SEQ ID NO 146
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Leu sub Cys and Lys sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 146

Xaa Asn Pro Gly Gly Gln Met Glu Gly Pro Trp Leu Phe Thr Gln Asn
1               5                   10                  15

Lys Asn Val Arg Met Glu Leu Lys
            20

<210> SEQ ID NO 147
<211> LENGTH: 24
<212> TYPE: PRT
<213> ORGANISM: Artificial Sequence
<220> FEATURE:

```
<223> OTHER INFORMATION: Synthetic Peptide Mod-Kr2(56-79 Active Zone w
      Ala sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (24)..(24)
<223> OTHER INFORMATION: Xaa is Lys linked to N-epsilon-MPA

<400> SEQUENCE: 147

Xaa Asn Pro Gly Gly Gln Met Glu Gly Pro Trp Ala Phe Thr Gln Asn
1               5                   10                  15

Lys Asn Val Arg Met Glu Leu Xaa
            20

<210> SEQ ID NO 148
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Val sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (24)..(24)
<223> OTHER INFORMATION: Xaa is Lys linked to N-epsilon-MPA

<400> SEQUENCE: 148

Xaa Asn Pro Gly Gly Gln Met Glu Gly Pro Trp Val Phe Thr Gln Asn
1               5                   10                  15

Lys Asn Val Arg Met Glu Leu Xaa
            20

<210> SEQ ID NO 149
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Ile sub Cys and Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (24)..(24)
<223> OTHER INFORMATION: Xaa is Lys linked to N-epsilon-MPA

<400> SEQUENCE: 149

Xaa Asn Pro Gly Gly Gln Met Glu Gly Pro Trp Ile Phe Thr Gln Asn
1               5                   10                  15

Lys Asn Val Arg Met Glu Leu Xaa
            20

<210> SEQ ID NO 150
<211> LENGTH: 24
<212> TYPE: PRT
<213> ORGANISM: Artificial Sequence
<220> FEATURE:
<223> OTHER INFORMATION: Synthetic Peptide Mod-Kr2(56-79 Active Zone w
      Leu sub Cys and Lys sub Cys)frag
<220> FEATURE:
<221> NAME/KEY: VARIANT
```

```
<222> LOCATION: (1)..(1)
<223> OTHER INFORMATION: Xaa is Arg linked to NAc
<220> FEATURE:
<221> NAME/KEY: VARIANT
<222> LOCATION: (24)..(24)
<223> OTHER INFORMATION: Xaa is Lys linked to N-epsilon-MPA

<400> SEQUENCE: 150

Xaa Asn Pro Gly Gly Gln Met Glu Gly Pro Trp Leu Phe Thr Gln Asn
1               5                   10                  15

Lys Asn Val Arg Met Glu Leu Xaa
            20

<210> SEQ ID NO 151
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Ala sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 151

Xaa Asn Pro Gly Gly Gln Met Glu Gly Pro Trp Ala Phe Thr Gln Asn
1               5                   10                  15

Lys Asn Val Arg Met Glu Leu
            20

<210> SEQ ID NO 152
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Val sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 152

Xaa Asn Pro Gly Gly Gln Met Glu Gly Pro Trp Val Phe Thr Gln Asn
1               5                   10                  15

Lys Asn Val Arg Met Glu Leu
            20

<210> SEQ ID NO 153
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Ile sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 153

Xaa Asn Pro Gly Gly Gln Met Glu Gly Pro Trp Ile Phe Thr Gln Asn
1               5                   10                  15

Lys Asn Val Arg Met Glu Leu
            20
```

-continued

```
<210> SEQ ID NO 154
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Leu sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 154

Xaa Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 155
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Ala sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 155

Xaa Asn Pro Gly Gly Gln Met Glu Gly Pro Trp Ala Phe Thr Gln Asn
1               5                   10                  15

Lys Asn Val Arg Met Glu Leu
            20

<210> SEQ ID NO 156
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Val sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 156

Xaa Asn Pro Gly Gly Gln Met Glu Gly Pro Trp Val Phe Thr Gln Asn
1               5                   10                  15

Lys Asn Val Arg Met Glu Leu
            20

<210> SEQ ID NO 157
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Ile sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 157

Xaa Asn Pro Gly Gly Gln Met Glu Gly Pro Trp Ile Phe Thr Gln Asn
1               5                   10                  15
```

Lys Asn Val Arg Met Glu Leu
            20

<210> SEQ ID NO 158
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Leu sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 158

Xaa Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 159
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Ala sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 159

Xaa Asn Pro Gly Gly Gln Met Glu Gly Pro Trp Ala Phe Thr Gln Asn
1               5                   10                  15

Lys Asn Val Arg Met Glu Leu
            20

<210> SEQ ID NO 160
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Val sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 160

Xaa Asn Pro Gly Gly Gln Met Glu Gly Pro Trp Val Phe Thr Gln Asn
1               5                   10                  15

Lys Asn Val Arg Met Glu Leu
            20

<210> SEQ ID NO 161
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Ile sub Cys)frag
<220> FEATURE:
<221> NAME/KEY: VARIANT
<222> LOCATION: (1)..(1)
<223> OTHER INFORMATION: Xaa is Arg linked to MPA-AEEA -continued

```
<400> SEQUENCE: 161

Xaa Asn Pro Gly Gly Gln Met Glu Gly Pro Trp Ile Phe Thr Gln Asn
1               5                   10                  15

Lys Asn Val Arg Met Glu Leu
            20

<210> SEQ ID NO 162
<211> LENGTH: 23
<212> TYPE: PRT
<213> ORGANISM: Artificial Sequence
<220> FEATURE:
<223> OTHER INFORMATION: Synthetic Peptide Mod-Kr2(56-78 Active Zone w
      Leu sub Cys)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 162

Xaa Asn Pro Gly Gly Gln Met Glu Gly Pro Trp Leu Phe Thr Gln Asn
1               5                   10                  15

Lys Asn Val Arg Met Glu Leu
            20

<210> SEQ ID NO 163
<211> LENGTH: 12
<212> TYPE: PRT
<213> ORGANISM: Artificial Sequence
<220> FEATURE:
<223> OTHER INFORMATION: Synthetic Peptide Mod-Kr2(56-67 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to NAc

<400> SEQUENCE: 163

Xaa Asn Pro Gly Gly Gln Met Glu Gly Pro Trp Lys
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Synthetic Peptide Mod-Kr2(56-67 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to MPA

<400> SEQUENCE: 164

Xaa Asn Pro Gly Gly Gln Met Glu Gly Pro Trp Lys
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic Peptide Mod-Kr2(56-67 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to MPA-AEEA
```

```
<400> SEQUENCE: 165

Xaa Asn Pro Gly Gly Gln Met Glu Gly Pro Trp Lys
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Synthetic Peptide Mod-Kr2(56-67 Active Zone w
      Lys sub Cys)frag
<220> FEATURE:
<221> NAME/KEY: VARIANT
<222> LOCATION: (1)..(1)
<223> OTHER INFORMATION: Xaa is Arg linked to NAc
<220> FEATURE:
<221> NAME/KEY: VARIANT
<222> LOCATION: (12)..(12)
<223> OTHER INFORMATION: Xaa is Lys linked to N-epsilon-MPA

<400> SEQUENCE: 166

Xaa Asn Pro Gly Gly Gln Met Glu Gly Pro Trp Xaa
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Synthetic Peptide Mod-Kr2(56-66 Active
      Zone)frag
<220> FEATURE:
<221> NAME/KEY: VARIANT
<222> LOCATION: (1)..(1)
<223> OTHER INFORMATION: Xaa is Arg linked to NAc

<400> SEQUENCE: 167

Xaa Asn Pro Gly Gly Gln Met Glu Gly Pro Trp
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic Peptide Mod-Kr2(56-66 Active
      Zone)frag
<220> FEATURE:
<221> NAME/KEY: VARIANT
<222> LOCATION: (1)..(1)
<223> OTHER INFORMATION: Xaa is Arg linked to MPA

<400> SEQUENCE: 168

Xaa Asn Pro Gly Gly Gln Met Glu Gly Pro Trp
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Synthetic Peptide Mod-Kr2(56-66 Active
      Zone)frag
<220> FEATURE:
<221> NAME/KEY: VARIANT
<222> LOCATION: (1)..(1)
<223> OTHER INFORMATION: Xaa is Arg linked to MPA-AEEA

<400> SEQUENCE: 169

Xaa Asn Pro Gly Gly Gln Met Glu Gly Pro Trp
```

<210> SEQ ID NO 170
<211> LENGTH: 12
<212> TYPE: PRT
<213> ORGANISM: Artificial Sequence
<220> FEATURE:
<223> OTHER INFORMATION: Synthetic Peptide Mod-Kr2(68-79 Active Zone w
    Lys sub Cys)frag
<220> FEATURE:
<221> NAME/KEY: VARIANT
<222> LOCATION: (1)..(1)
<223> OTHER INFORMATION: Xaa is Phe linked to NAc

<400> SEQUENCE: 170

Xaa Thr Gln Asn Lys Asn Val Arg Met Glu Leu Lys
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic Peptide Mod-Kr2(68-79 Active Zone w
    Lys sub Cys)frag
<220> FEATURE:
<221> NAME/KEY: VARIANT
<222> LOCATION: (1)..(1)
<223> OTHER INFORMATION: Xaa is Phe linked to MPA

<400> SEQUENCE: 171

Xaa Thr Gln Asn Lys Asn Val Arg Met Glu Leu Lys
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Synthetic Peptide Mod-Kr2(68-79 Active Zone w
    Lys sub Cys)frag
<220> FEATURE:
<221> NAME/KEY: VARIANT
<222> LOCATION: (1)..(1)
<223> OTHER INFORMATION: Xaa is Phe linked to MPA-AEEA

<400> SEQUENCE: 172

Xaa Thr Gln Asn Lys Asn Val Arg Met Glu Leu Lys
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Synthetic Peptide Mod-Kr2(68-79 Active Zone w
    Lys sub Cys)frag
<220> FEATURE:
<221> NAME/KEY: VARIANT
<222> LOCATION: (1)..(1)
<223> OTHER INFORMATION: Phe is NAc-Phe
<220> FEATURE:
<221> NAME/KEY: VARIANT
<222> LOCATION: (12)..(12)
<223> OTHER INFORMATION: Xaa is Lys linked to N-epsilon-MPA

<400> SEQUENCE: 173

Xaa Thr Gln Asn Lys Asn Val Arg Met Glu Leu Xaa
1               5                   10

-continued

<210> SEQ ID NO 174
<211> LENGTH: 11
<212> TYPE: PRT
<213> ORGANISM: Artificial Sequence
<220> FEATURE:
<223> OTHER INFORMATION: Synthetic Peptide Mod-Kr2(68-78 Active
      Zone)frag
<220> FEATURE:
<221> NAME/KEY: VARIANT
<222> LOCATION: (1)..(1)
<223> OTHER INFORMATION: Xaa is Phe linked to NAc

<400> SEQUENCE: 174

Xaa Thr Gln Asn Lys Asn Val Arg Met Glu Leu
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Synthetic Peptide Mod-Kr2(68-78 Active
      Zone)frag
<220> FEATURE:
<221> NAME/KEY: VARIANT
<222> LOCATION: (1)..(1)
<223> OTHER INFORMATION: Xaa is Phe linked to MPA

<400> SEQUENCE: 175

Xaa Thr Gln Asn Lys Asn Val Arg Met Glu Leu
1               5                   10

<210> SEQ ID NO 176
<211> LENGTH: 11
<212> TYPE: PRT
<213> ORGANISM: Artificial Sequence
<220> FEATURE:
<223> OTHER INFORMATION: Synthetic Peptide Mod-Kr2(68-78 Active
      Zone)frag
<220> FEATURE:
<221> NAME/KEY: VARIANT
<222> LOCATION: (1)..(1)
<223> OTHER INFORMATION: Xaa is Phe linked to MPA-AEEA

<400> SEQUENCE: 176

Xaa Thr Gln Asn Lys Asn Val Arg Met Glu Leu
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic Peptide Mod-Kr2(69-78 Active
      Zone)frag
<220> FEATURE:
<221> NAME/KEY: VARIANT
<222> LOCATION: (1)..(1)
<223> OTHER INFORMATION: Xaa is Thr linked to NAc

<400> SEQUENCE: 177

Xaa Gln Asn Lys Asn Val Arg Met Glu Leu
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic Peptide Mod-Kr2(69-78 Active
      Zone)frag

```
<220> FEATURE:
<221> NAME/KEY: VARIANT
<222> LOCATION: (1)..(1)
<223> OTHER INFORMATION: Xaa is Thr linked to MPA

<400> SEQUENCE: 178

Xaa Gln Asn Lys Asn Val Arg Met Glu Leu
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic Peptide Mod-Kr2(69-78 Active
      Zone)frag
<220> FEATURE:
<221> NAME/KEY: VARIANT
<222> LOCATION: (1)..(1)
<223> OTHER INFORMATION: Xaa is Thr linked to MPA-AEEA

<400> SEQUENCE: 179

Xaa Gln Asn Lys Asn Val Arg Met Glu Leu
1               5                   10

<210> SEQ ID NO 180
<211> LENGTH: 9
<212> TYPE: PRT
<213> ORGANISM: Artificial Sequence
<220> FEATURE:
<223> OTHER INFORMATION: Synthetic Peptide Mod-Kr2(70-78 Active
      Zone)frag
<220> FEATURE:
<221> NAME/KEY: VARIANT
<222> LOCATION: (1)..(1)
<223> OTHER INFORMATION: Xaa is Gln linked to NAc

<400> SEQUENCE: 180

Xaa Asn Lys Asn Val Arg Met Glu Leu
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic Peptide Mod-Kr2(70-78 Active
      Zone)frag
<220> FEATURE:
<221> NAME/KEY: VARIANT
<222> LOCATION: (1)..(1)
<223> OTHER INFORMATION: Xaa is Gln linked to MPA

<400> SEQUENCE: 181

Xaa Asn Lys Asn Val Arg Met Glu Leu
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Peptide Mod-Kr2(70-78 Active
      Zone)frag
<220> FEATURE:
<221> NAME/KEY: VARIANT
<222> LOCATION: (1)..(1)
<223> OTHER INFORMATION: Xaa is Gln linked to MPA-AEEA

<400> SEQUENCE: 182
```

```
Xaa Asn Lys Asn Val Arg Met Glu Leu
1               5
```

<210> SEQ ID NO 183
<211> LENGTH: 8
<212> TYPE: PRT
<213> ORGANISM: Artificial Sequence
<220> FEATURE:
<223> OTHER INFORMATION: Synthetic Peptide Mod-Kr2(70-77 Active
      Zone)frag
<220> FEATURE:
<221> NAME/KEY: VARIANT
<222> LOCATION: (1)..(1)
<223> OTHER INFORMATION: Xaa is Gln linked to NAc

<400> SEQUENCE: 183

```
Xaa Asn Lys Asn Val Arg Met Glu
1               5
```

<210> SEQ ID NO 184
<211> LENGTH: 8
<212> TYPE: PRT
<213> ORGANISM: Artificial Sequence
<220> FEATURE:
<223> OTHER INFORMATION: Synthetic Peptide Mod-Kr2(70-77 Active
      Zone)frag
<220> FEATURE:
<221> NAME/KEY: VARIANT
<222> LOCATION: (1)..(1)
<223> OTHER INFORMATION: Xaa is Gln linked to MPA

<400> SEQUENCE: 184

```
Xaa Asn Lys Asn Val Arg Met Glu
1               5
```

<210> SEQ ID NO 185
<211> LENGTH: 8
<212> TYPE: PRT
<213> ORGANISM: Artificial Sequence
<220> FEATURE:
<223> OTHER INFORMATION: Synthetic Peptide Mod-Kr2(70-77 Active
      Zone)frag
<220> FEATURE:
<221> NAME/KEY: VARIANT
<222> LOCATION: (1)..(1)
<223> OTHER INFORMATION: Xaa is Gln linked to MPA-AEEA

<400> SEQUENCE: 185

```
Xaa Asn Lys Asn Val Arg Met Glu
1               5
```

<210> SEQ ID NO 186
<211> LENGTH: 93
<212> TYPE: PRT
<213> ORGANISM: Artificial Sequence
<220> FEATURE:
<223> OTHER INFORMATION: Synthetic Peptide Mod-Kr1(1-93 Active
      Zone)frag
<220> FEATURE:
<221> NAME/KEY: VARIANT
<222> LOCATION: (1)..(1)
<223> OTHER INFORMATION: Xaa is Gly linked to NAc

<400> SEQUENCE: 186

```
Xaa Ser Asn Lys Asn His Lys Cys Tyr Asn Ser Thr Gly Val Asp Tyr
1               5                   10                  15

Arg Gly Thr Val Ser Val Thr Lys Ser Gly Arg Gln Cys Gln Pro Trp
            20                  25                  30

Asn Ser Gln Tyr Pro His Thr His Thr Phe Thr Ala Leu Arg Phe Pro
```

```
                    35                  40                  45

Glu Leu Asn Gly Gly His Ser Tyr Cys Arg Asn Pro Gly Asn Gln Lys
 50                  55                  60

Glu Ala Pro Trp Cys Phe Thr Leu Asp Glu Asn Phe Lys Ser Asp Leu
 65                  70                  75                  80

Cys Asp Ile Pro Ala Cys Asp Ser Lys Asp Ser Asp Ile
                 85                  90

<210> SEQ ID NO 187
<211> LENGTH: 93
<212> TYPE: PRT
<213> ORGANISM: Artificial Sequence
<220> FEATURE:
<223> OTHER INFORMATION: Synthetic Peptide Mod-Kr1(1-93 Active
      Zone)frag
<220> FEATURE:
<221> NAME/KEY: VARIANT
<222> LOCATION: (1)..(1)
<223> OTHER INFORMATION: Xaa is Gly linked to MPA

<400> SEQUENCE: 187

Xaa Ser Asn Lys Asn His Lys Cys Tyr Asn Ser Thr Gly Val Asp Tyr
 1               5                  10                  15

Arg Gly Thr Val Ser Val Thr Lys Ser Gly Arg Gln Cys Gln Pro Trp
                20                  25                  30

Asn Ser Gln Tyr Pro His Thr His Thr Phe Thr Ala Leu Arg Phe Pro
            35                  40                  45

Glu Leu Asn Gly Gly His Ser Tyr Cys Arg Asn Pro Gly Asn Gln Lys
 50                  55                  60

Glu Ala Pro Trp Cys Phe Thr Leu Asp Glu Asn Phe Lys Ser Asp Leu
 65                  70                  75                  80

Cys Asp Ile Pro Ala Cys Asp Ser Lys Asp Ser Asp Ile
                 85                  90

<210> SEQ ID NO 188
<211> LENGTH: 93
<212> TYPE: PRT
<213> ORGANISM: Artificial Sequence
<220> FEATURE:
<223> OTHER INFORMATION: Synthetic Peptide Mod-Kr1(1-93 Active
      Zone)frag
<220> FEATURE:
<221> NAME/KEY: VARIANT
<222> LOCATION: (1)..(1)
<223> OTHER INFORMATION: Xaa is Gly linked to MPA-AEEA

<400> SEQUENCE: 188

Xaa Ser Asn Lys Asn His Lys Cys Tyr Asn Ser Thr Gly Val Asp Tyr
 1               5                  10                  15

Arg Gly Thr Val Ser Val Thr Lys Ser Gly Arg Gln Cys Gln Pro Trp
                20                  25                  30

Asn Ser Gln Tyr Pro His Thr His Thr Phe Thr Ala Leu Arg Phe Pro
            35                  40                  45

Glu Leu Asn Gly Gly His Ser Tyr Cys Arg Asn Pro Gly Asn Gln Lys
 50                  55                  60

Glu Ala Pro Trp Cys Phe Thr Leu Asp Glu Asn Phe Lys Ser Asp Leu
 65                  70                  75                  80

Cys Asp Ile Pro Ala Cys Asp Ser Lys Asp Ser Asp Ile
                 85                  90

<210> SEQ ID NO 189
```

```
<211> LENGTH: 91
<212> TYPE: PRT
<213> ORGANISM: Artificial Sequence
<220> FEATURE:
<223> OTHER INFORMATION: Synthetic Peptide K5(1-91 Active Zone)frag

<400> SEQUENCE: 189

Gly Ser Ser Glu Glu Asp Cys Met Phe Gly Asn Gly Lys Gly Tyr Arg
1               5                   10                  15

Gly Lys Arg Ala Thr Thr Val Thr Gly Thr Pro Cys Gln Asp Trp Ala
            20                  25                  30

Ala Gln Glu Pro His Arg His Ser Ile Phe Thr Pro Glu Thr Asn Pro
        35                  40                  45

Arg Ala Gly Leu Glu Lys Asn Tyr Cys Arg Asn Pro Asp Gly Asp Val
    50                  55                  60

Gly Gly Pro Trp Cys Tyr Thr Thr Asn Pro Arg Lys Leu Tyr Asp Tyr
65                  70                  75                  80

Cys Asp Val Pro Gln Cys Ala Ala Pro Asp Ile
                85                  90

<210> SEQ ID NO 190
<211> LENGTH: 13
<212> TYPE: PRT
<213> ORGANISM: Artificial Sequence
<220> FEATURE:
<223> OTHER INFORMATION: Synthetic Peptide Kringle 5 fragment

<400> SEQUENCE: 190

Cys Tyr Thr Thr Asn Pro Arg Lys Leu Tyr Asp Tyr Cys
1               5                   10

<210> SEQ ID NO 191
<211> LENGTH: 13
<212> TYPE: PRT
<213> ORGANISM: Artificial Sequence
<220> FEATURE:
<223> OTHER INFORMATION: Synthetic Peptide Kringle 1 (ROR1) fragment

<400> SEQUENCE: 191

Cys Phe Thr Leu Asp Glu Asn Phe Lys Ser Asp Leu Cys
1               5                   10

<210> SEQ ID NO 192
<211> LENGTH: 9
<212> TYPE: PRT
<213> ORGANISM: Artificial Sequence
<220> FEATURE:
<223> OTHER INFORMATION: Synthetic Peptide SARS-CoV-2 (C524-C536)
      fragment

<400> SEQUENCE: 192

Cys Asn Gly Val Glu Gly Phe Asn Cys
1               5

<210> SEQ ID NO 193
<211> LENGTH: 13
<212> TYPE: PRT
<213> ORGANISM: Artificial Sequence
<220> FEATURE:
<223> OTHER INFORMATION: Synthetic Peptide SARS-CoV (E453-V468)
      fragment

<400> SEQUENCE: 193

Glu Asn Gly Val Arg Thr Tyr Asp Phe Asn Pro Asn Val
1               5                   10
```

<210> SEQ ID NO 194
<211> LENGTH: 15
<212> TYPE: PRT
<213> ORGANISM: Artificial Sequence
<220> FEATURE:
<223> OTHER INFORMATION: Synthetic Peptide MERS (C526- Y540) fragment

<400> SEQUENCE: 194

Cys Val Ser Ile Val Pro Ser Thr Val Trp Glu Asp Gly Asp Tyr
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Synthetic Peptide EBOLA (C121-C135) fragment

<400> SEQUENCE: 195

Cys Leu Pro Ala Ala Pro Asp Gly Ile Arg Gly Phe Pro Arg Cys
1               5                   10                  15

<210> SEQ ID NO 196
<211> LENGTH: 12
<212> TYPE: PRT
<213> ORGANISM: Artificial Sequence
<220> FEATURE:
<223> OTHER INFORMATION: Synthetic Peptide ZIKA (C1074-C1085) fragment

<400> SEQUENCE: 196

Cys Pro Gly Thr Lys Val His Val Glu Glu Thr Cys
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Synthetic Peptide Influenza A (C558 C565)
      fragment

<400> SEQUENCE: 197

Cys Ser Asn Gly Ser Leu Gln Cys
1               5

<210> SEQ ID NO 198
<211> LENGTH: 14
<212> TYPE: PRT
<213> ORGANISM: Artificial Sequence
<220> FEATURE:
<223> OTHER INFORMATION: Synthetic Peptide Dengue (C1091 C1104) fragment

<400> SEQUENCE: 198

Cys Thr Leu Pro Pro Leu Arg Tyr Arg Gly Glu Asp Gly Cys
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Synthetic Peptide Japanese Encephalitis Virus
      (C398 C409) fragment

<400> SEQUENCE: 199

Cys Gly Leu Phe Gly Lys Gly Ser Ile Asp Thr Cys

```
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Synthetic Peptide West Nile Virus (C395 C406)
      fragment

<400> SEQUENCE: 200

Cys Gly Leu Phe Gly Lys Gly Ser Ile Asp Thr Cys
1               5                   10

<210> SEQ ID NO 201
<211> LENGTH: 13
<212> TYPE: PRT
<213> ORGANISM: Artificial Sequence
<220> FEATURE:
<223> OTHER INFORMATION: Synthetic Peptide Pep42 Cyclic (C1 - C13)

<400> SEQUENCE: 201

Cys Thr Val Ala Leu Pro Gly Gly Tyr Val Arg Val Cys
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Synthetic Peptide HCoV-NL63 (Common Cold) (C566
      C576) fragment

<400> SEQUENCE: 202

Cys Phe Ser Thr Val Ala Val Pro Gly Ser Cys
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Synthetic Peptide HCov-229E (Common Cold)
      ( C385   C395) fragment

<400> SEQUENCE: 203

Cys Phe Ser Leu Lys Tyr Ile Pro Gly Gly Cys
1               5                   10

<210> SEQ ID NO 204
<211> LENGTH: 15
<212> TYPE: PRT
<213> ORGANISM: Artificial Sequence
<220> FEATURE:
<223> OTHER INFORMATION: Synthetic Peptide HCoV-OC43 (Common Cold)
      (C508 C522) fragment

<400> SEQUENCE: 204

Cys Val Gly Ser Gly Pro Gly Lys Asn Asn Glu Ile Gly Ile Cys
1               5                   10                  15
```

```
<210> SEQ ID NO 205
<211> LENGTH: 11
<212> TYPE: PRT
<213> ORGANISM: Artificial Sequence
<220> FEATURE:
<223> OTHER INFORMATION: Synthetic Peptide HCoV-HKU1 (C484 C494)
      fragment

<400> SEQUENCE: 205

Cys Val Lys Ser Lys Pro Leu Ser Ala Ile Cys
1               5                   10
```